(12) United States Patent
Mylonakis et al.

(10) Patent No.: US 9,861,348 B2
(45) Date of Patent: Jan. 9, 2018

(54) CHITOSAN AND POLYETHYLENE GLYCOL COPOLYMERS AND METHODS AND DEVICES FOR USING SAME FOR SEALING A VASCULAR PUNCTURE

(71) Applicant: ACCESS CLOSURE, INC., Santa Clara, CA (US)

(72) Inventors: Andreas Mylonakis, Santa Clara, CA (US); Florencia Lim, Union City, CA (US)

(73) Assignee: ACCESS CLOSURE, INC., Santa Clara, CA (US)

( * ) Notice: Subject to any disclaimer, the term of this patent is extended or adjusted under 35 U.S.C. 154(b) by 157 days.

(21) Appl. No.: 14/724,591

(22) Filed: May 28, 2015

(65) Prior Publication Data
US 2015/0342581 A1 Dec. 3, 2015

Related U.S. Application Data

(60) Provisional application No. 62/004,806, filed on May 29, 2014.

(51) Int. Cl.
*A61B 17/08* (2006.01)
*A61D 1/00* (2006.01)
(Continued)

(52) U.S. Cl.
CPC ...... *A61B 17/0057* (2013.01); *A61L 24/0031* (2013.01); *A61L 24/08* (2013.01);
(Continued)

(58) Field of Classification Search
CPC .... A61L 31/042; A61L 31/06; A61L 2400/04; A61L 24/0031; A61L 24/08;
(Continued)

(56) References Cited

U.S. PATENT DOCUMENTS 4,394,373 A 7/1983 Malette et al.
4,890,612 A * 1/1990 Kensey ............. A61B 17/0057
606/213
(Continued)

FOREIGN PATENT DOCUMENTS

WO 2011057131 A1 5/2011

OTHER PUBLICATIONS

International Preliminary Report on Patentability for Application No. PCT/US2015/033020, dated Nov. 29, 2016, 6 pages.
(Continued)

*Primary Examiner* — Katherine M Shi
(74) *Attorney, Agent, or Firm* — Amanda F. Maharaj

(57) ABSTRACT

A sealant is provided for sealing a puncture through tissue that comprises an elongate first section including a proximal end, a distal end, and a cross-section sized for delivery into a puncture through tissue, and a second section extending from the distal end of the first section. The first section may be formed from a freeze-dried hydrogel that expands when exposed to physiological fluid within a puncture. The first section comprises chitosan and at least one additional polymer. The second section may be formed from a solid mass of non-freeze-dried, non-cross-linked hydrogel precursors. The precursors are in an unreactive state until exposed to an aqueous physiological environment, whereupon the precursors undergo in-situ crosslinking with one another to provide an adhesive layer bonded to the first section. The second section may further comprise chitosan. Apparatus and methods for delivering the sealant into a puncture through tissue are also provided.

13 Claims, 38 Drawing Sheets

(51) Int. Cl.
    *A61B 17/00*     (2006.01)
    *A61L 24/00*     (2006.01)
    *A61L 24/08*     (2006.01)
    *A61L 31/04*     (2006.01)
    *A61L 31/06*     (2006.01)
    *A61L 31/14*     (2006.01)

(52) U.S. Cl.
    CPC ............. *A61L 31/042* (2013.01); *A61L 31/06* (2013.01); *A61L 31/145* (2013.01); *A61L 31/148* (2013.01); *A61B 2017/0065* (2013.01); *A61B 2017/00623* (2013.01); *A61L 2400/04* (2013.01)

(58) Field of Classification Search
    CPC ........ A61L 31/145; A61L 31/148; C08L 5/08; C08L 71/02; A61B 17/0057; A61B 2017/00623; A61B 2017/0065
    USPC .......................... 606/213, 214; 424/422, 423
    See application file for complete search history.

(56) References Cited

U.S. PATENT DOCUMENTS

| | | | |
|---|---|---|---|
| 5,334,216 | A | 8/1994 | Vidal et al. |
| 6,703,047 | B2 | 3/2004 | Sawhney et al. |
| 7,316,704 | B2 | 1/2008 | Bagaoisan et al. |
| 7,331,979 | B2 | 2/2008 | Khosravi et al. |
| 7,335,220 | B2 | 2/2008 | Khosravi et al. |
| 7,780,980 | B2 | 8/2010 | Sawhney |
| 7,806,856 | B2 | 10/2010 | Bagaoisan et al. |
| 8,012,167 | B2 | 9/2011 | Zhu et al. |
| 8,105,622 | B2 | 1/2012 | Sawhney |
| 8,292,918 | B2 | 10/2012 | Hill et al. |
| 2002/0111651 | A1* | 8/2002 | Ungs ................. A61B 17/0057 606/213 |
| 2005/0070957 | A1* | 3/2005 | Das .................... A61B 17/0057 606/213 |
| 2006/0034930 | A1 | 2/2006 | Khosravi et al. |
| 2007/0231366 | A1 | 10/2007 | Sawhney et al. |
| 2008/0015709 | A1 | 1/2008 | Evans et al. |
| 2008/0082122 | A1 | 4/2008 | Khosravi et al. |
| 2009/0088793 | A1 | 4/2009 | Bagaoisan et al. |
| 2009/0254110 | A1 | 10/2009 | Bagaoisan et al. |
| 2010/0168789 | A1 | 7/2010 | Bagaoisan et al. |
| 2010/0209478 | A1 | 8/2010 | Sawhney et al. |
| 2010/0274280 | A1 | 10/2010 | Sawhney et al. |
| 2010/0280546 | A1 | 11/2010 | Campbell et al. |
| 2012/0238644 | A1 | 9/2012 | Gong et al. |
| 2013/0045182 | A1* | 2/2013 | Gong ................. A61L 24/0031 424/93.1 |
| 2013/0071462 | A1 | 3/2013 | Jarrett et al. |
| 2013/0226229 | A1 | 8/2013 | Uchida et al. |
| 2014/0052168 | A1 | 2/2014 | Sawhney |

OTHER PUBLICATIONS

International Search Report and Written Opinion for Application No. PCT/US2015/033020, dated Aug. 3, 2015, 10 pages.

Final Office Action dated Apr. 13, 2017 for U.S. Appl. No. 13/859,615, 27 pages.

Non-Final Office Action for U.S. Appl. No. 13/354,278, dated Oct. 17, 2016, 9 pages.

Patel V.R., et al., "Preparation and Characterization of Freeze-dried Chitosan-poly(ethylene Oxide) Hydrogels for Site-specific Antibiotic Delivery in the Stomach," Pharmaceutical Research, 1996, vol. 13 (4), pp. 588-593.

Plastic Welding; Wikipedia; https://en.wikipedia.org/wiki/Plastic_welding; accessed Apr. 6, 2017, 8 pages.

* cited by examiner

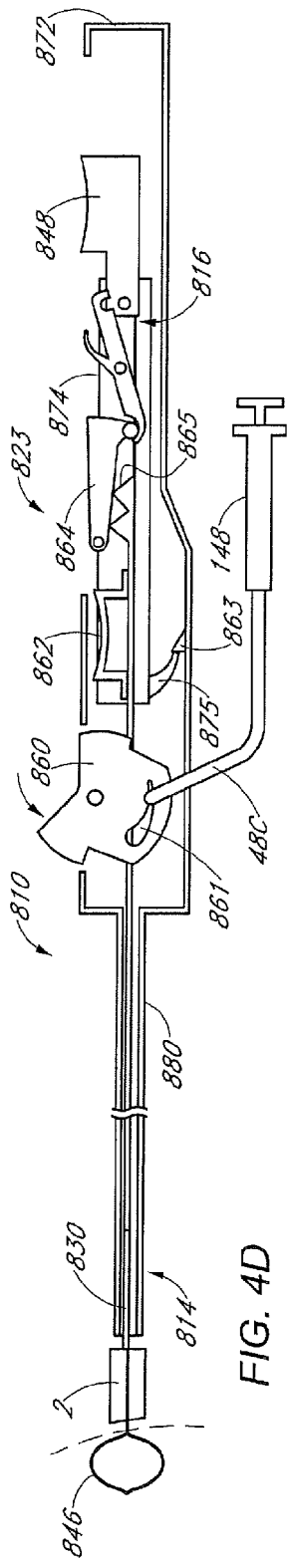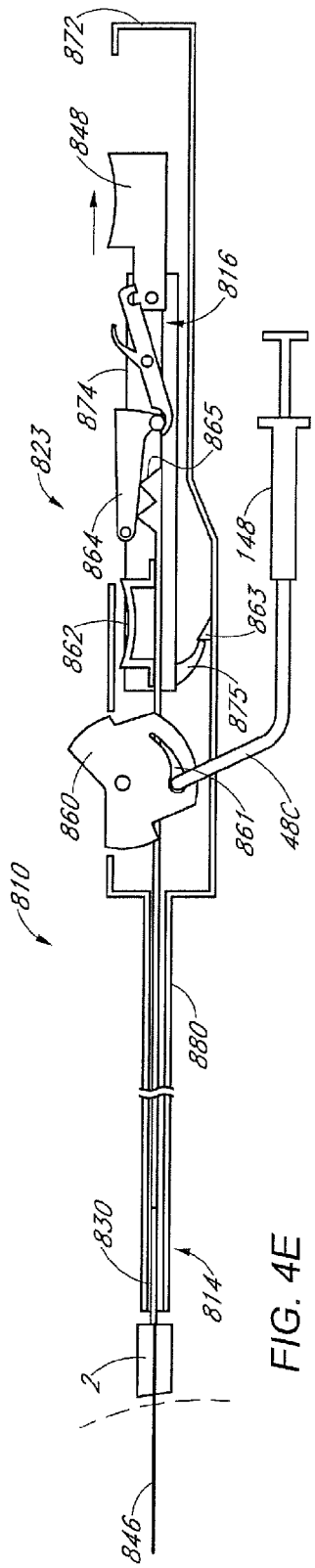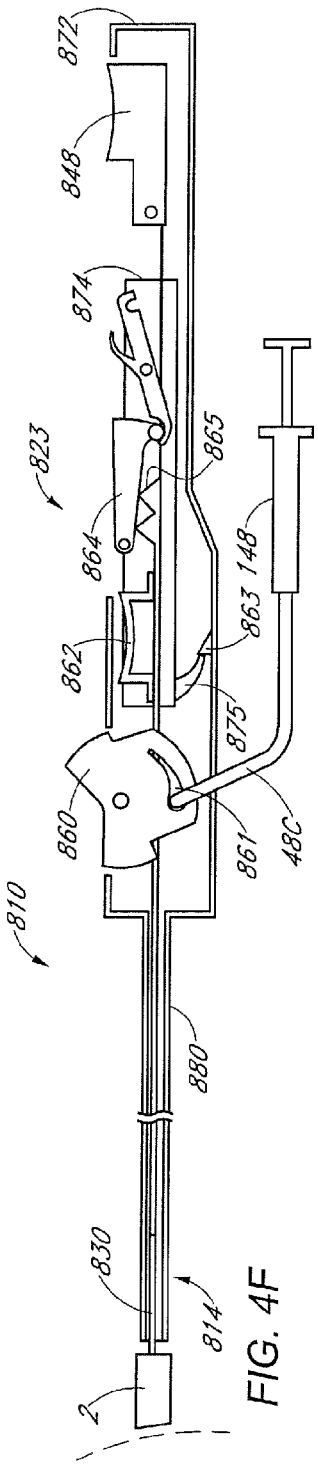

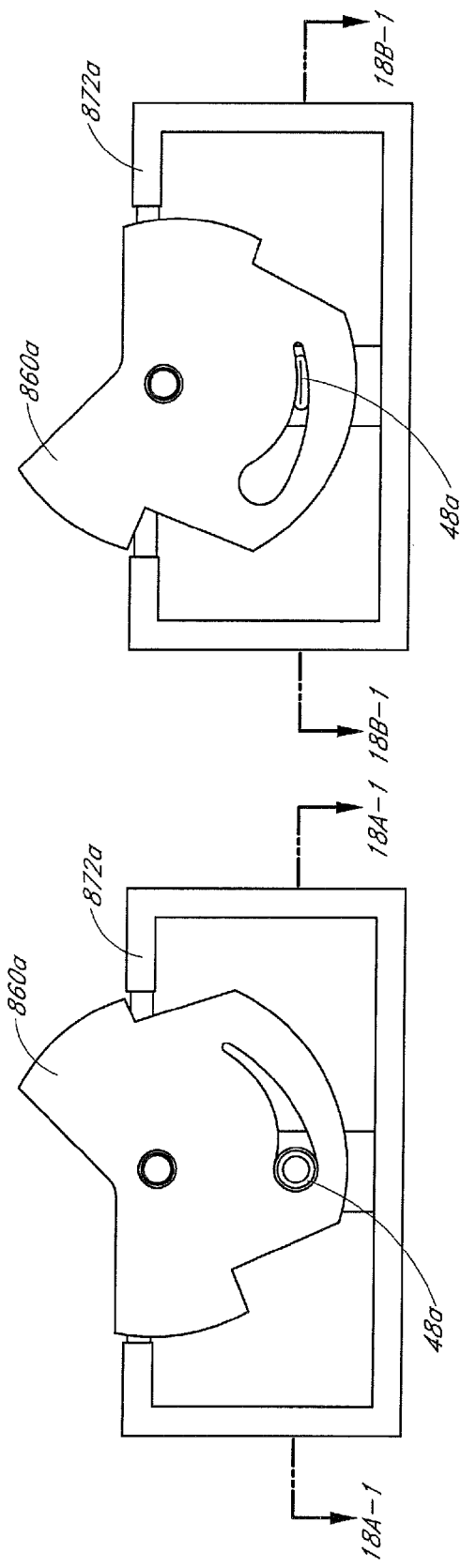

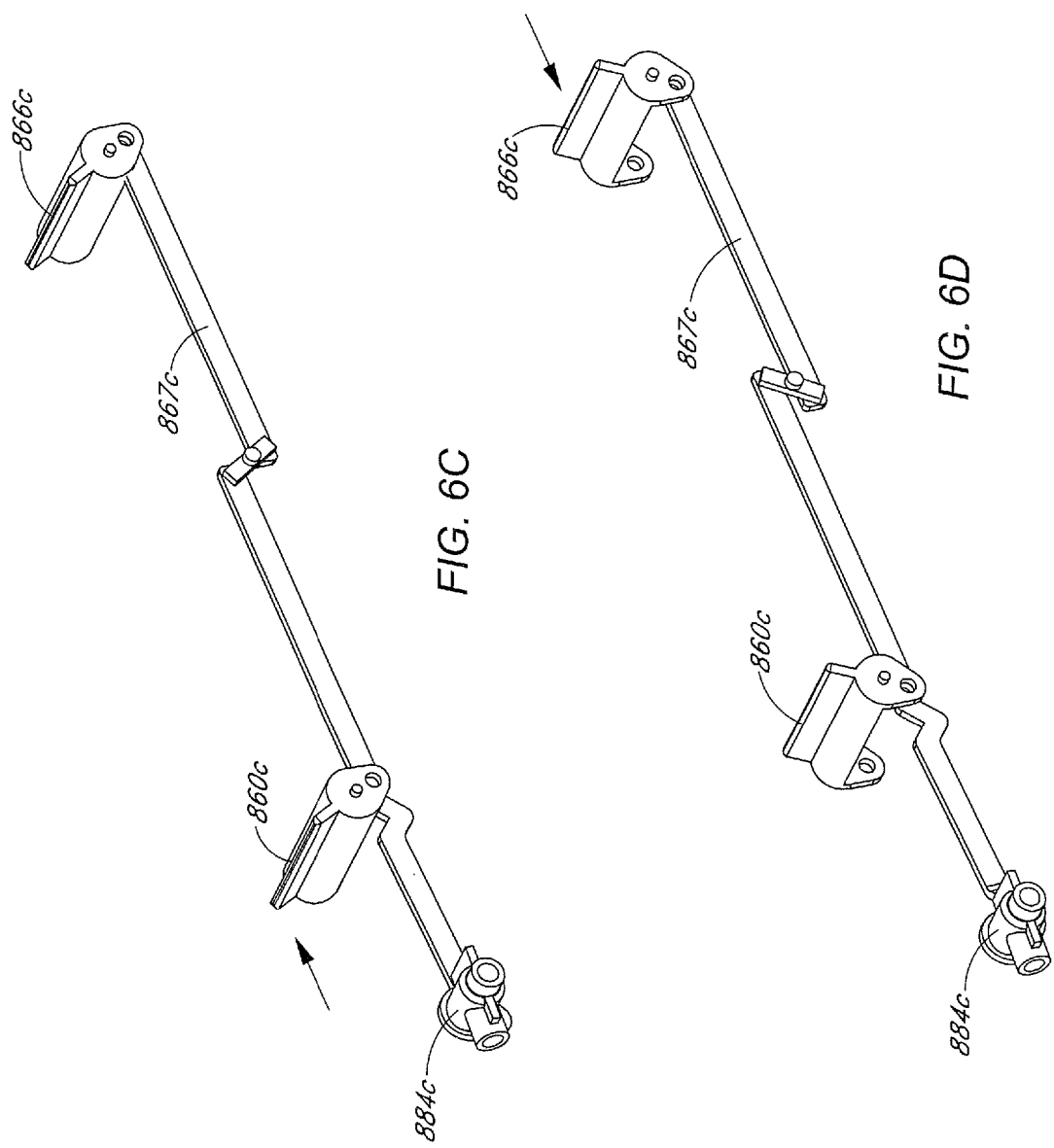

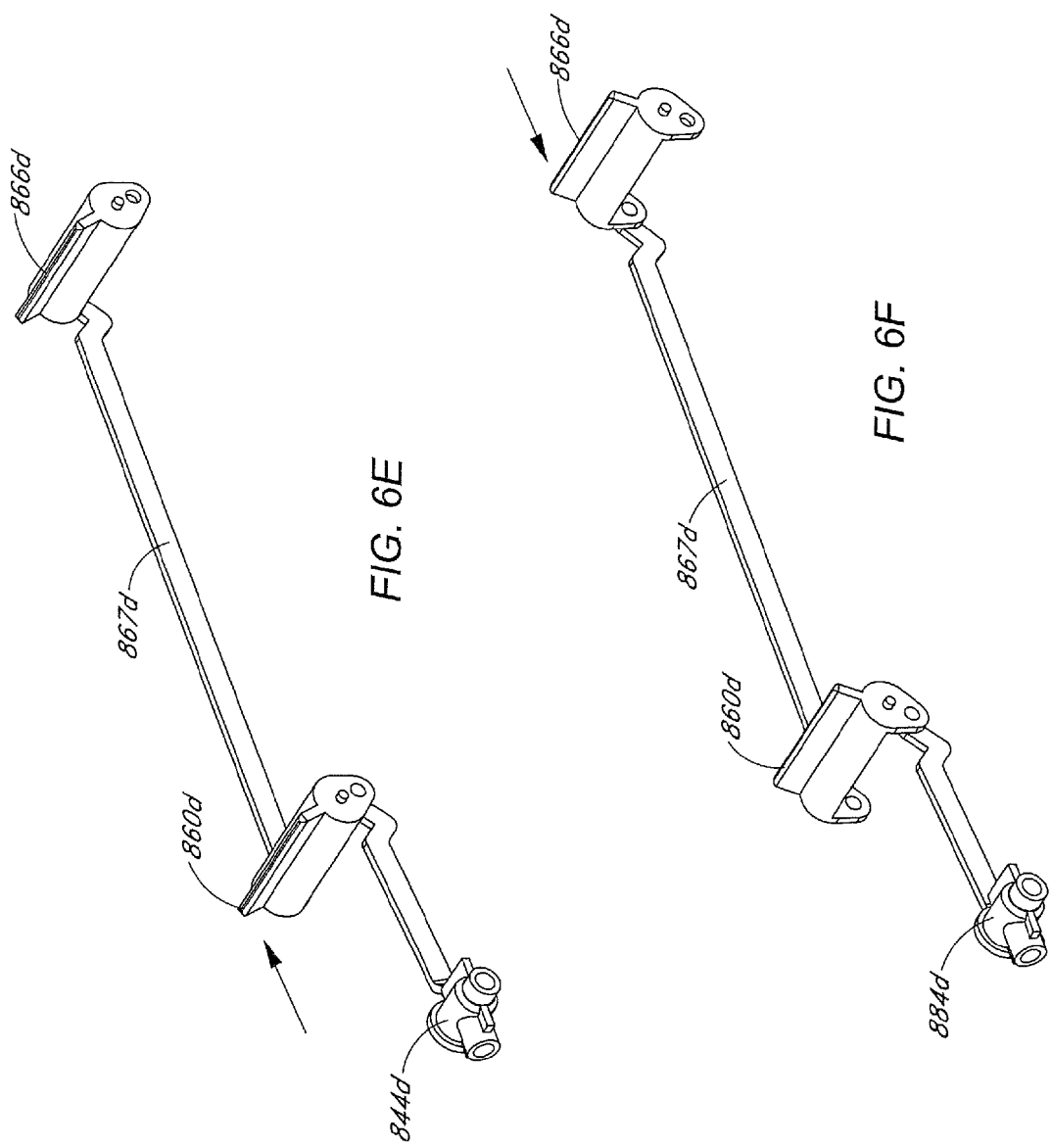

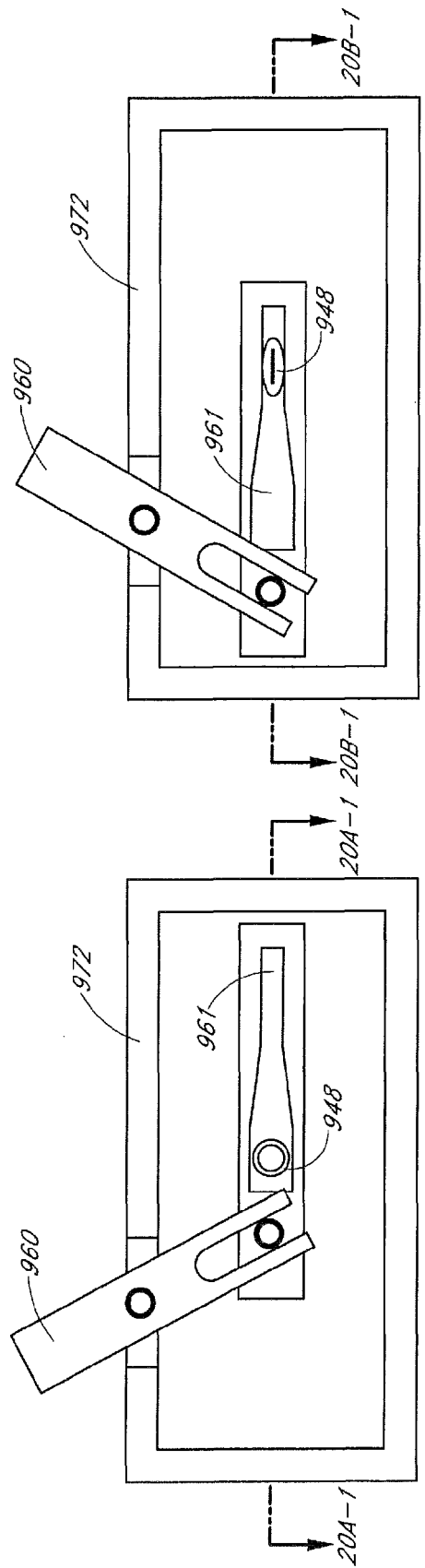
FIG. 7A  FIG. 7A-1  FIG. 7B  FIG. 7B-1

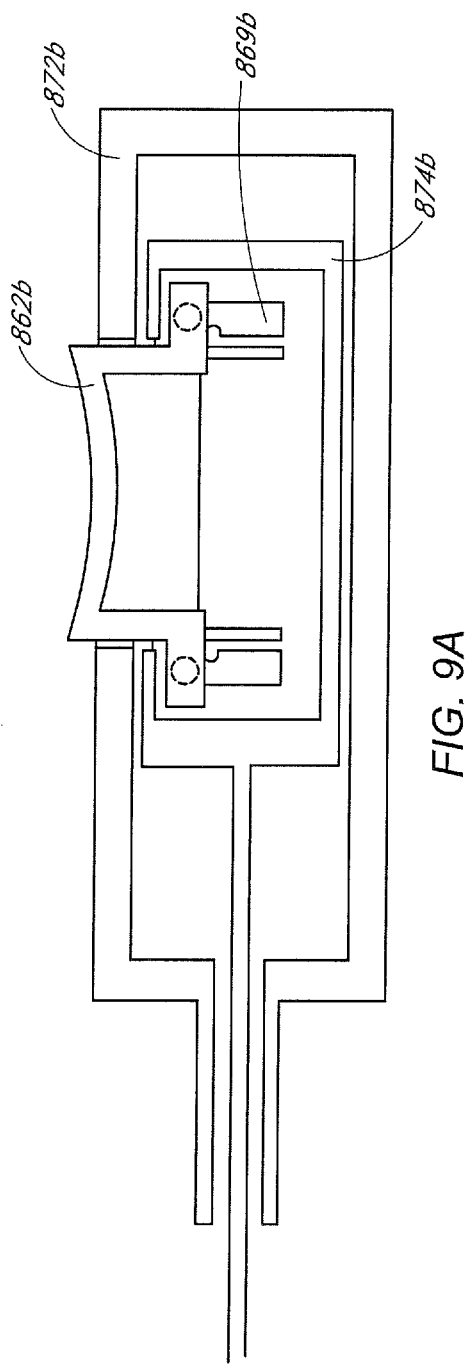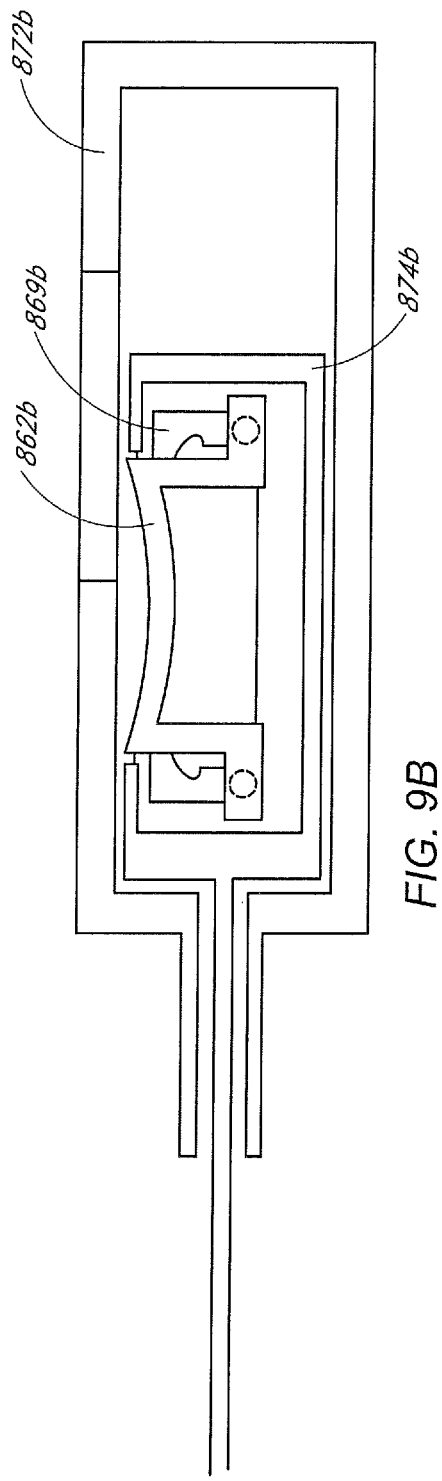
FIG. 9A
FIG. 9B

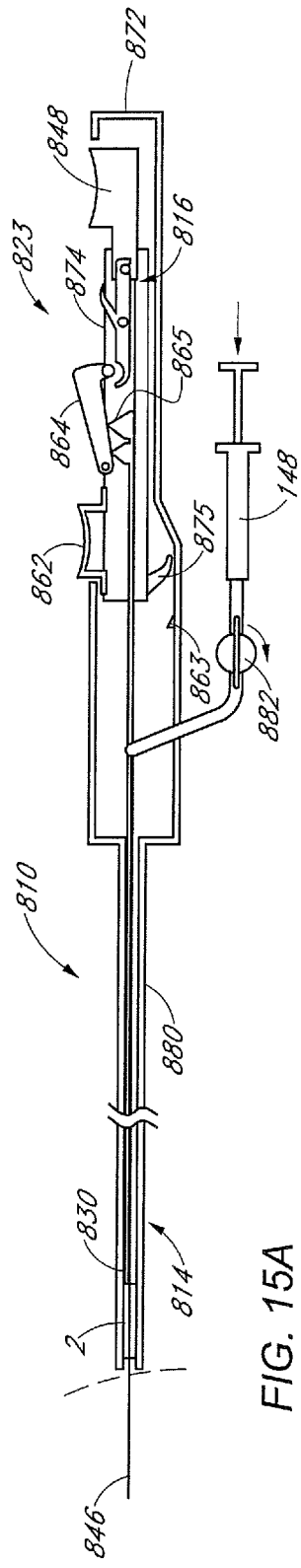
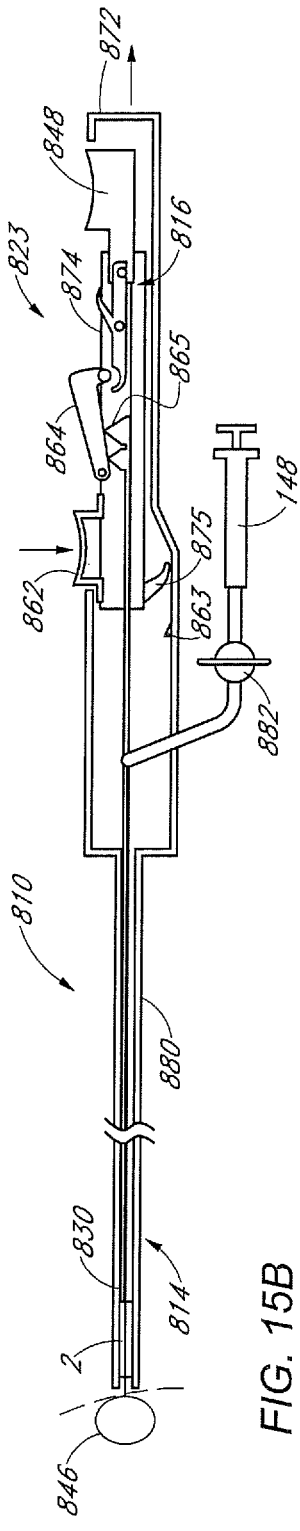
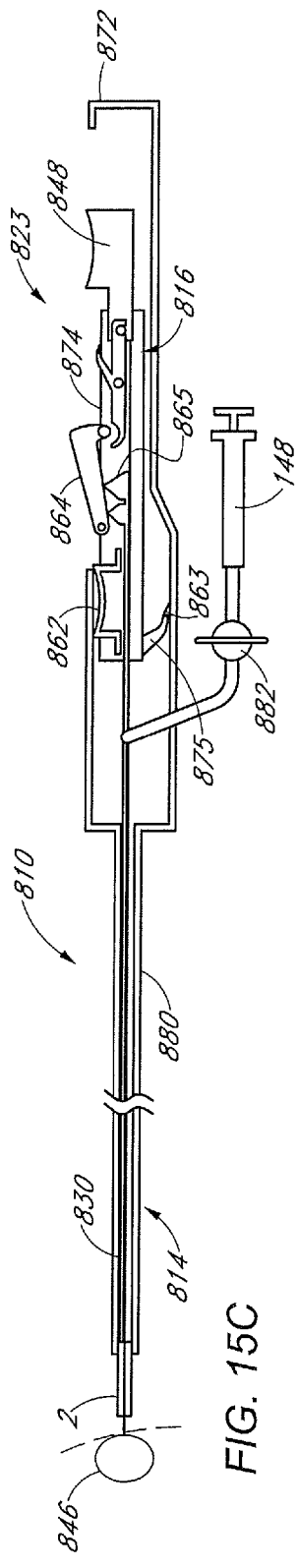
FIG. 15A
FIG. 15B
FIG. 15C

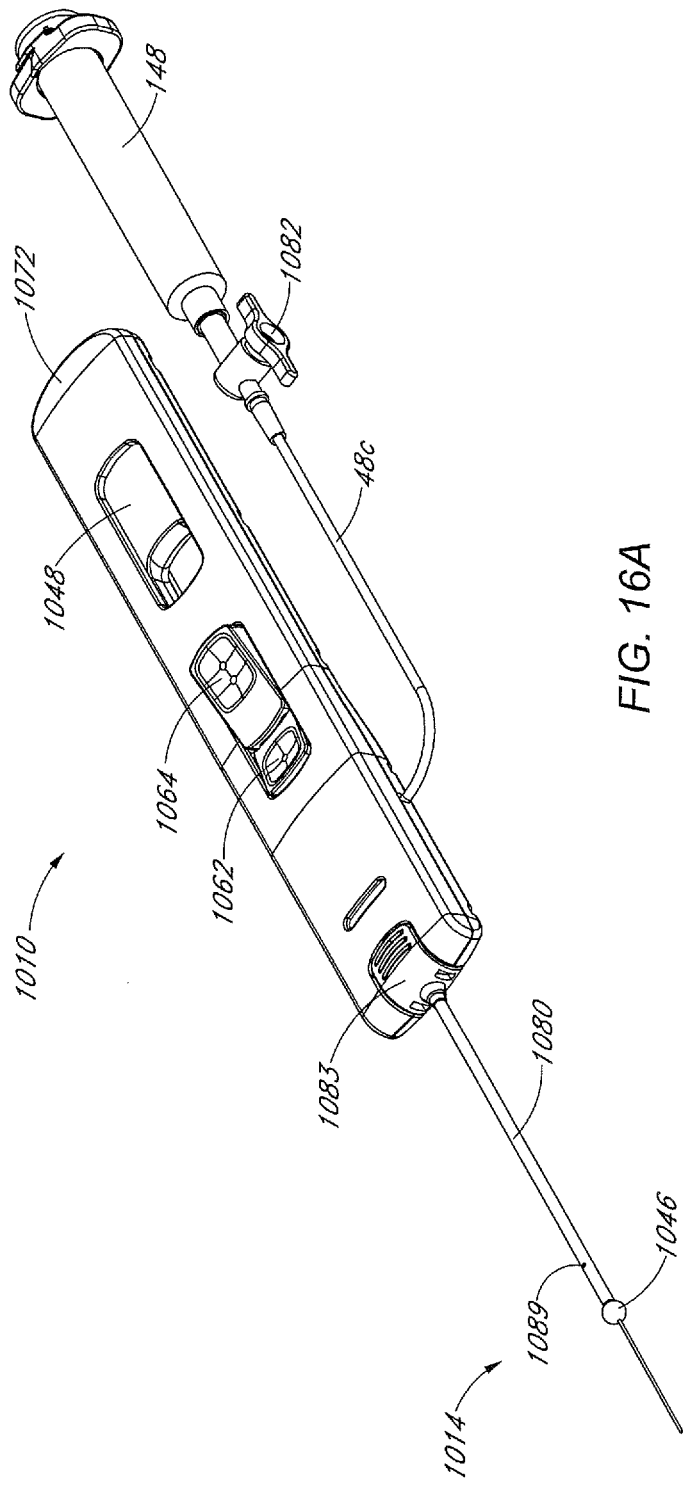

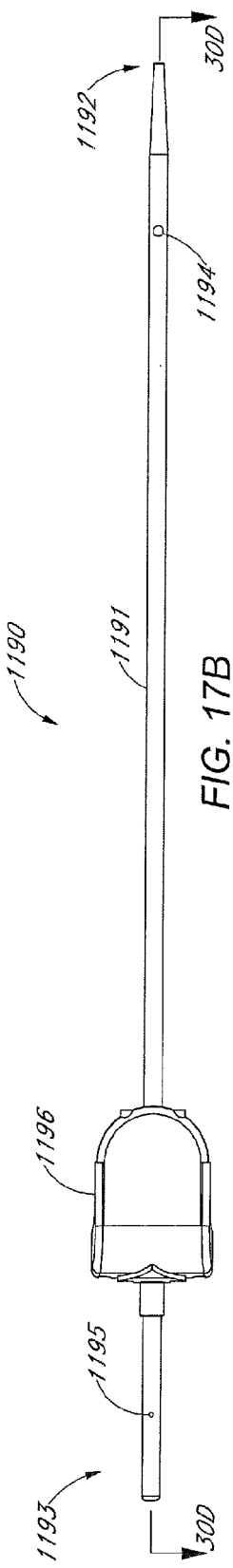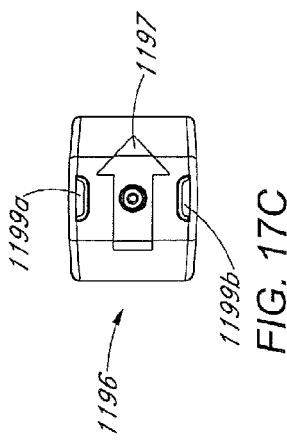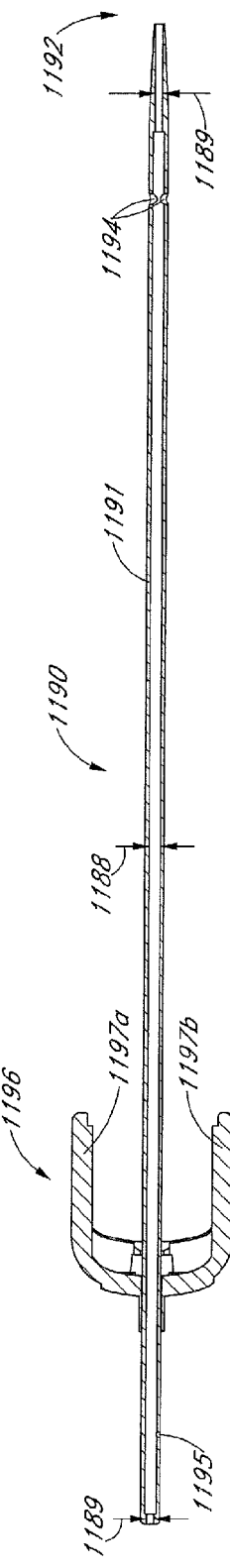
FIG. 17B
FIG. 17C
FIG. 17D

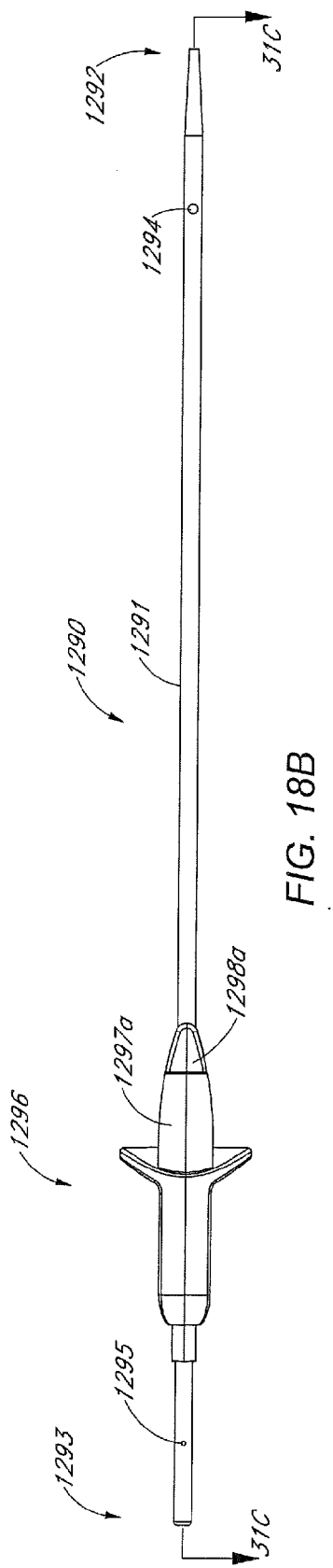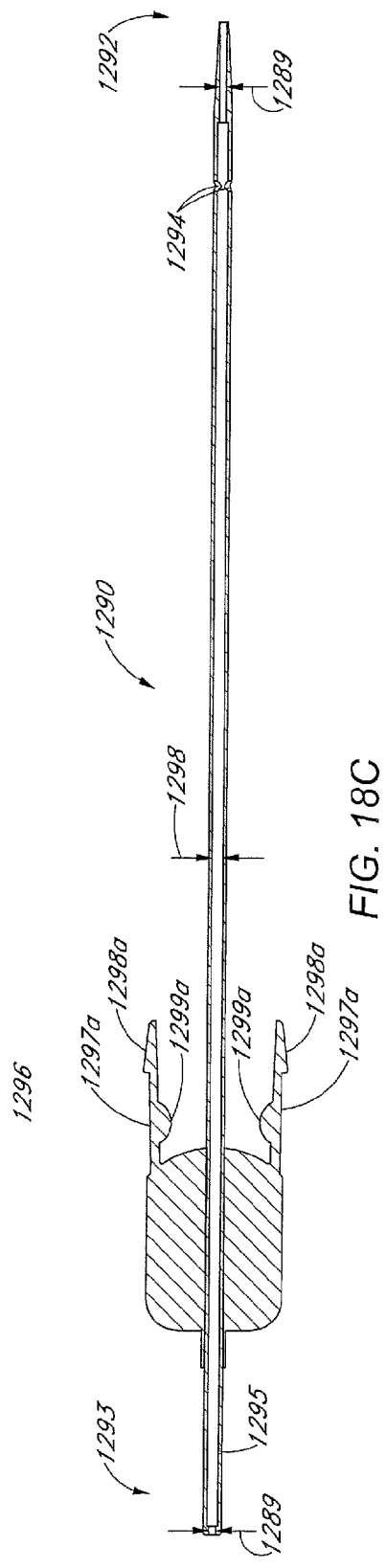
FIG. 18B
FIG. 18C

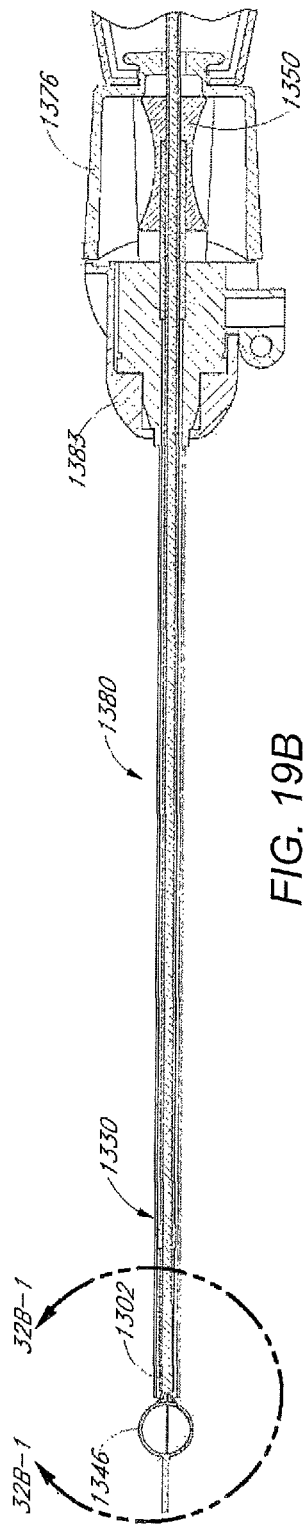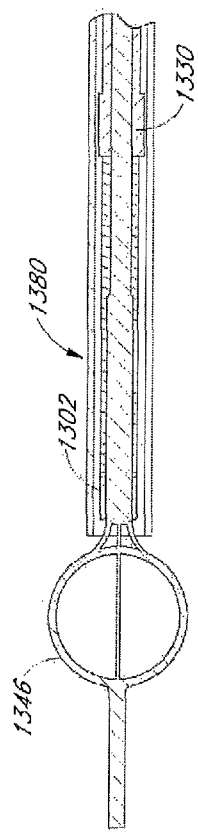
FIG. 19B
FIG. 19B-1

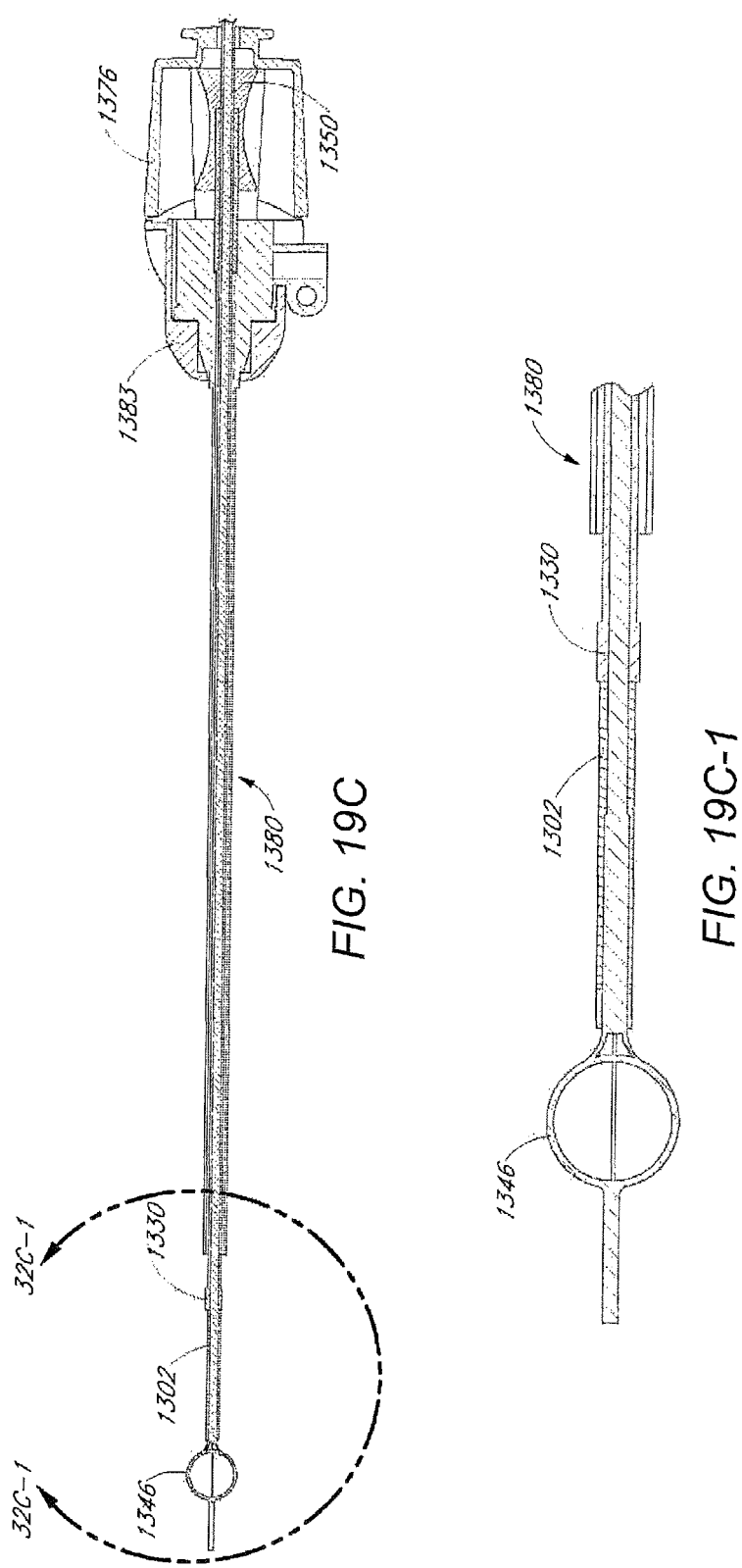

CHITOSAN AND POLYETHYLENE GLYCOL COPOLYMERS AND METHODS AND DEVICES FOR USING SAME FOR SEALING A VASCULAR PUNCTURE

CROSS-REFERENCE TO RELATED APPLICATIONS

This application claims priority to U.S. Provisional Patent Application No. 62/004,806 filed on May 29, 2014, titled "CHITOSAN AND POLYETHYLENE GLYCOL COPOLYMERS AND METHODS AND DEVICES FOR USING SAME FOR SEALING A VASCULAR PUNCTURE".

FIELD

Several embodiments of the inventions disclosed herein relate generally to sealants, apparatus, and methods for sealing punctures in a body. Some embodiments relate to copolymers that provide enhanced sealing effects. In several embodiments, apparatus and methods are disclosed that employ such copolymers for sealing a vascular puncture extending through tissue to a blood vessel.

BACKGROUND

Apparatus and methods are known for accessing a patient's vasculature percutaneously, e.g., to perform a procedure within the vasculature, and for sealing the puncture that results after completing the procedure. For example, a hollow needle may be inserted through a patient's skin and overlying tissue into a blood vessel. A guide wire may be passed through the needle lumen into the blood vessel, whereupon the needle may be removed. An introducer, procedural, or femoral sheath may then be advanced over the guide wire into the vessel, e.g., in conjunction with or subsequent to one or more dilators. A catheter or other device may be advanced through the introducer sheath and over the guide wire into a position for performing a medical procedure. Thus, the introducer sheath may facilitate accessing and/or introducing various devices into the vessel, while minimizing trauma to the vessel wall and/or minimizing blood loss.

Wounds such as arteriotomies can arise in the blood vessel from these various medical procedures, especially for blood vessels acting as sites for catheter insertion during diagnostic and/or interventional catheterization. After such procedures have been completed, the arteriotomy that was created as an access point during the medical procedure needs to be closed.

Upon completing the procedure, the device(s) and introducer sheath may be removed, leaving a puncture extending between the skin and the vessel wall. To seal the puncture, external pressure may be applied to the overlying tissue, e.g., manually and/or using sandbags, until hemostasis occurs. This procedure, however, may be time consuming and expensive, requiring as much as an hour of a medical professional's time. It is also uncomfortable for the patient, and may require the patient to remain immobilized in the operating room, catheter lab, or holding area. In addition, a risk of hematoma exists from bleeding before hemostasis occurs.

Vascular closure devices can be used to achieve hemostasis (e.g., sealing) of small holes that are formed in a blood vessel (either artery or vein) as the result of an intravascular procedure (e.g., cannulation). Such procedures may be for diagnosis, drug delivery, therapy (e.g., stent placement or angioplasty) and the like. The procedures involve the formation of a small incision in the wall of a vessel to gain access to the intravascular space. This incision, the vascular puncture or arteriotomy, must be closed at the completion of the procedure. Rapid hemostasis at the vascular puncture is ideal, as it reduces patient complications, improves time to patient ambulation and time to hospital discharge.

For example, a mechanical based device can be utilized for vascular closure. A percutaneous surgical device can comprise a combination wound suturing and crimping and cutting device. The combined device may locate a vessel wound and pass suture through the vessel walls surrounding the wound. Then, the crimping and cutting portion may detach, the suturing portion may be removed, and the crimping and cutting portion may be located to the wound site to apply a fastener (e.g., a ferrule).

Another mechanical based device can have two components: a needle advancing apparatus slidable longitudinally along a catheter to advance needles into a tissue membrane, such as a blood vessel wall, around an opening in the membrane; and, a suture retrieval assembly insertable through the catheter beyond a distal side of the tissue membrane. The needle advancing apparatus advances suture through the tissue wall. The suture retrieval assembly grabs the suture on the distal side of the tissue membrane for extraction thereof through the opening in the tissue membrane.

Such mechanical approaches tend to require precise positioning within the tissue tract, typically provide point (instead of a continuum of tissue purchase) support, and lead to permanent foreign-body implants that interfere with subsequent catheterization at the same vascular site. Additionally, a purely mechanical support of the wound could lead to implanting substantially non-absorbable foreign material that provides only point-support to the wound lips. In addition, purely mechanical closures still can leave behind open micro-spaces, or small gaps, between the sutures that are not entirely closed.

Previously (and currently, in some cases), manual compression was the main method for closing the vascular puncture. This could involve extended periods of manual pressure, clamping, exogenous weights, etc., applied directly to the site of the vascular puncture. As hemostasis could take 20 to 60 minutes, patients often experienced discomfort, and extended periods of bed rest were required.

In addition to, or in place of manual compression, vascular closure devices were developed to reduce the time to achieve hemostasis. Some such devices used sutures or collagen plugs to seal the vascular puncture. However, many such devices result in an intravascular component being retained within the vessel, which can lead to future complications.

More recently biodegradable materials have been employed to seal the vascular puncture and, due to their dissolution over time, improve patient comfort and reduce complications. Because rapid hemostasis can improve patient outcome and reduce medical costs, further improvements in vascular sealants would be beneficial.

Though presently in use, many current sealant technologies facilitate hemostasis of a wound puncture by physically clogging the tissue tract. This physical occlusion replaces manual compression, but certain of such polymeric sealants have a relatively weak polymer network integrity, which can increase time to hemostasis.

Various biological approaches to vascular closure have been used such as a device and method that includes inserting a vessel plug or sealant into the incision or puncture until the distal end of the vessel plug is adjacent to the outer lumen of the blood vessel. The vessel plug is positioned so that it does not obstruct the flow of fluid through the blood vessel or target organ. The precise positioning of the vessel plug in the incision or puncture is accomplished through the use of a balloon catheter or a cylindrical insertion assembly having a proximal plunger member associated therewith. Another biological closure can deploy a collagen plug to seal the closure. In order to block the collagen from entering the vessel, a footplate is installed on the interior of the blood vessel. The footplate is held in place with a suture.

In one instance, a vascular closure device can include two synthetic polyethylene glycol ("PEG") polymer powders that are mixed with appropriate buffers and injected through a femoral sheath at an arteriotomy site, e.g., as disclosed in U.S. Pat. No. 7,316,704. Accordingly, apparatus and methods for sealing a puncture through tissue would be useful. In particular, improving the efficacy (e.g., speed and/efficiency) of sealing a puncture would be useful.

SUMMARY

Provided for herein, in several embodiments, are vascular sealants, apparatus, and methods for sealing vascular punctures, the vascular sealants comprising copolymers that provide enhanced sealing effects.

As such, several embodiments herein provide vascular sealants comprising copolymers that provide enhanced hemostasis. In some embodiments, this is due to supplementation of the physical occlusion of the vascular puncture by sealants that have hemostatic and/or procoagulative properties. In several embodiments, the sealants attract platelets and/or other coagulation promoting co-factors. In several embodiments, the copolymer sealants provide enhanced "grip" at the site of a vascular puncture, thereby improving the occlusion of the puncture, and even allow the use of the copolymer sealants on larger puncture sizes.

In several embodiments, the copolymer sealant comprises chitosan and one or more polyethylene glycol polymers that exhibits a more rapid hemostasis compared to sealants that comprise only chitosan or only polyethylene glycol polymer sealants. Chitosan is a natural biopolymer found in crustaceans with a wide range of applications in tissue engineering, tissue repair and wound healing. Chitosan can be produced by deacetylation of chitin, which is the structural element in the exoskeleton of crustaceans (e.g., crabs, shrimps, etc.). Variation in the degree of deacetylation (% DA) can result in varying functionality of the chitosan in different applications. Chitosan is also biodegradable, for example, by chitosanase, papain, cellulose, acid proteases, and the like. Chitosan can form hydrogels depending on the molecular weight, the degree of deacetylation and the pH. In addition, a variety of cross linkers can be utilized to cross-link chitosan polymer chains and result in the formation of hydrogels.

Chitosan has been known to have hemostatic properties, which are described, for example in U.S. Pat. No. 4,394,373 and U.S. Pat. No. 8,012,167. However, in several embodiments, the chitosan of the copolymer sealants disclosed herein, is not simply mixed with the other polymeric component (or components), but rather is bound (e.g., covalently or non-covalently) to the other component (or components) of the sealant. For example, in several embodiments, the copolymer sealant comprises chitosan covalently (or non-covalently) bound to two types of polyethylene glycol (PEG), PEG-amine and PEG-ester. Advantageously, this improves the structural integrity of the sealant when deployed, but also imparts pro-coagulant and hemostatic properties to the sealant that improve efficacy in sealing vascular punctures.

Several embodiments of the sealants disclosed herein comprise both polyethylene glycol and chitosan in the freeze dried polymer hydrogel (e.g., the sealant). Sealants comprising only PEG (with no chitosan incorporated) elicit hemostasis of a wound puncture essentially by clogging the tissue tract upon expansion of the hydrogel sealant in the presence of physiological fluids. Freeze dried hydrogel sealant containing only PEG would lack the hemostatic and pro-coagulative properties of chitosan that is included in the sealants disclosed herein and thus PEG-only sealants would result in slower and less efficient hemostasis.

On the other hand a freeze dried hydrogel sealant utilizing chitosan only (with no PEG components incorporated) would lack the porosity characteristics (size and number of pores) that partially cross-linked PEG hydrogels can create upon freeze drying. Such a hydrogel would lack the rapid swelling capability that PEG components impart. These hydrogels would have reduced capacity to absorb physiological fluids and swell and subsequently clog the tissue tract. In addition these hydrogels would have reduced capacity to rapidly absorb blood and indirectly boost the inherit capability of chitosan since less blood would be available for chitosan to promote clotting. This would result in a reduced capacity to promote hemostasis as compared to hydrogels that contain both polyethylene glycol and chitosan, such as those disclosed herein.

Thus, freeze dried hydrogels comprising both chitosan and polyethylene glycol advantageously, and unexpectedly, lead to faster hemostasis of wounds since they combine the swelling characteristics of the PEG moiety along with the hemostatic and pro-coagulative properties of chitosan. The absorbance of blood by the porous PEG components can supplement and enhance chitosans ability for clotting because more blood volume is available for chitosan per surface area. These chitosan-PEG hydrogels may therefore have application to larger wounds versus the limited applicability when the sealant is composed of only polyethylene glycol or only chitosan.

Therefore, there are provided, in several embodiments, sealants for sealing punctures in tissues. In one embodiment, there is provided a sealant for sealing a puncture through tissue, comprising an elongate first section having a proximal end, a distal end, and a cross-section sized for delivery into a puncture through tissue and a second section extending from the distal end of the first section, the first section comprising a hydrogel comprising chitosan bound to at least one polymer. In several embodiments, the first section is formed from a freeze-dried hydrogel and the first section is configured to expand when exposed to physiological fluid within a puncture. In several embodiments, upon exposure to an aqueous physiological fluid, the hydrogel expands and seals the puncture through the tissue. In several embodiments, the puncture is a vascular puncture.

Also provided, in several embodiments, is a sealant for sealing a puncture through tissue, comprising a first section formed from a freeze-dried hydrogel, the first section being configured to expand when exposed to physiological fluid within a puncture. In several embodiments, the first section comprises a hydrogel comprising chitosan bound to at least one polymer, and upon exposure to an aqueous physiological fluid, the hydrogel expands and seals the puncture through the tissue.

In several embodiments, the first section has an elongated shape with a proximal end, a distal end, and a cross-section sized for delivery into a puncture through tissue. In several embodiments, the chitosan comprises chitosan that is at least partially deacetylated. For example, in one embodiment, the chitosan has a degree of deacetylation of at least 60%. In additional embodiments, the degree of deacetylation is between about 40% to 50%, about 50% to about 60% about 60% to about 70% about 70% to about 80%, about 80% to about 90%, about 90% to about 95%, about 95% to about 99% (and overlapping ranges between those listed). Greater or lesser degrees of deacetylation are also used, in other embodiments.

In several embodiments, the chitosan has a molecular weight between about 10 kilodaltons and about 600 kilodaltons, including about 10 kilodaltons to about 50 kilodaltons, about 50 kilodaltons to about 100 kilodaltons, about 100 kilodaltons to about 200 kilodaltons, about 200 kilodaltons to about 300 kilodaltons, about 300 kilodaltons to about 400 kilodaltons, about 400 kilodaltons to about 500 kilodaltons, about 500 kilodaltons to about 600 kilodaltons, or any molecular weight between or including those values.

Depending on the embodiment, the chitosan can be of a varied type. For example, in several embodiments, the chitosan can be free chitosan, chitosan chloride, chitosan glutamate, chitosan acetate, chitosan dicarboxylic acid salts, chitosan adipate, chitosan succinate, or chitosan fumarate. In some embodiments, combinations of two or more forms of chitosan are used.

In several embodiments, the at least one polymer is a polyethylene glycol polymer chain. In some embodiments, the at least one polymer is a polyethylene glycol polymer chain with side group functionality. In several embodiments, the at least one polymer is an amine modified polyethylene glycol or an ester modified polyethylene glycol. Combinations of amine modified polyethylene glycols and ester modified polyethylene glycols can also be used, in several embodiments. In several embodiments, the chitosan is bound to the at least one polymer by a covalent bond. In additional embodiments, the chitosan is bound to the at least one polymer by a non-covalent bond. In one embodiment, the at least one polymer is cross-linked polyethylene glycol that is bound to the chitosan.

In several embodiments, the amount of chitosan is varied. For example, in several embodiments, the first section of the sealant comprises between about 0.1% and about 30% (by weight) chitosan. For example, in several embodiments the chitosan is present in an amount (by weight) between about 0.1% to about 1.0%, about 1.0% to about 5.0%, about 5.0% to about 10.0%, about 10.0% to about 15.0%, about 15.0% to about 20.0%, about 20.0% to about 25.0%, about 25.0% to about 30.0%, and any amount between or including those amounts. In one embodiment the first section comprises between about 0.5% and about 8% (by weight) chitosan. In one embodiment, the first section comprises between about 2% and about 4% (by weight) chitosan. In one embodiment, the first section comprises between about 4% and about 6% (by weight) chitosan. Greater or lesser amounts of chitosan are also used, in some embodiments.

In several embodiments, the at least one polymer comprises polyethylene glycol-amine (PEG-amine) and polyethylene glycol-ester (PEG-ester). In some embodiments, the PEG-amine and PEG-ester are present in a molar ratio of PEG-amine to PEG-ester between 4 to 1 and 1 to 4. In some embodiments, the PEG-amine and PEG-ester are present in a molar ratio of PEG-amine to PEG-ester between 2 to 1 and 1 to 2. In some embodiments, the PEG-amine and PEG-ester are present in a molar ratio of PEG-amine to PEG-ester between about 0.8 to about 1.2. In some embodiments, the PEG-amine and PEG-ester are present in a molar ratio of PEG-amine to PEG-ester between about 0.9 to about 1.

In several embodiments, the PEG-amine and PEG-ester are present in a ratio of equivalent active groups that ranges from about 0.1 to about 5. In some embodiments, the PEG-amine and PEG-ester are present in a ratio of equivalent active groups that ranges from about 0.5 to about 3. In some embodiments, the PEG-amine and PEG-ester are present in a ratio of equivalent active group sites that ranges from between about 0.5 to about 2.0. In some embodiments, the PEG-amine and PEG-ester are present in a ratio of equivalent active group sites that ranges from about 0.8 to about 1.2. In some embodiments, the PEG-amine and PEG-ester are present in a ratio of equivalent active group sites that ranges from about 0.9 to about 1.

In several embodiments, the at least one polymer comprises polyethylene glycol-ester (PEG-ester). In one embodiment, the PEG-ester can be present in an amount (by weight) between about 99.0% to about 1.0%, about 90.0% to about 10.0%, about 80.0% to about 20.0%, about 70.0% to about 30.0%, about 60.0% to about 40.0%, about 55.0% to about 45.0%, about 53.0% to about 47.0%, about 52.0% to about 48.0%, about 52.0% to about 50.0%, and any amount between or including those amounts.

In several embodiments, the at least one polymer comprises polyethylene glycol-amine (PEG-amine) and a mixture of polyethylene glycol-esters (PEG-esters). In some embodiments, the PEG-amine and PEG-ester mixture can be present in a molar ratio of PEG-amine to PEG-ester of between 4 to 1 and 1 to 4. In some embodiments, the PEG-amine and PEG-ester mixture can be present in a molar ratio of PEG-amine to PEG-ester between 2 to 1 and 1 to 2. In some embodiments, the PEG-amine and PEG-ester can be present in a molar ratio of PEG-amine to PEG-ester between about 0.8 to about 1.2. In some embodiments, the PEG-amine and PEG-ester can be present in a molar ratio of PEG-amine to PEG-ester between about 0.9 to about 1.

In several embodiments, the sealant can also include a second section. In some embodiments, the second section can extend from the distal end of the first section. In some such embodiments, the second section can be made up of non-cross-linked precursors. In some embodiments, the non-cross-linked precursors comprise polyethylene glycol-amine and/or polyethylene glycol-ester. Depending on the embodiments, the second section also optionally includes chitosan. For example, in one embodiment, the second section can be a mixture of non-cross-linked polyethylene glycols bound to the chitosan. In several embodiments, the second section (when chitosan is included) can include between about 0.1% and about 30% (by weight) chitosan. For example, the second section may, in some embodiments, include between about 0.1% and about 30% (by weight) chitosan, including about 0.1% to about 1%, about 1.0% to about 5.0%, about 5% to about 10.0%, about 10.0% to about 15.0%, about 15.0% to about 20.0%, about 20.0% to about 25.0%, about 25.0% to about 30.0%, and any amount between or including those amounts.

Also, in several embodiments, the second section may also include one or more reinforcement elements. In some embodiments, the reinforcement elements have hemostatic properties including but not limited to chitosan reinforcing fibers, chitosan mesh, chitosan particles, or combinations thereof.

In several embodiments, the chitosan mesh is configured as a helical coil within the second section. In several embodiments, the chitosan mesh (regardless of its conformation) includes cross-linked chitosan, wherein the cross-links were formed using genipin. In several embodiments, chitosan fibers are configured as a helical coil within the second section. In some such embodiments, the chitosan fibers are formed by electrospinning. In several embodiments, the chitosan can be in the form of particles that are incorporated into the second section. The chitosan particles can be incorporated, depending on the embodiment, in a random manner throughout the second section, in a substantially uniform manner throughout the second section, or a patterned manner throughout the second section. In additional embodiments, random, uniform, or patterned particle distribution can be used in different portions of the second section.

In several embodiments, the sealant can be configured to seal a vascular puncture, wherein the sealant expands after exposure to an aqueous physiological fluid, and wherein a second section of the sealant can have hemostatic and pro-coagulative properties. In several embodiments, the second section further comprises a pH adjusting agent. In several embodiments, the sealant further comprises a therapeutic agent. In several embodiments, the sealant is dimensioned with a first section having a length (e.g., between proximal and distal ends) of between about 1 and about 20 millimeters. In several embodiments including a second section, the second section has a length of between about 0.5 and about 5 millimeters.

In several embodiments having both first and second sections, the first and second sections can have a substantially uniform outer cross-section along their lengths between about 1 and about 8 millimeters. Upon exposure to an aqueous physiological fluid, the sealants are configured to expand. In some embodiments, the first section (and second section, if included) is configured to expand in the dimension of the outer cross section of the sealant of at least 15%, including at least 20%, at least 25%, at least 30%, at least 40%, or at least 50%.

There are also provided herein methods for sealing a vascular puncture comprising applying a sealant as described herein to the vascular puncture.

In several embodiments, therefore, there are provided sealants and associated methods for sealing a puncture in a body. More particularly, several embodiments are directed to sealants made from chitosan and polyethylene glycol for sealing a puncture through tissue, and to methods for making such sealants. In addition, several embodiments of the invention are directed to sealants and methods for providing temporary or permanent hemostasis within a puncture extending through tissue.

In accordance with one embodiment, a sealant is provided for sealing a puncture through tissue that includes a first section including a proximal end, a distal end, and a cross-section sized for delivery into a puncture through tissue, and a second section fused to and extending from the distal end of the first section. In several embodiments, the first section is formed from a freeze-dried hydrogel made of chitosan and polyethylene glycol polymer chains and/or crosslinks that expands when exposed to physiological fluid within a puncture. In several embodiments, the second section is formed from a solid mass of non-freeze-dried, non-cross-linked hydrogel precursors, the precursors remaining in an unreactive state until exposed to an aqueous physiological environment, whereupon the precursors undergo in-situ cross-linking with one another to provide an improved adhesion of the sealant to the arteriotomy.

In one embodiment, the first section may consist essentially of freeze-dried hydrogel, and the second section may consist essentially of the non-cross-linked precursors. Alternatively, the second section may include one or more reinforcement elements with hemostatic properties, e.g., chitosan reinforcing fibers, a chitosan mesh or chitosan particles. In addition or alternatively, the second section may include one or more diluents to enhance one or more properties of the second section.

In another embodiment, the sealant includes only one section of a freeze-dried hydrogel made of chitosan and polyethylene glycol polymer chains and/or crosslinks that expands when exposed to physiological fluid within a puncture.

Optionally, the sealant may include one or more pH adjusting agents, e.g., impregnated into, coated over, or otherwise included in the first and/or second sections. For example, when the sealant is exposed within a puncture, the agent(s) may alter the localized pH on or around the sealant, e.g., to enhance cross-linking of the precursors and/or creation of a desired adhesive material. Alternatively, the materials for the precursors may be selected such that the pH and/or buffering capacity of interstitial body fluids and/or blood are effective to drive or otherwise facilitate cross-linking of the precursors. In such embodiments, the pH adjusting agents may be omitted.

In several embodiments, the first section of the sealant may be composed of a freeze-dried hydrogel that contains polyethylene glycol chains covalently bonded with chitosan polymer chains that has hemostatic and pro-coagulative properties and that expands when exposed to physiological fluids within a puncture. A solid mass of non-cross-linked hydrogel precursors such as polyethylene glycol with ester end groups, polyethylene glycol with amine end groups and chitosan with various degrees of deacetylation, may be fused or otherwise attached onto the distal end of the sealant. Until such time that the precursors are exposed to an aqueous physiological environment, the precursors remain in an unreactive state. At such time, the precursors undergo in-situ crosslinking with one another to provide an improved adhesion to the arteriotomy.

In an additional embodiment, chitosan fibers, chitosan mesh or chitosan particles may be incorporated or fused together with the non-cross-linked hydrogel precursors. For example, the solid mass may be formed as a substantially uniform solid plug or may be formed as a sintered mass of powder and fibers or mesh. The chitosan fibers, mesh or particles may act as a reinforcement element to increase the integrity of the cross-linked network. The melted precursors, which may or may not comprise chitosan fibers, chitosan mesh or chitosan particles may be applied to the distal end of the tubular roll within the tubular member, and allowed to solidify to create the solid mass fused to the distal end of the tubular roll.

In accordance with one embodiment, a sealant is provided for sealing a puncture through tissue that includes a first section including a proximal end, a distal end, and a cross-section sized for delivery into a puncture through tissue, and a second section fused to and extending from the distal end of the first section. The first section may be formed from a freeze-dried hydrogel that expands when exposed to physiological fluid within a puncture. The second section may be formed from a solid mass of non-freeze-dried, non-cross-linked hydrogel precursors, the precursors remaining in an unreactive state until exposed to an aqueous physiological fluid, whereupon the precursors undergo in-situ crosslinking with one another to provide an improved adhesion of the sealant to the arteriotomy.

In one embodiment, the first section may consist essentially of freeze-dried hydrogel, and the second section may consist essentially of the non-cross-linked precursors. Alternatively, the second section may include one or more reinforcement elements, e.g., a plurality of filaments or particles, mixed with, embedded in, or surrounding the precursors. In addition or alternatively, the second section may include one or more diluents to enhance one or more properties of the second section. As discussed above, the sealant may (or may not) include one or more pH adjusting agents, e.g., impregnated into, coated over, or otherwise included in the first and/or second sections.

In another embodiment, a sealant is provided for sealing percutaneous vascular large bore punctures, the sealant includes a first section including a proximal end, a distal end, and a cross-section sized for transcatheter delivery into the tissue tract and further including chitosan, and can optionally include a second section fused to and extending from the distal end of the first section. The large bore punctures can be sealed with a sealant that is initially sized the same as or larger than the large bore puncture or, alternatively, can be sealed with a sealant that is initially sized smaller than the large bore puncture by being loaded onto a small bore delivery device. It is understood that the physical properties of the sealant are such that it expands to occupy the full space of the device it is loaded upon, such that the same size sealant can be loaded onto a large bore delivery device as well as a small bore delivery device, just that upon being loaded onto a small bore delivery device the sealant would be compressed to fit into the smaller space. Large bore punctures can be arterial punctures that are sized from about 7 French to about 24 French. It is typically understood that small bore punctures can be arterial punctures sized up to about 7 Fr.

BRIEF DESCRIPTION OF THE DRAWINGS

It will be appreciated that the drawings are not necessarily drawn to scale, with emphasis instead being placed on illustrating the various aspects and features of the illustrated embodiments.

FIG. 2A shows as chitosan mesh, while FIG. 2B shows chitosan particles.

FIG. 4A-4F illustrate a method of delivering a sealant to an arteriotomy site.

FIGS. 5A, 5A-1, 5B, and 5B-1 illustrate a mechanism for controlling fluid flow through an inflation line.

FIGS. 6A, 6A-1, 6B, and 6B-1 illustrate another mechanism for controlling fluid flow through an inflation line.

FIGS. 6C-6D illustrate yet another mechanism for controlling fluid flow through an inflation line.

FIGS. 6E-6F illustrate yet another mechanism for controlling fluid flow through an inflation line.

FIGS. 7A, 7A-1, 7B, and 7B-1 illustrate yet another mechanism for controlling fluid flow through an inflation line.

FIGS. 9A-9B illustrate another mechanism for controlling movement of an outer housing relative to an inner housing.

FIGS. 15A-15F illustrate another method for delivering a sealant to an arteriotomy site.

FIGS. 16A-16B illustrate an apparatus for delivering a sealant to an arteriotomy including an inflation indicator.

FIGS. 17A-17D illustrate an embodiment of a dilator configured to engage a sheath.

FIGS. 18A-18C illustrate another embodiment of a dilator configured to engage a sheath.

FIGS. 19A-19D-1 illustrate a mechanism for engaging a positioning assembly and a sheath.

DETAILED DESCRIPTION

The apparatus, sealant and method disclosed herein capitalize on the interactions between chitosan and PEG moieties (e.g., PEG-amine and PEG-ester) to achieve enhanced hemostatic and procoagulative properties with improved integrity of the cross-linked sealant (both the grip and the freeze dried portion) after activation by physiological fluids. Chitosan can be covalently or non-covalently bonded, depending on the embodiment, with PEG to create the sealants. In addition, various cross linkers (e.g., genipin) can be used to crosslink chitosan polymer chains to create high molecular weight hydrogels of pure chitosan. The hydrogels can then be dehydrated by freeze drying to make a porous mesh that can be incorporated in the second section (the "grip" section) of a sealant to improve the integrity and stability of the final cross-linked network (after contact with physiological fluids).

Sealants

Figure 1:
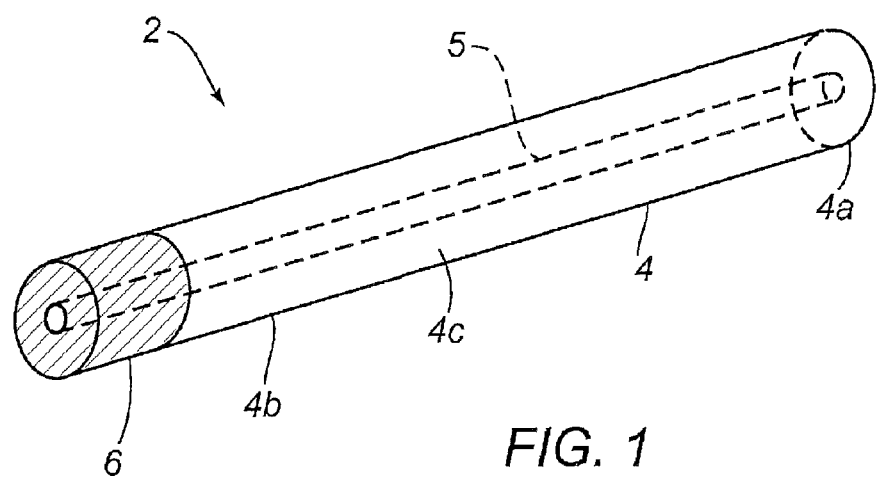
FIG. 1 is a perspective view of an exemplary embodiment of a sealant member comprising a freeze-dried hydrogel made of chitosan and polyethylene glycol polymer chains and/or crosslinks that expands when exposed to physiological fluid within a puncture.

FIG. 1 shows a non-limiting embodiment of a sealant 2 for sealing a puncture extending through tissue (not shown), such as a blood vessel. Generally, the sealant 2 can include a first, proximal, or main section 4 including proximal and distal ends 4a, 4b, and a second, distal, or tip section 6 formed from a plurality of non-freeze-dried and/or non-cross-linked precursors, e.g., formed as a solid mass or solid plug, fused or otherwise attached to and extending distally from the distal end 4b of the first section 4. As described further below, the non-cross-linked precursors may remain in an unreactive state, e.g., before or until exposure to an aqueous physiological environment, e.g., when deployed or otherwise exposed within a puncture extending through tissue.

For example, this configuration of sealant 2 may combine crosslinking of the second section 6 to create an adhesive material in-situ with swell characteristics and pro-coagulative properties of a freeze-dried hydrogel or other expandable material of the first section 4. By incorporating chitosan into a polyethylene glycol polymer network, the overall freeze dried hydrogel results in unexpectedly enhanced extra-vascular closure by providing expansion of the freeze dried hydrogel within the tissue tract upon contact with physiological fluid and providing hemostatic and pro-coagulative properties that, in combination, result in faster overall hemostasis of the vessel.

In one embodiment, the first section 4 can be formed from a sheet of freeze-dried hydrogel rolled into a tubular shape. It will be appreciated that the first section 4 may have other tubular or solid rod cross-sections or shapes, as desired, such as elliptical, triangular, square, conical, disk, polygonal shapes, and the like (not shown).

The first section 4 can be formed from a freeze-dried and cross-linked hydrogel that comprises two components, one being polyethylene glycol ("PEG") and the other component being chitosan. The two polymers, PEG and chitosan may be covalently bonded or blended together to form a freeze dried polymer hydrogel that expands upon contact with physiological fluids and that has hemostatic properties. Non-covalent bonding may also be used, in several embodiments. Optionally, a transition zone (not shown) may be included where the material of the second section 6 can penetrate partially into the distal end 4b of the first section 4, e.g., during fusion, as described further below. Some such embodiments enhance the structural stability of the sealant, further enhancing hemostasis.

In several embodiments, the material of the first section 4 may be at least partially absorbed by the body over time, e.g., over a period of days, weeks, or months. Likewise, the material of the second section 6 may also be at least partially absorbed by the body over time, e.g., over a period of days, weeks, or months. Depending on the embodiment, the first section 4 and second section 6 can be made of the same material. In some embodiments, the composition of the first section 4 and the second section 6 can be adjusted to accommodate their relative roles in the hemostatic process and the eventual healing of the puncture. For example, in several embodiments, the rate of absorption of the second section 6 can be slower than that of the first section 4, thereby maintaining the sealant over the puncture for a longer period of time, thus allowing the underlying vessel time to heal. The rate of degradation (and thus the specific make-up of the sealant) can be selected based on the size of puncture, rate of blood flow (or interstitial fluid flow) or blood pressure at the puncture site, or the degree of mobility that the puncture site will experience (e.g., healing may take longer at a puncture site that experiences frequent forces from body motion).

The PEG/chitosan co-polymer sealant can comprise two portions PEG (one portion PEG-amine and one portion PEG-ester) to one portion chitosan. In several embodiments, the chitosan can be at least partially deacetylated. It should be noted that the term "portion", as used herein, does not necessary indicate a quantity or ratio of the various components. Rather, specific details about further aspects of the sealants, including their specific compositions, are discussed below.

Polyethylene Glycol

The PEG used in the sealant can be varied, depending on the embodiment and factors such as the anticipated puncture size, the normal rate of blood flow in the area of the puncture, the physical status of a patient (e.g., on anticoagulant medication, etc.). In several embodiments, the PEG-amine portion may be a polymer such as 8A20K-NH2 (e.g., 8-arm 20 kilodalton (kDa) molecular weight, with amine terminated arms). In several embodiments, the PEG-ester portion may be a polymer such as 4A10K-CM-HBA-NHS (e.g., 4-arm, 10 kDa molecular weight, with carboxymethyl-hydroxybutyrate-N-hydroxysuccinimidyl functional groups on the arms). In another embodiment the PEG-ester portion may be a polymer such as 4A 10K-SS-NHS (e.g., 4-arm, 10 kDa molecular weight with succinimidyl succinate functional groups on the arms) or a polymer such as 4A10K-SG-NHS (e.g., 4-arm, 10 kDa molecular weight with succinimidyl glutarate functional groups on the arms) or a mixture of these polymers.

In various embodiments, different precursors may be used to manufacture both the first section 4 and the second section 6 of the sealant. For example, the precursors may comprise polyethylene glycol derivatives or polyethylene glycols with at least two end groups (e.g., 2 arms) and having at least one cross-linkable end group. The first functional group may chemically react with the second functional group in-situ to form covalent bonds and thereby form a cross-linkable gel. In some embodiments, the first functional group or second functional group can comprise strong electrophiles. For example, the first and/or second functional group may be one or more of epoxide, succinimide, N-hydroxysuccinimide, acrylate, methacrylate, maleimide, and N-hydroxysulfosuccinimide. Additionally, in some embodiments, the first and/or second functional group may be an amine group, a sulfhydryl group, a carboxyl group, and/or a hydroxyl group.

Depending on the embodiments, PEGs of various molecular weights may be used. As discussed above, the determination of molecular weight can be made based on the desired structural integrity that the sealant will need to possess, the rate of blood or fluid flow at the puncture site, the disappearance time and other clinical variables. In several embodiments, the molecular weight of the polyethylene glycols may range from about 2500 Daltons to about 50,000 Daltons. This includes polyethylene glycols with molecular weights ranging from about 2500 Daltons to about 5000 Daltons, about 5000 Daltons to about 10,000 Daltons, about 10,000 Daltons to about 15,000 Daltons, about 15,000 Daltons to about 20,000 Daltons, about 20,000 Daltons to about 25,000 Daltons, about 25,000 Daltons to about 30,000 Daltons, about 30,000 Daltons to about 35,000 Daltons, about 35,000 Daltons to about 40,000 Daltons, about 40,000 Daltons to about 45,000 Daltons, about 45,000 Daltons to about 50,000 Daltons, and any molecular weight between those listed.

Depending on the embodiments, the polyethylene glycols may have a varied number of functional groups. For example, in several embodiments, the polyethylene glycols may include two to eight functional groups, including three, four, five, six, or seven functional groups. Mixtures of polyethylene glycols with varied numbers of functional groups are also used in some embodiments.

Various derivatives of polyethylene glycol can also be used, depending on the embodiment. Non-limiting examples of the polyethylene glycol derivatives that may be used include, but are not limited to, branched polyethylene glycol derivatives, heterofunctional polyethylene glycol derivatives, linear monofunctional polyethylene glycol derivatives, and even combinations thereof. Non-limiting examples of branched polyethylene glycol derivatives include, but are not limited to, Y-Shape PEG NHS ester (molecular weight of ~40000 Da), Y-Shape PEG maleimide (molecular weight of ~40000 Da), Y-Shape PEG acetaldehyde (molecular weight of ~40000 Da), Y-Shape PEG propionaldehyde (molecular weight of ~40000 Da). Non-limiting examples of heterofunctional polyethylene glycol derivatives include, but are not limited to, hydroxyl PEG carboxyl (molecular weight of ~3500 Da), hydroxyl PEG amine, HCl Salt (molecular weight of ~3500 Da), amine PEG carboxyl, HCl Salt, (molecular weight of ~3500 Da), acrylate PEG NHS ester (molecular weight of ~3500 Da), maleimide PEG amine, TFA Salt (molecular weight of ~3500 Da), maleimide PEG NHS ester (molecular weight of ~3500 Da), 4-arm PEG succinimidyl succinate (pentaerythritol) (molecular weight of ~10000 Da), 8-arms PEG amine (molecular weight of ~10000-~20000 Da). Non-limiting examples of linear monofunctional polyethylene glycol derivatives include, but are not limited to methoxy PEG succinimidyl carboxymethyl ester, (molecular weight of ~10000-~20000 Da), methoxy PEG maleimide (molecular weight of ~10000-~20000 Da), methoxy PEG vinylsulfone (molecular weight of ~10000-~20000 Da), methoxy PEG thiol (molecular weight of ~10000-~20000 Da), methoxy PEG propionaldehyde (molecular weight of ~10000-~20000 Da), methoxy PEG amine, HCl Salt (molecular weight of ~10000-~20000 Da).

Chitosan

As discussed above, the copolymer sealant can comprise one portion chitosan. In several embodiments, the chitosan can be at least partially deacetylated. In one embodiment, the chitosan can be at least about 50% deacetylated. Chitosan that has a degree of deacetylation between about 60% and about 99% is used in several embodiments, including chitosan having a degree of deacetylation between about 60% and about 65%, between about 65% and about 70%, between about 70% and about 75%, between about 75% and about 80%, between about 80% and about 85%, between about 85% and about 90%, between about 90% and about 95%, between about 95% and about 96%, between about 96% and about 97%, between about 97% and about 98%, between about 98% and about 99%, and any degree of deacetylation between those values.

As with the PEG components, the chitosan can have a varied molecular weight, depending on the embodiment. While chitosan can have a varied molecular weight based on its production method, several embodiments of the sealant comprise chitosan having molecular weights between about 10 kilodaltons (kDa) and about 600 kDa. For example, in several embodiments, the chitosan component has a molecular weight of between about 10 kDa and about 50 kDa, between about 50 kDa and about 100 kDa, between about 100 kDa and about 150 kDa, between about 150 kDa and about 200 kDa, between about 200 kDa and about 250 kDa, between about 250 kDa and about 300 kDa, between about 300 kDa and about 350 kDa, between about 350 kDa and about 400 kDa, between about 400 kDa and about 500 kDa, between about 500 kDa and about 600 kDa, and any molecular weight between these ranges.

In one embodiment, the chitosan component comprises a chitosan having a molecular weight between 150 kDa and 400 kDa and a degree of deacetylation of at least 90%.

In another embodiment, the chitosan component comprises a chitosan having a molecular weight between 150 kDa and 400 kDa and a degree of deacetylation between 75% and 90%.

The chitosan precursors can optionally be in the free amine form or, alternatively in a salt form of chitosan. Suitable salts include, but are not limited to chitosan chloride, chitosan glutamate, chitosan acetate or other salt forms of chitosan. Mixtures of various salts and/or salts with the free amine form of chitosan may also be used.

PEG-Chitosan Ratios

As discussed above, in several embodiments, the sealant can comprise two portions PEG (e.g., PEG amine and PEG ester) and one portion chitosan. The molar ratio of the components can be varied, depending on the desired properties of the sealant (e.g., time to hemostasis, etc.). Depending on the embodiment, chitosan may be present in a molar ratio of chitosan to PEG of about 0.0001 to about 1.0. For example, the chitosan may be present in a molar ratio of chitosan to PEG of from about 0.0001 to about 0.0005, from about 0.0005 to about 0.001, from about 0.001 to about 0.005, from about 0.005 to about 0.01, from about 0.01 to about 0.05, from about 0.05 to about 0.1, from about 0.1 to about 0.2, from about 0.2 to about 0.3, from about 0.3 to about 0.4, from about 0.4 to about 0.5, from about 0.5 to about 0.6, from about 0.6 to about 0.7, from about 0.7 to about 0.8, from about 0.8 to about 0.9, from about 0.9 to about 1, or any ratios there between (and including endpoints).

Depending on the embodiment, the chitosan may also be present in the sealant composition based on a percentage of the sealant formulation (weight/weight, weight per volume, or volume/volume). For example, the chitosan may be present in a weight percentage in the entire formulation from about 0.1% to about 30%, such as about 0.1%, about 1%, about 3%, about 4%, about 5%, about 6%, about 10%, about 15%, about 20%, about 25%, or about 30% (or percentages between those listed). In several embodiments, the chitosan can be present in an amount from about 0.1% to about 30%, about 0.5% to about 25%, about 0.5% to about 15%, about 0.5% to about 10%, about 0.5% to about 8%, about 0.5% to about 6%, about 0.5% to about 4%, about 2% to about 4%, or any amount there between. In another embodiment, the first section comprises between about 4% and about 6% (by weight) chitosan. Greater or lesser amounts of chitosan can also be used. In still additional embodiments, the weight ratio of chitosan in the final hydrogel formulation is between about 1% and about 6% by weight of chitosan, including about 1% to about 2%, about 2% to about 3%, about 3% to about 4%, about 4% to about 5%, about 5% to about 6%, and percentages in between those listed (and including endpoints).

Depending on the embodiment, PEG-amine may be present in a molar ratio of PEG-amine to PEG-ester and chitosan of about 0.09 to about 9.9. For example, the PEG-amine may be present in a molar ratio of PEG-amine to the PEG-ester and chitosan of about 0.09 to about 0.1, about 0.1 to about 0.2, of about 0.2 to about 0.3, of about 0.3 to about 0.4, of about 0.4 to about 0.5, of about 0.5 to about 0.6, of about 0.6 to about 0.7, of about 0.7 to about 0.8, of about 0.8 to about 0.9, about 0.9 to about 1.0, about 1.0 to about 2.0, about 2.0 to about 3.0, about 3.0 to about 4.0, about 4.0 to about 5.0, about 5.0 to about 6.0, about 6.0 to about 7.0, about 7.0 to about 8.0, about 8.0 to about 9.0, about 9.0 to about 9.9, or any amount there between (and including endpoints).

Alternatively, PEG-amine may be present in the sealant composition based on a percentage of the sealant formulation (weight/weight, weight per volume, or volume/volume). For example, the PEG-amine may be present in a weight percentage in the entire formulation from about 99.0% to about 1.0%, about 90.0% to about 10.0%, about 80.0% to about 20.0%, about 70.0% to about 30.0%, about 60.0% to about 40.0%, about 55.0% to about 45.0%, about 53.0% to about 47.0%, about 52.0% to about 48.0%, about 50.0% to about 48.0%, and any percentage between or including those amounts.

Depending on the embodiment, PEG-ester may be present in a molar ratio of PEG-ester to PEG-amine and chitosan of about 0.09 to 19.9. For example, the PEG-ester may be present in a molar ratio of PEG-ester to PEG-amine and chitosan of about 0.09 to about 0.1, about 0.1 to about 0.2, of about 0.2 to about 0.3, of about 0.3 to about 0.4, of about 0.4 to about 0.5, of about 0.5 to about 0.6, of about 0.6 to about 0.7, of about 0.7 to about 0.8, of about 0.8 to about 0.9, about 0.9 to about 1.0, about 1.0 to about 2.0, about 2.0 to about 3.0, about 3.0 to about 4.0, about 4.0 to about 5.0, about 5.0 to about 6.0, about 6.0 to about 7.0, about 7.0 to about 8.0, about 8.0 to about 9.0, about 10 to about 11, about 11 to about 12, about 12 to about 13, about 13 to about 14, about 14 to about 15, about 15 to about 16, about 16 to about 17, about 17 to about 18, about 18 to about 19, 19 to about 19.9, or any amount there between.

Depending on the embodiment, PEG-ester may be present in the sealant composition based on a percentage of the sealant formulation (weight/weight, weight per volume, or volume/volume). For example, the PEG-ester may be present in a weight percentage in the entire formulation from about 99.0% to about 1.0%, about 90.0% to about 10.0%, about 80.0% to about 20.0%, about 70.0% to about 30.0%, about 60.0% to about 40.0%, about 55.0% to about 45.0%, about 53.0% to about 47.0%, about 52.0% to about 48.0%, about 52.0% to about 50.0%, and any percentage between or including those amounts.

In several embodiments, the molar ratio of chitosan to PEG-ester is between approximately 0.0001 to about 1. In another embodiment, the molar ratio of chitosan to PEG-ester is between approximately 0.0001 to about 0.005. In yet another embodiment the molar ratio of chitosan to PEG-ester is between approximately 0.005 to about 0.01. In several embodiments the equivalent ratio of active group sites of chitosan to the active group sites of PEG-ester is between approximately 0.01 to about 9. In another embodiment the equivalent ratio of active group sites of chitosan to the active group sites of PEG-ester is between approximately 0.01 to about 2. In another embodiment the equivalent ratio of active group sites of chitosan to the active group sites of PEG-ester is between approximately 0.1 to about 2. In another embodiment the equivalent ratio of active group sites of chitosan to the active group sites of PEG-ester is between approximately 0.5 to about 1.5.

As discussed above, in several embodiments a second section may be present and may consist essentially of the non-cross-linked precursors. In several embodiments, the second section can be formed from a solid mass of non-freeze-dried, non-cross-linked hydrogel precursors, the precursors remaining in an unreactive state until exposed to an aqueous physiological environment, whereupon the precursors undergo in-situ crosslinking with one another to provide an improved adhesion of the sealant to the arteriotomy. The hydrogel precursors may comprise polyethylene glycol with ester end groups, polyethylene glycol with amine end groups that are fused or otherwise attached onto the distal end of the sealant. Chitosan with various degrees of deacetylation may or may not be present in the second section. Chitosan's weight percentage in the second section may vary from 0.1% to 80%, if present. In another embodiment chitosan is present in the second section in a weight percentage between 1% and 30%. In yet another embodiment chitosan is present in the second section in a weight percentage between 10% and 30%. In an additional embodiment, chitosan fibers, chitosan mesh or chitosan particles may be incorporated or fused together with the non-cross-linked hydrogel precursors. For example, the solid mass may be formed as a substantially uniform solid plug or may be formed as a sintered mass of powder and fibers or mesh. The chitosan fibers, mesh or particles may act as a reinforcement element to increase the integrity of the cross-linked network. The melted precursors, which may or may not comprise chitosan fibers, chitosan mesh or chitosan particles may be applied to the distal end of the tubular roll within the tubular member, and allowed to solidify to create the solid mass fused to the distal end of the tubular roll.

While several embodiments relate to the use of chitosan-containing copolymers, the chitosan may also be used independently as a sealant to reduce the time to hemostasis. In such embodiments, the chitosan ranges from about 0.01% of the sealant to about 99.9% of the sealant.

Additional Agents

In additional embodiments, one or more additional compositions can be added to the co-polymer sealant. In several embodiments, the additional agents are added to the sealant to facilitate sealing of the puncture. In several embodiments, pro-thrombotic agents may be included in the sealant. For example, biological pro-thrombotics are included, in several embodiments. These include, but are not limited to, one or more of collagen, fibrin, fibrinogen, thrombin, Factor VIII, Factor IX, Factor X, calcium salts, carboxymethylcellulose, oxidized cellulose, alginates, gelatin, or other protein-based material. Synthetic materials that facilitate thrombosis may include polyglycolic acids (PGA's), polylactides (PLA's), polyvinyl alcohol (PVA), and the like.

In several embodiments, the first section 4 (and/or second section 6) may further include therapeutic and/or pharmaceutical agents, e.g., to promote healing, prevent infection and/or other adverse medical events, and the like.

For example, in several embodiments, the sealant may further comprise one or more drugs provided below, either alone or in combination. The drugs utilized may also be the equivalent of, derivatives of, or analogs of one or more of the drugs provided below. The drugs may include but are not limited to pharmaceutical agents including antimicrobial agents (e.g., antibiotic, antiviral, antiparasitic, antifungal agents), anti-inflammatory agents (including steroids or non-steroidal anti-inflammatory), biological agents including hormones, enzymes or enzyme-related components, antibodies or antibody-related components, oligonucleotides (including DNA, RNA, short-interfering RNA, antisense oligonucleotides, and the like), DNA/RNA vectors, viruses (either wild type or genetically modified) or viral vectors, peptides, proteins, enzymes, extracellular matrix components, and live cells configured to produce one or more biological components. The use of any particular drug is not limited to its primary effect or regulatory body-approved treatment indication or manner of use. Drugs also include compounds or other materials that reduce or treat one or more side effects of another drug or therapeutic agent. As many drugs have more than a single mode of action, the listing of any particular drug within any one therapeutic class below is only representative of one possible use of the drug and is not intended to limit the scope of its use with the ophthalmic implant system.

As discussed above, the therapeutic agents that are included in the sealant may be combined with any number of excipients as is known in the art. Excipients that are suitable for use include, but are not limited to, biodegradable polymeric excipients, benzyl alcohol, ethylcellulose, methylcellulose, hydroxymethylcellulose, cetyl alcohol, croscarmellose sodium, dextrans, dextrose, fructose, gelatin, glycerin, monoglycerides, diglycerides, kaolin, calcium chloride, lactose, lactose monohydrate, maltodextrins, polysorbates, pregelatinized starch, calcium stearate, magnesium stearate, silicon dioxide, cornstarch, talc, and the like. The one or more excipients may be included in total amounts as low as about 1%, 5%, or 10% and in other embodiments may be included in total amounts as high as about 50%, 70% or 90%.

Examples of drugs that may be used in the sealant may include various anti-secretory agents; antimitotics and other anti-proliferative agents, adrenergic antagonists, including for example, beta-blocker agents such as atenolol propranolol, metipranolol, betaxolol, carteolol, levobetaxolol, levobunolol and timolol; adrenergic agonists or sympathomimetic agents such as epinephrine, dipivefrin, clonidine, aparclonidine, and brimonidine; parasympathomimetics or cholingeric agonists such as pilocarpine, carbachol, phospholine iodine, and physostigmine, salicylate, acetylcholine chloride, eserine, diisopropyl fluorophosphate, demecarium bromide); muscarinics; carbonic anhydrase inhibitor agents, including topical and/or systemic agents, for example acetozolamide, brinzolamide, dorzolamide and methazolamide, ethoxzolamide, diamox, and dichlorphenamide; mydriatic-cycloplegic agents such as atropine, cyclopentolate, succinylcholine, homatropine, phenylephrine, scopolamine and tropicamide; prostaglandins such as prostaglandin F2 alpha, antiprostaglandins, prostaglandin precursors, or prostaglandin analog agents such as bimatoprost, latanoprost, travoprost and unoprostone.

Other examples of drugs that may be included in the sealant may also include anti-inflammatory agents including for example glucocorticoids and corticosteroids such as betamethasone, cortisone, dexamethasone, dexamethasone 21-phosphate, methylprednisolone, prednisolone 21-phosphate, prednisolone acetate, prednisolone, fluroometholone, loteprednol, medrysone, fluocinolone acetonide, triamcinolone acetonide, triamcinolone, triamcinolone acetonide, beclomethasone, budesonide, flunisolide, fluorometholone, fluticasone, hydrocortisone, hydrocortisone acetate, loteprednol, rimexolone and non-steroidal anti-inflammatory agents including, for example, diclofenac, flurbiprofen, ibuprofen, bromfenac, nepafenac, and ketorolac, salicylate, indomethacin, ibuprofen, naxopren, piroxicam and nabumetone; anti-infective or antimicrobial agents such as antibiotics including, for example, tetracycline, chlortetracycline, bacitracin, neomycin, polymyxin, gramicidin, cephalexin, oxytetracycline, chloramphenicol, rifampicin, ciprofloxacin, tobramycin, gentamycin, erythromycin, penicillin, sulfonamides, sulfadiazine, sulfacetamide, sulfamethizole, sulfisoxazole, nitrofurazone, sodium propionate, aminoglycosides such as gentamicin and tobramycin; fluoroquinolones such as ciprofloxacin, gatifloxacin, levofloxacin, moxifloxacin, norfloxacin, ofloxacin; bacitracin, erythromycin, fusidic acid, neomycin, polymyxin B, gramicidin, trimethoprim and sulfacetamide; antifungals such as amphotericin B and miconazole; antivirals such as idoxuridine trifluorothymidine, acyclovir, gancyclovir, interferon; antimicotics; immune-modulating agents such as antiallergenics, including, for example, sodium chromoglycate, antazoline, methapyriline, chlorpheniramine, cetrizine, pyrilamine, prophenpyridamine; anti-histamine agents such as azelastine, emedastine and levocabastine; immunological drugs (such as vaccines and immune stimulants); MAST cell stabilizer agents such as cromolyn sodium, ketotifen, lodoxamide, nedocrimil, olopatadine and pemirolastciliary body ablative agents, such as gentimicin and cidofovir; and other ophthalmic agents such as verteporfin, proparacaine, tetracaine, cyclosporine and pilocarpine; inhibitors of cell-surface glycoprotein receptors; decongestants such as phenylephrine, naphazoline, tetrahydrazoline; lipids or hypotensive lipids; dopaminergic agonists and/or antagonists such as quinpirole, fenoldopam, and ibopamine; vasospasm inhibitors; vasodilators; antihypertensive agents; angiotensin converting enzyme (ACE) inhibitors; angiotensin-1 receptor antagonists such as olmesartan; microtubule inhibitors; molecular motor (dynein and/or kinesin) inhibitors; actin cytoskeleton regulatory agents such as cyctchalasin, latrunculin, swinholide A, ethacrynic acid, H-7, and Rho-kinase (ROCK) inhibitors; remodeling inhibitors; modulators of the extracellular matrix such as tert-butylhydro-quinolone and AL-3037A; adenosine receptor agonists and/or antagonists such as N-6-cyclophexyladenosine and (R)-phenylisopropyladenosine; serotonin agonists; hormonal agents such as estrogens, estradiol, progestational hormones, progesterone, insulin, calcitonin, parathyroid hormone, peptide and vasopressin hypothalamus releasing factor; growth factor antagonists or growth factors, including, for example, epidermal growth factor, fibroblast growth factor, platelet derived growth factor or antagonists thereof, transforming growth factor beta, somatotrapin, fibronectin, connective tissue growth factor, bone morphogenic proteins (BMPs); cytokines such as interleukins, CD44, cochlin, and serum amyloids, such as serum amyloid A.

Other therapeutic agents may include neuroprotective agents such as lubezole, nimodipine and related compounds, and including blood flow enhancers such as dorzolamide or betaxolol; compounds that promote blood oxygenation such as erythropoeitin; sodium channels blockers; calcium channel blockers such as nilvadipine or lomerizine; glutamate inhibitors such as memantine nitromemantine, riluzole, dextromethorphan or agmatine; acetylcholinsterase inhibitors such as galantamine; hydroxylamines or derivatives thereof, such as the water soluble hydroxylamine derivative OT-440; synaptic modulators such as hydrogen sulfide compounds containing flavonoid glycosides and/or terpenoids, such as ginkgo biloba; neurotrophic factors such as glial cell-line derived neutrophic factor, brain derived neurotrophic factor; cytokines of the IL-6 family of proteins such as ciliary neurotrophic factor or leukemia inhibitory factor; compounds or factors that affect nitric oxide levels, such as nitric oxide, nitroglycerin, or nitric oxide synthase inhibitors; cannabinoid receptor agonists such as WIN55-212-2; free radical scavengers such as methoxypolyethylene glycol thioester (MPDTE) or methoxypolyethlene glycol thiol coupled with EDTA methyl triester (MPSEDE); anti-oxidants such as astaxathin, dithiolethione, vitamin E, or metallocorroles (e.g., iron, manganese or gallium corroles); compounds or factors involved in oxygen homeostasis such as neuroglobin or cytoglobin; inhibitors or factors that impact mitochondrial division or fission, such as Mdivi-1 (a selective inhibitor of dynamin related protein 1 (Drp1)); kinase inhibitors or modulators such as the Rho-kinase inhibitor H-1152 or the tyrosine kinase inhibitor AG1478; compounds or factors that affect integrin function, such as the Beta 1-integrin activating antibody HUTS-21; N-acyl-ethanaolamines and their precursors, N-acyl-ethanolamine phospholipids; stimulators of glucagon-like peptide 1 receptors (e.g., glucagon-like peptide 1); polyphenol containing compounds such as resveratrol; chelating compounds; apoptosis-related protease inhibitors; compounds that reduce new protein synthesis; radio-therapeutic agents; photodynamic therapy agents; gene therapy agents; genetic modulators; auto-immune modulators that prevent damage to nerves or portions of nerves (e.g., demyelination) such as glatimir; myelin inhibitors such as anti-NgR Blocking Protein, NgR (310)ecto-Fc; other immune modulators such as FK506 binding proteins (e.g., FKBP51).

Other therapeutic agents that may be used include: other beta-blocker agents such as acebutolol, atenolol, bisoprolol, carvedilol, asmolol, labetalol, nadolol, penbutolol, and pindolol; other corticosteroidal and non-steroidal anti-inflammatory agents such aspirin, betamethasone, cortisone, diflunisal, etodolac, fenoprofen, fludrocortisone, flurbiprofen, hydrocortisone, ibuprofen, indomethacine, ketoprofen, meclofenamate, mefenamic acid, meloxicam, methylprednisolone, nabumetone, naproxen, oxaprozin, prednisolone, prioxicam, salsalate, sulindac and tolmetin; COX-2 inhibitors like celecoxib, rofecoxib and. Valdecoxib; other immune-modulating agents such as aldesleukin, adalimumab (HUMIRA®), azathioprine, basiliximab, daclizumab, etanercept (ENBREL®), hydroxychloroquine, infliximab (REMICADE®), leflunomide, methotrexate, mycophenolate mofetil, and sulfasalazine; other anti-histamine agents such as loratadine, desloratadine, cetirizine, diphenhydramine, chlorpheniramine, dexchlorpheniramine, clemastine, cyproheptadine, fexofenadine, hydroxyzine and promethazine; other anti-infective agents such as aminoglycosides such as amikacin and streptomycin; antifungal agents such as amphotericin B, caspofungin, clotrimazole, fluconazole, itraconazole, ketoconazole, voriconazole, terbinafine and nystatin; anti-malarial agents such as chloroquine, atovaquone, mefloquine, primaquine, quinidine and quinine; anti-mycobacterium agents such as ethambutol, isoniazid, pyrazinamide, rifampin and rifabutin; antiparasitic agents such as albendazole, mebendazole, thiobendazole, metronidazole, pyrantel, atovaquone, iodoquinaol, ivermectin, paromycin, praziquantel, and trimatrexate; other anti-viral agents, including anti-CMV or anti-herpetic agents such as acyclovir, cidofovir, famciclovir, gangciclovir, valacyclovir, valganciclovir, vidarabine, trifluridine and foscarnet; protease inhibitors such as ritonavir, saquinavir, lopinavir, indinavir, atazanavir, amprenavir and nelfinavir; nucleotide/nucleoside/non-nucleoside reverse transcriptase inhibitors such as abacavir, ddI, 3TC, d4T, ddC, tenofovir and emtricitabine, delavirdine, efavirenz and nevirapine; other anti-viral agents such as interferons, ribavirin and trifluridiene; other anti-bacterial agents, including cabapenems like ertapenem, imipenem and meropenem; cephalosporins such as cefadroxil, cefazolin, cefdinir, cefditoren, cephalexin, cefaclor, cefepime, cefoperazone, cefotaxime, cefotetan, cefoxitin, cefpodoxime, cefprozil, ceftaxidime, ceftibuten, ceftizoxime, ceftriaxone, cefuroxime and loracarbef; other macrolides and ketolides such as azithromycin, clarithromycin, dirithromycin and telithromycin; penicillins (with and without clavulanate) including amoxicillin, ampicillin, pivampicillin, dicloxacillin, nafcillin, oxacillin, piperacillin, and ticarcillin; tetracyclines such as doxycycline, minocycline and tetracycline; other antibacterials such as aztreonam, chloramphenicol, clindamycin, linezolid, nitrofurantoin and vancomycin; alpha blocker agents such as doxazosin, prazosin and terazosin; calcium-channel blockers such as amlodipine, bepridil, diltiazem, felodipine, isradipine, nicardipine, nifedipine, nisoldipine and verapamil; other anti-hypertensive agents such as clo-nidine, diazoxide, fenoldopan, hydralazine, minoxidil, nitroprusside, phenoxybenzamine, epoprostenol, tolazoline, treprostinil and nitrate-based agents; prostaglandin PDE-5 inhibitors and other prostaglandin agents such as alprostadil, carboprost, sildenafil, tadalafil and vardenafil; anti-proliferative agents such as sirolimus, tacrolimus, everolimus, zotarolimus, paclitaxel and mycophenolic acid; hormonal-related agents including levothyroxine, fluoxymestrone, methyltestosterone, nandrolone, oxandrolone, testosterone, estradiol, estrone, estropipate, clomiphene, gonadotropins, hydroxyprogesterone, levonorgestrel, medroxyprogesterone, megestrol, mifepristone, norethindrone, oxytocin, progesterone, raloxifene and tamoxifen; anti-neoplastic agents, including alkylating agents such as carmustine lomustine, melphalan, cisplatin, fluorouracil 3, and procarbazine antibiotic-like agents such as bleomycin, daunorubicin, doxorubicin, idarubicin, mitomycin and plicamycin; anti proliferative agents (such as 1,3-cis retinoic acid, 5-fluorouracil, taxol, rapamycin, mitomycin C and cisplatin); antimetabolite agents such as cytarabine, fludarabine, hydroxyurea, mercaptopurine and 5-fluorouracil (5-FU); immune modulating agents such as aldesleukin, imatinib, rituximab and tositumomab; mitotic inhibitors docetaxel, etoposide, vinblastine and vincristine; radioactive agents such as strontium-89; and other anti-neoplastic agents such as irinotecan, topotecan and mitotane.

Optionally, the second section may further include one or more pH adjusting agents. For example, a pH adjusting agent, e.g., sodium borate, sodium phosphate, sodium bicarbonate, and/or other salts, such as $Na_2B_4O_7.10H_2O$ in crystalline or powder form, may be melted with the precursors (as discussed in more detail below) and then applied with the precursors to the distal end 4b of the first section 4. Alternatively, the pH adjusting agent may be applied to the second section 6 after fusing the melted precursors to the first section 4, e.g., by bonding or impregnating crystals of borate or other salts to the outer surface of the solid mass of non-cross-linked precursors and/or by melting and applying a coating of melted salts to the outer surface, e.g., similar to embodiments disclosed in the references incorporated by reference elsewhere herein. In addition or alternatively, one or more pH adjusting agents may be provided on the first section 4, if desired.

In this manner, the pH adjusting agent may alter the localized pH on or around the sealant 2, e.g., when deployed within a puncture to enhance cross-linking and/or creation of a desired adhesive material. Alternatively, the pH and/or buffering capacity of interstitial body fluids and/or blood may be effective to drive or facilitate cross-linking of the second section 6. For example, the precursors of the second section 6 may be optimized to take into account all of these factors and/or form a robust adherence to tissue.

In additional embodiments, other agents such as diluents, including but not limited to, low molecular PEG and/or glycerol, may be added to the sealant.

These additional agents may be embedded in the sealant, encased in the sealant (e.g., as a "core"), co-fabricated with the sealant, and/or applied as one or more coatings or layers. In addition, the material of the first section 4 may have a substantially uniform composition or the composition may be varied, e.g., along its length and/or within underlying layers within the first section 4.

Sealant Fabrication

In several embodiments, the first section 4 may be formed entirely from freeze-dried hydrogel, e.g., initially formed as a thin sheet of freeze-dried polymer. For example, to fabricate the first section 4 from blends of PEG and chitosan, PEG-amine, PEG-ester and chitosan powders intended to form the hydrogel may be filled into separate vessels (e.g., vials). Phosphate and borate buffers may be made, e.g., by dissolving the sodium borate and sodium phosphate in sterile water for injection (WFI) and adjusting the pH of each solution to meet pre-established requirements. The chitosan used may be in the form of chitosan salt (e.g. chitosan chloride, chitosan glutamate, chitosan acetate or other salt forms of chitosan). The chitosan salt powder may be mixed (or pre-mixed, depending on the embodiment) with the PEG-ester or PEG-amine powder in predetermined amounts. The powders may then be dissolved in their respective buffer solutions, e.g. in one vial the PEG-ester and chitosan in the phosphate buffer solution, and in the other vial PEG-amine in the borate buffer solution. Alternatively, the chitosan powder can be mixed with the PEG-amine in the borate buffer solution. Still alternatively, the chitosan powder can be mixed and dissolved in each of the vials, e.g., with both PEG-amine and PEG-ester, and then later combined. The molar ratio of the PEG-ester to PEG-amine may be such that the PEG-ester groups are in excess of PEG-amine so that PEG-ester groups are available to react with the amine groups of the chitosan polymer chains to create covalent bonding between the PEG and the chitosan polymer chains. Additional information on the ratio of the various PEG precursors is disclosed in more detail above. These precursor solutions may be mixed together, poured into trays, and freeze-dried. The freeze-dried material may optionally be subjected to a series of heat and/or humidity conditioning cycles, e.g., to complete the polymerization reaction.

In several embodiments, the freeze-dried and conditioned sheet of hydrogel sealant may then be trimmed according to size and mass requirements, e.g., cut to a desired length for the finished first section 4. For example, as shown in FIG. 1A, the trimmed hydrogel may be dried, rolled, and loaded into a transfer tube 8 for subsequent attachment to the second section 6.

To fabricate the non-freeze-dried, non-cross-linked distal section 6 of the sealant 2, PEG-amine and PEG-ester powders (or other cross-linkable polymer precursors) may be melted in an appropriate vessel (e.g., a beaker or flask), mixed, and heated at a pre-determined temperature and for a duration sufficient to fully melt and uniformly mix the mixture. One of ordinary skill in the art will appreciate that the melting point of the various precursors will depend, at least in part on their molecular weight. However, one of ordinary skill in the art will readily be able to, based on the disclosure provided herein, prepare the precursors appropriately to generate the co-polymer sealants. In another embodiment the non-freeze dried section may additionally contain chitosan fibers, a chitosan mesh or chitosan particles incorporated in the melted section. For example, the precursors may be melted in a substantially dry air or inert gas environment, e.g., a vacuum chamber. This approach can reduce entrapment of moisture, which may otherwise cause premature degradation and crosslinking. Using a vacuum generator, the melted PEG, which may or may not comprise chitosan fibers, chitosan mesh or chitosan particles, may then be applied onto the distal end 4b of the rolled freeze-dried first section 4.

Figure 1A:
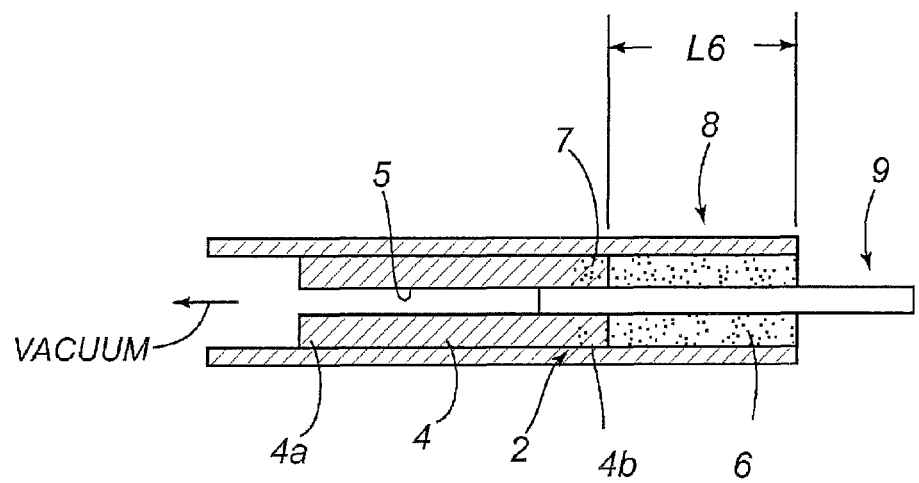
FIG. 1A is a cross-sectional view of a transfer tube and mandrel, showing a method for making the sealant member of FIG. 1.

For example, as described above, the first section 4 may be formed from a rolled sheet and loaded into a transfer tube 8, as shown in FIG. 1A. The transfer tube 8 may have an inner diameter or other cross-section corresponding to the desired outer diameter or cross-section for the finished sealant 2. The transfer tube 8 may be formed from any material sufficient to handle the processing parameters of the assembly process, such as polymers, metals, or composite materials, and may optionally include desired coatings, e.g., PTFE to facilitate insertion of the first section 4 and/or removal of the sealant 2.

The first section 4 may be loaded into the transfer tube 8 such that the distal end 4b of the first section 4 is offset inwardly a predetermined distance L6 from the end of the transfer tube 8, e.g., corresponding to or greater than the desired length of the second section 6. For example, for a desired finished length of the second section 6 of about 1.5 millimeters, the distal end 4b may be offset inwardly about two millimeters (2.0 mm) from the end of the transfer tube 8 (with any excess material may trimmed off later, as described below). Using the vacuum generator, the melted non-cross-linked PEG, which may or may not comprise chitosan fibers, chitosan mesh or chitosan particles, is then applied onto the distal end 4b of the rolled freeze-dried sealant, e.g., the vacuum directing the melted PEG into the transfer tube 8 and against the distal end 4b of the first section 4 (as represented by the arrow labeled "vacuum"). Thus, the transfer tube 8 may mold the melted PEG into the desired shape, e.g., diameter and/or length, for the second section 6.

The vacuum may cause the melted precursors to nominally abut the distal end 4b of the first section 4, and/or may partially draw the melted precursors into the pores and/or other open spaces within the first section 4, e.g., due to capillary action and the like. In this situation, a transition zone 7 may be created within the distal end 4b of the first section 4 in which the melted precursors permeate the freeze-dried hydrogel or other material of the first section 4, which may enhance fusing the second section 6 to the first section 4. For example, the melted precursors may quickly cool under ambient conditions such that the penetration into the distal end 4b may be relatively short, e.g., resulting in a transition zone 7 of less than a few millimeters (mm) (e.g., less than about five mm, less than about 4 mm, less than about 3 mm, less than about 2 mm, less than about one millimeter, or less).

The melted precursors may be dried under ambient conditions, e.g., simply allowed to cool and solidify, or alternatively, the melted and applied precursors may be exposed to desired conditions to accelerate or facilitate solidification of the melted precursors. The vacuum process effectively fuses the two sections together to provide a length of sealant 2.

Chitosan fibers may be manufactured by the technique of fiber spinning from solutions of chitosan in volatile solvents (e.g., electrospinning). A chitosan mesh may be manufactured by freeze drying a solution of high concentration of chitosan. Alternatively chitosan may be cross-linked by a variety of cross-linkers to create highly cross-linked chitosan polymer chains which may further be processed to manufacture chitosan fibers or a mesh. While in some embodiments, chemical cross-linking agents can be used (e.g., gluteraldehdye, formaldehyde), in several embodiments, natural cross-linkers such as genipin are used. Electrospinning methods can also be used to manufacture cross-linked chitosan fibers (e.g., fibrous mats or meshes). Vapor cross-linking may also be used, in several embodiments.

As discussed above, various ratios of PEG and chitosan can be used to provide a final freeze dried hydrogel that has high swelling capacity upon contact with physiological fluids as well as hemostatic properties. In several embodiments, two PEG precursors are combined with chitosan. In certain such embodiments, one PEG precursor contains ester end groups and one contains amine end groups. The PEG precursors can react with chitosan (the PEG ester can react with the amine groups of chitosan) and with each other (PEG-ester reacts with PEG-amine) and can provide a partially cross-linked network that upon freeze drying can result in a highly porous hydrogel material.

The ratio of PEG-ester to PEG-amine precursors as well as the ratio of the PEG precursors to the chitosan can alter final properties of the freeze dried hydrogel. As discussed above, the weight ratio of chitosan in the final hydrogel formulation can be between about 0.1 and about 30% wt, though in several embodiments, the weight ratio of chitosan in the final hydrogel formulation is between about 1% and about 10%. In one embodiment, the first section comprises between about 2% and about 4% (by weight) chitosan. In still additional embodiments, the final freeze dried hydrogel contains between about 4% and about 6% by weight of chitosan. The ratio of the PEG precursor that has ester active groups with regards to the PEG precursor that has amine end groups can impact the crosslinking density, porosity and integrity of the freeze dried polymer network. In some embodiments, the PEG-ester is in excess of the PEG-amine in order for some ester groups to be able to covalently react with the amine groups of the chitosan. These resulting hydrogels contain chitosan within their polymer network where chitosan is covalently bonded to the PEG components. This method increases the swelling capacity of the final freeze dried hydrogel material as well as the hemostatic ability by increasing the total surface area of the hydrogel material.

Figure 2A:
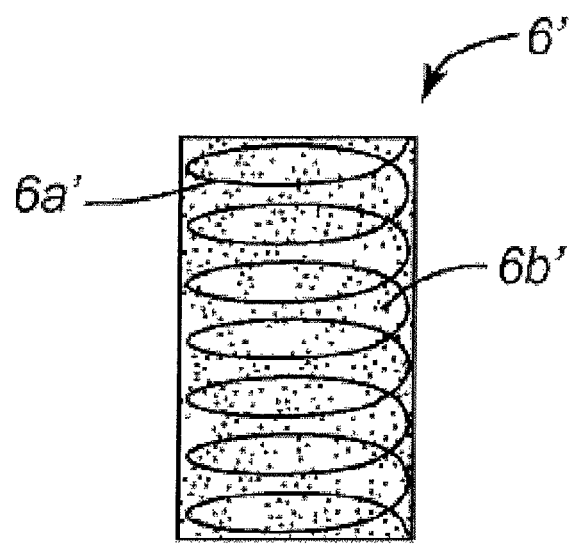
FIGS. 2A and 2B are side views of various embodiments in which chitosan is incorporated into a sealant.

As shown in FIG. 2A, a chitosan bioabsorbable mesh 6a' may be embedded within and/or surround the precursors 6b' of a second section 6'. The mesh 6a' of bioabsorbable chitosan may have greater rigidity, elasticity, and/or other desired properties than the solidified precursors 6b.' In addition, as shown, the mesh 6a' may include one or more fibers or filaments having a helical configuration (one helical filament shown), or alternatively the mesh 6a' may include a braid of filaments, a rolled porous mat, and the like (not shown). In one embodiment, the mesh 6a' may be embedded in the precursors 6b' of the second section 6,' e.g., by inserting the reinforcement element(s) into the end of the transfer tube 8 (not shown, see FIG. 1A) before applying the melted precursors (not shown), as described above. Thus, as the applied precursors are drawn into the transfer tube 8 and cool (or are otherwise dried and/or solidified), the precursors 6b' may permeate through and/or surround the mesh 6a,' thereby embedding the element(s) in the second section 6.'

Figure 2B:
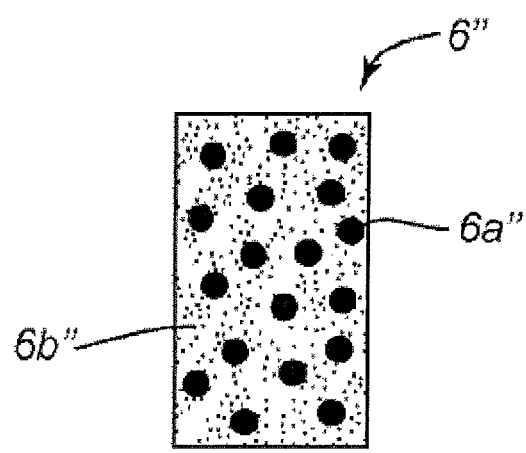

As shown in FIG. 2B, chitosan reinforcing particles or fillers 6a" may be provided in a second section 6". For example, compositions of chitosan may be mixed into the melted precursor mixture, and then the reinforcing fillers 6a" may be applied to the distal end 4b of the first section 4 (not shown) along with the precursors 6b," e.g., using the vacuum process described above. Thus, the filler material 6a" may be distributed randomly, substantially uniformly, or in a desired pattern throughout the second section 6," thereby enhancing the rigidity, reducing the brittleness, and/or otherwise modifying the properties of the precursors 6b" of the second section 6" in a desired manner.

As discussed above, diluents may be included in the formulation in some embodiments. In some such embodiments, the diluents are added to the formulation, (e.g., the melted precursors) before application to the first section 4, so as to improve the mechanical strength and/or integrity of the first section 6 and/or to minimize the brittleness of the second section 6.

It will be appreciated that the shape of any of the sealants herein may be modified to have a shape that is conducive to controlled deformation. Examples include an inverted golf tee, an hourglass, swept or wavy surfaces, tubular or solid rod cross-sections or shapes, elliptical, triangular, square, conical, disk, polygonal shapes, and the like (not shown).

As shown in FIG. 1, the first section 4 and the second section 6 (or alternatively section 6, if no first section 4 is included) may include a lumen 5 extending between the proximal and distal ends 4a, 4b of the first section 4 and through the second section 6, e.g., to facilitate delivery of the sealant 2. For example, the lumen 5 may be dimensioned to accommodate receiving a balloon catheter or other positioning member therethrough, e.g., such that the sealant 2 may slide relative to or pass over the positioning member and/or the positioning member may be directed axially relative to the sealant. Alternatively, the sealant 2 may be a substantially continuous rod of material, e.g., such that the sealant 2 may be delivered into a puncture using a cartridge or shuttle without a positioning member.

In addition (or alternatively), if the sealant 2 includes a lumen 5, the lumen 5 may be created when the first section 4 is formed, e.g., if the first section 4 is rolled from one or more sheets or layers of material or formed by molding. Alternatively, the lumen 5 may be formed by boring into or otherwise removing material from an already formed and solid first section 4, second section 6, or through the entire sealant 2. For example, if the first section 4 is formed from a rolled sheet, a rod or other mandrel 9 (which may be fabricated similar to the transfer tube 8) may be inserted through the lumen 5 before the second section 6 is applied to the distal end 4b, e.g., that extends from the transfer tube 8, as shown in FIG. 1A. Thus, the second section 6 may be molded and fused to distal end 4b around the mandrel 9, e.g., within the transfer tube 8. The mandrel 8 may be removed once the melted precursors have solidified, resulting in a continuous lumen through the second section 6 and the first section 4. Alternatively, the portion of the lumen 5 through the second section 6 may be bored, drilled, or otherwise created after the second section 6 is formed and fused to the first section 5.

The dimensions of the sealant can be tailored to the specific application (e.g., larger width and/or longer to seal larger punctures, or smaller/shorter for smaller punctures). In several embodiments, the sealant 2 has an overall length between about three and twenty millimeters (3-20 mm), including between about 3 and about 5 mm, between about 5 and about 7 mm, between about 7 and about 9 mm, between about 9 and about 11 mm, between about 11 and about 13 mm, between about 13 and about 15 mm, between about 15 and about 15.5 mm, between about 15.5 and about 16 mm, between about 16 and about 16.5 mm, between about 16.5 and about 17 mm, between about 17 and about 20 mm, or any length therebetween. Shorter or longer sealants may also be used, as is needed for specific sealing applications.

The second portion 6 of the sealant can be any percentage of the total length of the sealant. For example, while the non-limiting embodiment shown in FIG. 1 depicts a sealant with the first section 4 being substantially longer than the second section 6, it will be appreciated that, alternatively, the sections 4, 6 may have similar lengths, or the second section 6 may be longer than the first section 4. In a further alternative embodiment, the first section 4 may be omitted, and the second section 6 may provide the entire length of the sealant 2 (not shown), e.g., having a length between about three and twenty millimeters (3-20 mm).

For example, the first section 4 may have a length between about zero (if the sealant 2 is formed entirely from the second section 6) and twenty millimeters (0-20 mm), e.g., between about five and twenty millimeters (5-20 mm), e.g., about fifteen millimeters (15 mm). The second section 6 may have an outer diameter similar to the first section 4, but may have a length that is substantially shorter, e.g., between about zero (if the sealant 2 is formed entirely from the first section 4) and eight millimeters (0-8 mm), e.g., between about half and five millimeters (0.5-5.0 mm), e.g., about 1.5 millimeters.

Depending on the application the, outer diameter (or other cross-sectional dimension) of the sealant is between about one and about eight millimeters, including between about 1 mm to about 3 mm, about 3 mm to about 5 mm, about 5 to about 8 mm, and any diameter or dimension between those listed. For example, in several embodiments, the lateral dimension of the sealant is between about 1 and about 3 mm, including between about 1 mm and about 1.25 mm, between about 1.25 mm and about 1.5 mm, between about 1.5 mm and about 1.75 mm, between about 1.75 mm and about 2 mm, between about 2 mm and about 2.5 mm, between about 2.5 mm and about 3 mm, and any dimension between those listed. Sealants with larger or smaller lateral dimensions may also be used.

Devices for Sealant Deployment

Turning to FIGS. 3A-3D, an apparatus 710 is shown that generally includes a positioning member 714 and a cartridge 716 carried on the positioning member 714 for delivering a sealant 2 therein into a puncture (not shown). The cartridge 716 can include a sealant sleeve 750 carrying sealant 2 therein (which can include any of the sealant features described herein), and surrounding a distal end 734 of a support member 730 adjacent the sealant 2, and a handle or hub 723 on the proximal end 732 of the support member 730. The sealant sleeve 750 can include a relatively large diameter proximal portion 752 surrounding a portion of the distal end 734 of the support member 730, e.g., sized to abut or otherwise contact a hub or proximal end 783 of an introducer sheath 780, such as that shown in FIG. 3D, and a relatively small diameter distal portion 754 surrounding the sealant 2, e.g., sized to enter the hub 783 and/or lumen 786 of the introducer sheath 780. The hub 783 can include a cavity adapted to releasably receive the small diameter portion of the sealant sleeve. The cartridge 716 can be initially provided such that the sealant sleeve 750 and sealant 2 are located immediately adjacent a positioning element 746 of the positioning member 714.

The handle 723 can include an outer housing or shroud 772 surrounding an inner housing or frame 774 and one or more actuators 760-764 for allowing and/or causing movement of one or more components of the apparatus 710 relative to one another, as described further below. As shown, the outer housing 772 can include a first opening or slot 773 within which first and second actuators 760 and 762 are provided, and a second slot 775 within which third actuator 764 is provided. The opening 773 may include one or more features for interacting with first and/or second actuators 760, 762, as described further below.

The inner housing 774 may be slidable axially relative the outer housing 772, e.g., between an initial, proximal position and a distal position. For example, the outer housing 772 may include clam-shell halves or other components that may be attached around the inner housing 774 such that cooperating rails and grooves (not shown) allow the inner housing 774 to slide axially without substantial lateral motion. In an exemplary embodiment, one or more elongate ribs or rails (not shown) may be molded or otherwise provided on the inner surfaces of the outer housing 772 that may be slidably received between rails or grooves (also not shown) in the inner housing 774.

The handle 723 can include a distal shroud 776 integrally formed with or otherwise extending from the outer housing 772. One or more detents or other features, e.g., a pair of tines 778, may be provided on the shroud 776 for engaging the hub 723 to an introducer sheath, such as the sheath 780 shown in FIG. 3D. For example, the sheath 780 may include a hub 783 that includes a pair of pockets 783a that extend axially along opposite sides of the hub 783. The tines 778 include tabs or detents 778a that may be slidably received within the pockets 783a, e.g., when the apparatus 710 is introduced into the sheath 780 during use, as described below. The relative length of the tines 778 and pockets 783a are configured such that the detents 783a pass through the pockets 783a and extend out the distal ends thereof. The detents 783a may include ramped or tapered distal edges that facilitate insertion, and blunt proximal edges that may engage distal ends of the pockets 783a to prevent the tines 778 from being withdrawn back through the pockets 783a, thereby coupling movement of the sheath 780 and outer housing 772 of the hub 723, also as described further below.

Figure 3A:
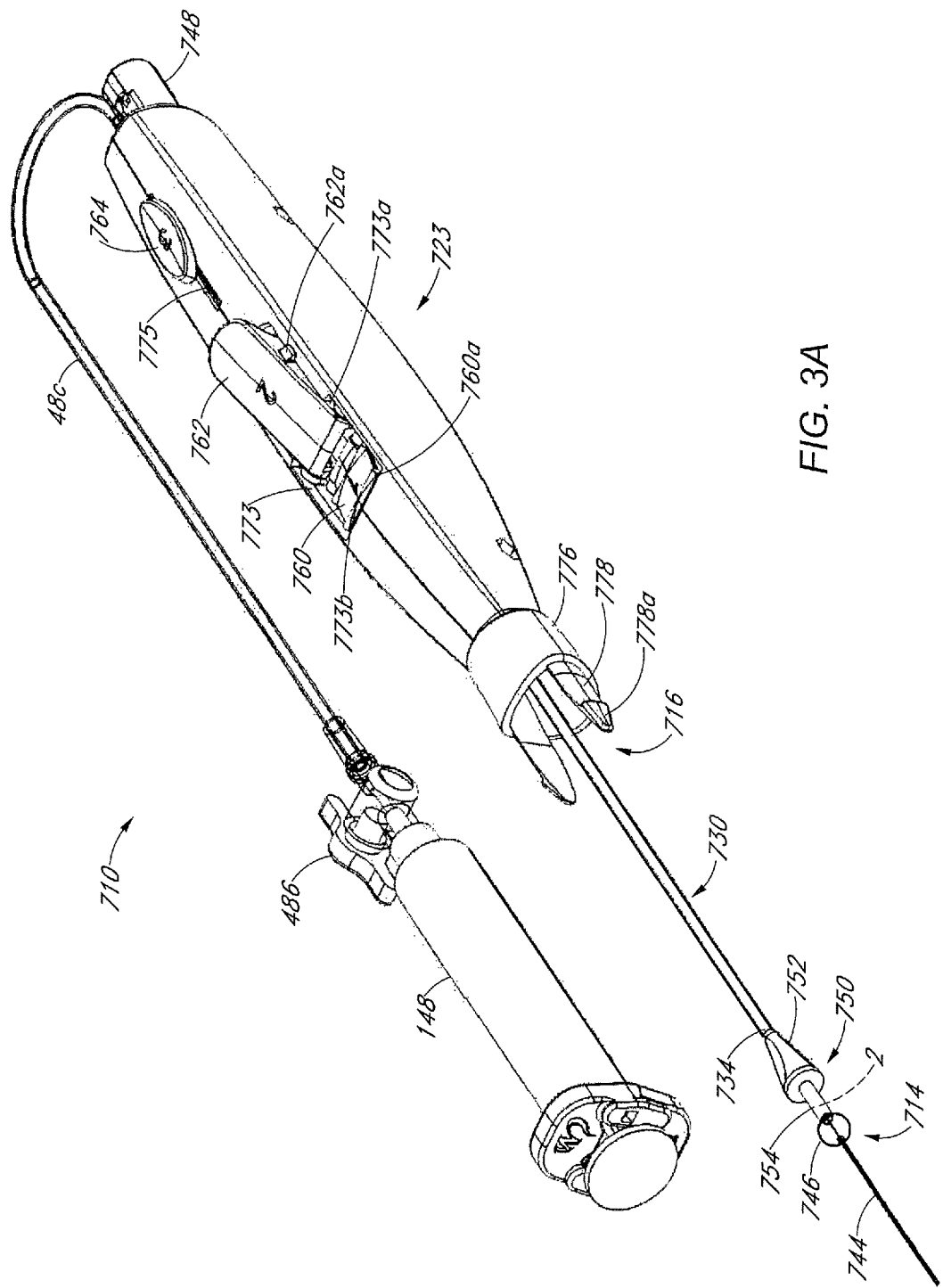
FIGS. 3A and 3B are perspective and side views, respectively, of another embodiment of an apparatus for delivering a sealant into a puncture through tissue.
Figure 3B:
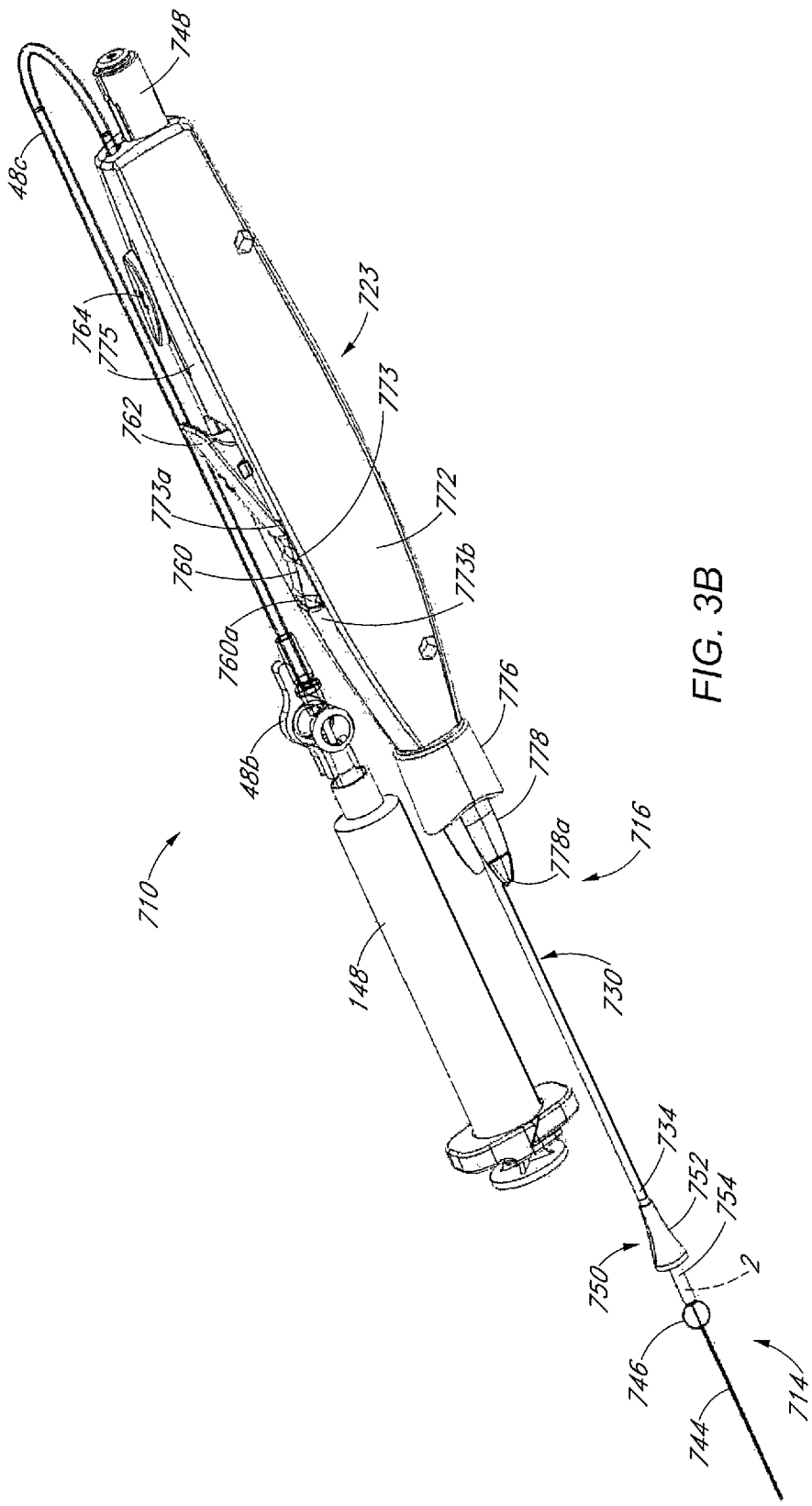
Figure 3C:
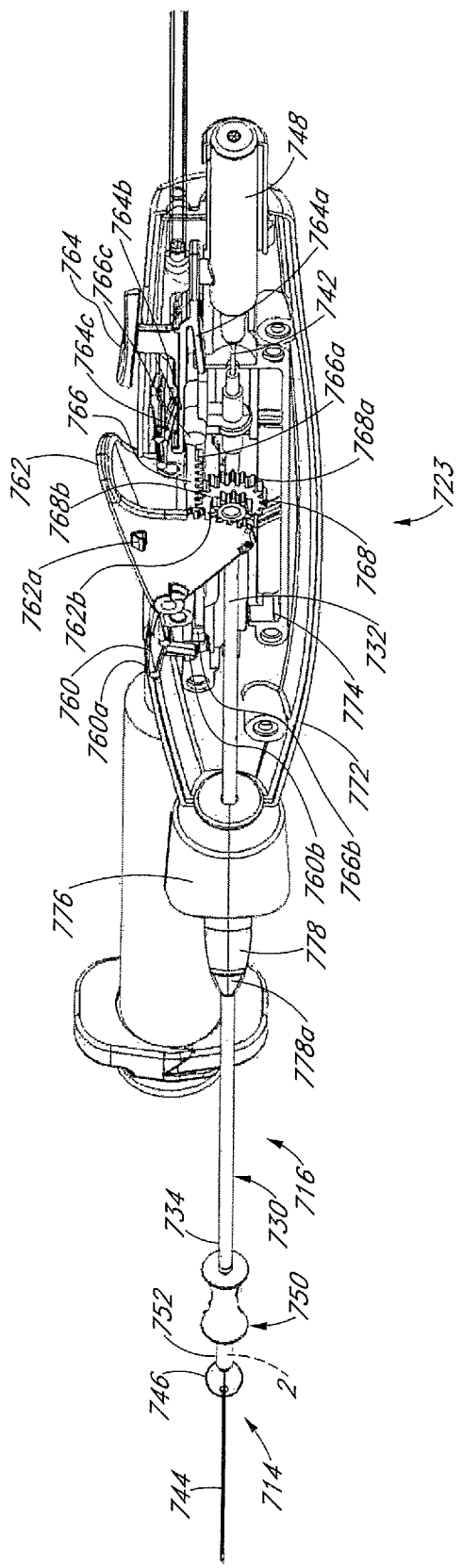
FIG. 3C is a side view of the apparatus of FIGS. 3A and 3B with a portion of an outer housing removed to show internal components of the apparatus.
Figure 3D:
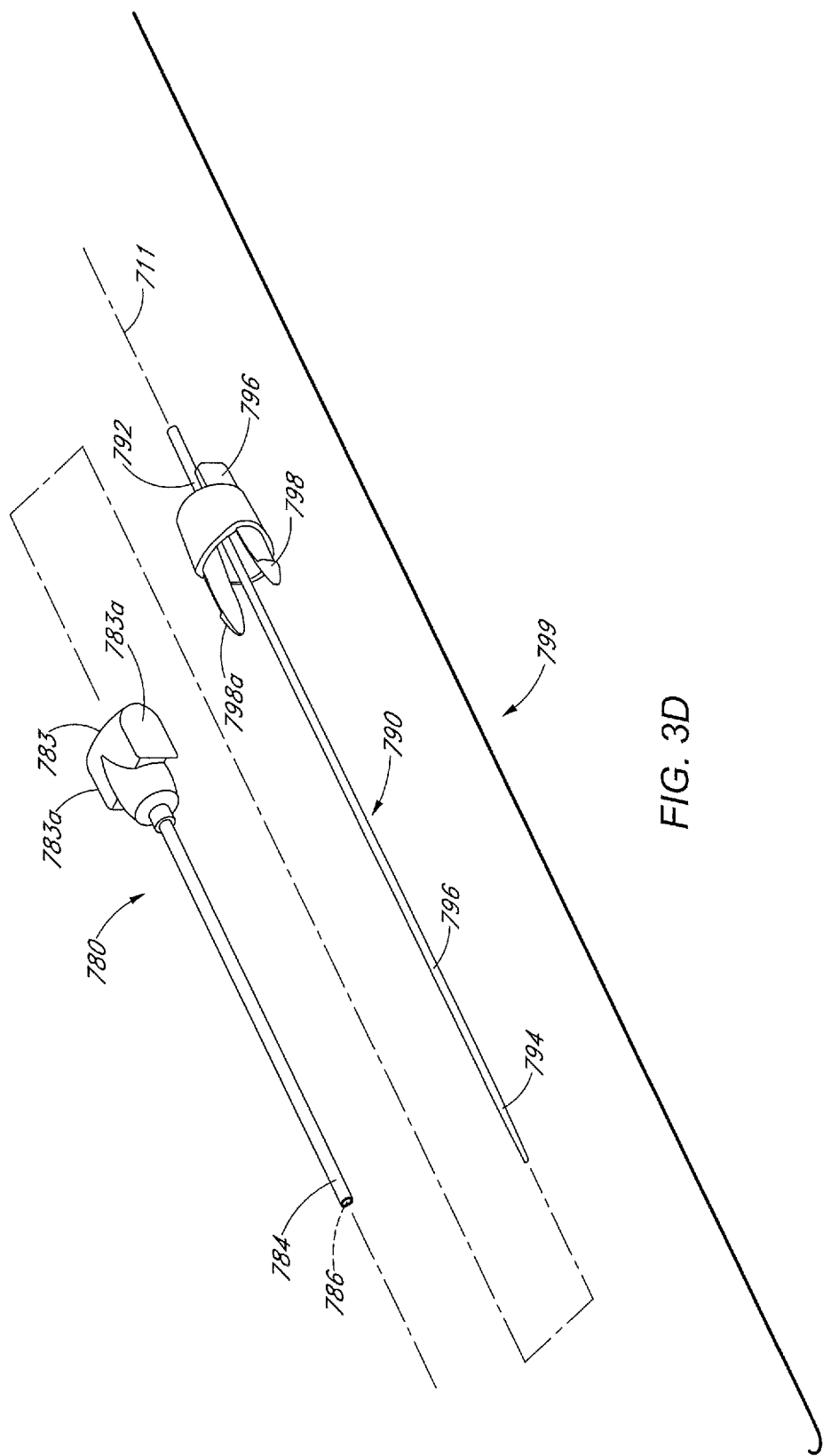
FIG. 3D is a perspective view of an introducer sheath and dilator assembly that may be used in cooperation with the apparatus of FIGS. 3A-3C.

As can be seen in FIG. 3C, the apparatus 710 can include a rack and pinion arrangement. For example, as shown, a rack 766 may be coupled to a proximal end 732 of the support member 730 and slidably received within the outer and/or inner housings 772, 774. A pinion 768 may be rotatably mounted to the inner housing 774 that is coupled to the rack 766 by a plurality of interlocking teeth 766a, 768a. The second or support actuator 762, e.g., a button pivotably coupled to the inner housing 774, is coupled to the pinion 768, e.g., by interlocking teeth 762b, 768b, for selectively rotating the pinion 768. For example, as described further below, the second actuator 762 may be depressed to cause the pinion 768 to rotate, thereby causing the rack 766 to advance distally, thereby advancing the support member 730.

Optionally, as shown, a first or locking actuator 760 may be provided on the hub 723 for preventing relative movement of the outer and inner/or housings 772, 774 until activated and/or limiting movement of the support member 730. For example, as best seen in FIG. 3C, the locking actuator 760 may be pivotably mounted to the inner housing 774 and include a distal end 760a that abuts or otherwise engages a distal edge 773b of the opening 773 in the outer housing 772. As a result, the inner housing 774 may be substantially secured in the proximal position and cannot be directed towards the distal position until the locking actuator 760 is activated to disengage the distal end 760a of the actuator 760 from the distal edge 773b of the opening 773.

In addition or alternatively, the first actuator 760 may include a detent or other locking feature 760b for selectively locking the support member 730 relative to the inner housing 774. For example, as shown in FIG. 3C, a detent 760b extends inwardly from the first actuator 760 that is not engaged with any other features. When the first actuator 760 is activated, i.e., directed inwardly to disengage the distal end 760a of the actuator 760 from the distal edge 773b of the outer housing 772, the detent 760b may drop downwardly into the inner housing 774. As discussed herein, once the inner and outer housing portions 774, 772 are movable relative to one another, the handle 723 can be moved proximally causing the outer sheath 780 to retract and uncover the sealant.

Subsequently, when the support actuator 762 is subsequently activated, the rack 766 may advance, causing the support member 730 to tamp the sealant toward the arteriotomy, as described herein, until a distal end 766b of the rack 766 passes under the detent 760b and the detent 760b is captured in a pocket (not shown) therein. With detent 760b captured in the pocket, the rack 766 cannot be directed proximally, thereby preventing proximal movement of the support member 730 coupled to the rack 766.

The apparatus 710 may also include a third or balloon retraction actuator 764, e.g., for selectively retracting the positioning element 746 through the sealant 2 after deployment. For example, as shown in FIG. 3C, the third actuator 764 may be slidably mounted to the inner housing 774 and may be selectively coupled to the hub 748 of the positioning member 714.

Initially, the third actuator 764 may be coupled with the inner housing 774 but may be decoupled from the inner housing 774 once the sealant 2 has been deployed and/or tamped. For example, as best seen in FIG. 3C, the third actuator 764 may include a third arm 764c that may be decoupled from the inner housing 774 such that proximal movement of the third actuator 764 relative to the outer and/or inner housings 772, 774 causes similar proximal movement of the hub 748, thereby directing the positioning element 746 proximally.

In addition, the third actuator 764 can include a second arm 764b that may be slidably positioned adjacent a proximal end 766c of the rack 766. With the second arm 764b positioned in this manner, the third arm 764c may remain coupled with the hub 748. When the rack 766 is directed distally, e.g., by activating the second actuator 762, the second arm 764b may slide off the proximal end 766c of the rack 766, thereby decoupling the third arm 764c from the inner housing 774. For example, as shown, a spring or other biasing mechanism 764a may be provided on the third actuator 764 (or optionally, the outer housing 772) for biasing the second arm 764b outwardly when the rack 766 is directed distally to clear the second arm 764b from the proximal end 766c of the rack 766. In addition, the spring or biasing mechanism 764a may require that the actuator be depressed in order to decouple the third arm 764c from the inner housing thereby preventing inadvertent movement of the positioning element 746. Thereafter, the third actuator 764 may be directed proximally to retract the hub 748 and the positioning element 746.

The apparatus 710 may be used to deliver the sealant 2 into a puncture, e.g., communicating with a body lumen within a patient's body. Initially, the introducer sheath 780 shown in FIG. 3D may be positioned through the puncture into the body lumen.

Optionally, the introducer sheath 780 may be provided as part of an introducer kit, e.g., including a dilator 790 and a guidewire 799, and/or a system also including the apparatus 710. The dilator 790 may include a proximal end 792 and a distal end 794 sized to be slidably received through the lumen 786 of the introducer sheath 780, e.g., terminating a tapered, atraumatic and/or other distal tip to facilitate introduction of the dilator 790 and introducer sheath 780 into a puncture (not shown), e.g., over the guidewire 799. As shown, the dilator 790 can include a proximal housing 796 include tines 798 and detents 798a configured similar to the distal shroud 776 of the apparatus 710. The dilator 790 may be directed into the hub 783 and lumen 786 of the introducer sheath 780 until the tines 798 enter and the detents 798a exit the passages 783a in the hub 783.

Thus, the dilator 790 and introducer sheath 780 may be coupled together such that the guidewire 799 (already placed through a puncture into a body lumen, not shown, as described elsewhere herein) may be backloaded into the distal end 794 and lumen 796 of the dilator 790 to introduce the dilator 790 and introducer sheath 780 into the puncture. Once the introducer sheath 780 is positioned as desired, the tines 798 may be squeezed inwardly to disengage the detents 798a from the pockets 783a and allow the dilator 790 to be withdrawn from the lumen 796 of the introducer sheath 790. The introducer sheath 780 may then be used to access the body lumen and perform one or more procedures, as described elsewhere herein.

When it is desired to seal the puncture, any instruments introduced through the introducer sheath 780 may be removed and the apparatus 710 may be prepared, e.g., as shown in FIGS. 3A and 3B. With the positioning element 746 collapsed, the distal end 744 of the positioning member 714 may be directed into the hub 783 of the introducer sheath 780, through the lumen 786, and into the body lumen. Because the sealant sleeve 750 and sealant 2 are located immediately adjacent the positioning element 746, as the distal end 744 enters the introducer sheath 780, the sleeve 750 may contact the introducer sheath 780, which may prevent further advancement of the sleeve 750. For example, the distal portion 754 of the sleeve 750 may at least partially enter the hub 783 of the introducer sheath 780 and the proximal portion 752 of the sleeve 750 may abut the hub 783, thereby preventing further advancement of the sleeve 750. If the sleeve 450 is releasably attached to the support member 730, advancement of the positioning member 714 may release the sleeve 750 from the distal end 734 of the support member 730.

The positioning member 714 may be advanced further into the introducer sheath 780, whereupon the sleeve 750 may remain substantially stationary relative to the introducer sheath 780 and, consequently, slide proximally over the support member 730. Thus, the distal end 734 of the support member 730 may exit the distal portion 754 of the sleeve 750 and enter the introducer sheath lumen 786, thereby ejecting the sealant 2 from the sleeve 750 and into the sheath lumen 786. Optionally, the distal portion 754 of the sleeve 750 may have sufficient length and/or other features to at least partially open the valve(s) (not shown) within the introducer sheath hub 783, e.g., to facilitate the sealant 2 and distal end 734 of the support member 730 being advanced into the introducer sheath lumen 786. Thus, the sleeve 750 may protect the sealant 2 until the sealant 2 passes through the hub 783 and any valves therein, into the lumen 786 of the introducer sheath 780.

The positioning member 714 may then be advanced until the positioning element 746 is disposed beyond the distal end 784 of the introducer sheath 780, i.e., within the body lumen. As this occurs, the tines 778 on the housing shroud 776 may be aligned with and enter the pockets 783a on the sheath hub 783, e.g., until the detents 778a engage the distal ends of the pockets 783a, as described above. With the detents 778a engaged with the pockets 783a, the introducer sheath 780 and outer housing 772 may be coupled together such that they move together.

The relative length of the positioning member 714 and the introducer sheath 780 may be configured such that the sealant 2 remains within the sheath lumen 786, e.g., proximal to the distal end 784 of the introducer sheath 780, while the positioning element 746 is exposed beyond the distal end 784. The positioning element 746 may then be expanded, e.g., by inflating the positioning element 746 using fluid from the syringe 148. The entire apparatus 710 and introducer sheath 780 may then be retracted (regardless of whether the apparatus hub 723 or the sheath hub 783 is manipulated) until the expanded positioning element 746 contacts the wall of the body lumen adjacent the puncture.

Once properly positioned, the first actuator 760 may be activated to decouple movement of the outer and inner members 772, 774. For example, while holding the outer housing 772, the first actuator 760 may be pressed inwardly to disengage the distal end 760a of the first actuator 760 from the distal end 773b of the outer housing 772, and then the outer housing 772 may be retracted proximally, i.e., away from the patient and puncture. With the inner housing 774 coupled to the positioning member 714 and support member 730, this action causes the inner housing 774 to slide within the outer housing 772, i.e., from the proximal position (shown in FIGS. 3A-3C) to the distal position, thereby retracting the introducer sheath 780 relative to the support member 730 and exposing the sealant 2 within the puncture adjacent the positioning element 746.

With the inner housing 774 in the distal position, the second actuator 762 may be activated to advance the support member 730, e.g., to tamp or compress the sealant 2 against the expanded positioning element 746 and/or outer wall of the body lumen, e.g., over an arteriotomy. For example, with particular reference to FIG. 3C, the second actuator 762 may be pressed inwardly, thereby rotating the pinion 768, advancing the rack 766, and consequently advancing the support member 730 to direct the distal end 734 towards the positioning element 746 and compress the sealant 2 therebetween.

Optionally, the second actuator 762 may include one or more features, e.g., tabs or detents 762a that may be engaged with the outer housing 772 when the second actuator 762 is fully depressed. For example, as shown in FIGS. 3A and 3B, the opening 773 in the outer housing 772 may include one or more pockets or recesses 773a that may be aligned with the tabs 762a on the second actuator 762 when the inner housing 774 has been directed fully to the distal position. With the tabs 762a received within the pockets 773a, the inner housing 774 cannot be moved proximally relative to the outer housing 772, thereby securing the outer and inner housings 772, 774 relative to one another.

Once the sealant 2 has been exposed for sufficient time and/or tamped by the support member 730, the positioning element 746 may be collapsed, and the positioning member 714 withdrawn from the body lumen, e.g., pulling the collapsed positioning element 746 through the sealant 2 and support member 730. For example, the positioning element 746 may be deflated using the syringe 148, and then the third actuator 764 may be activated to withdraw the collapsed positioning element 746 through the sealant 2 and into the distal end 734 of the support member 730.

Optionally, as described above, the third actuator 764 may remain coupled with the inner housing 774 until the rack 766 is advanced sufficiently to release the third arm 764c of the third actuator. Thereafter, proximal movement of the third actuator 764 relative to the outer and inner housings 772, 774 causes the hub 748 and the entire positioning member 714 to also move proximally, thereby withdrawing the positioning element 746 through the sealant 2 into the distal end 734 of the support member 730. The length of the slot 775 in the outer housing 772 may be configured to withdrawn the positioning element 746 a desired distance into the distal end 734.

Once the positioning element 746 is withdrawn through the sealant 2, the entire apparatus 710 may be withdrawn to remove the support member 730 from the puncture, leaving the sealant 2 within the puncture.

Figure 4A:
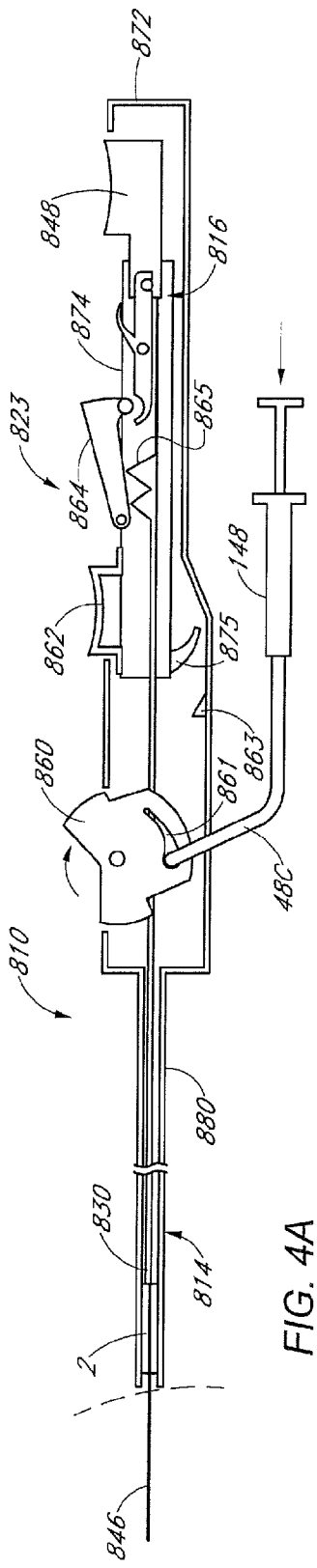
Figure 4B:
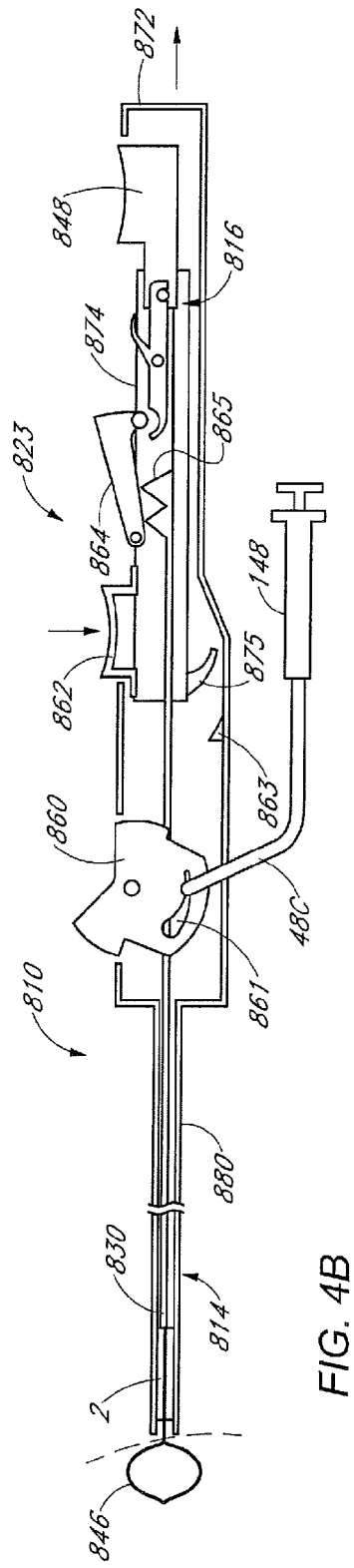

FIGS. 4A-4F schematically illustrate a method of delivering a sealant from another apparatus 810 to an arteriotomy site. The apparatus 810 can include any of the features described in connection with the apparatus 710. For example, the apparatus 810 can include a sealant 2 positioned at a distal portion of a positioning assembly 814. The positioning assembly 814 extends through the puncture and into the vessel, such that the positioning element 856 is within the vessel lumen and the sealant 2 is outside the vessel wall (FIG. 4A). Expanding the positioning element 846 secures the apparatus 810 relative to the arteriotomy site (FIG. 4B). Withdrawing a sheath 880 exposes the sealant 2 to the arteriotomy site (FIG. 4C), and advancing a support member 830 tamps the sealant 2 (FIG. 4D). After the positioning element 846 deflates (FIG. 4E), the positioning element 846 can move proximally through the sealant 2 (FIG. 4F), leaving the sealant 2 outside the vessel. The support member 830 can maintain the position of the sealant 2, while the positioning element 846 is withdrawn. After the positioning element 846 is withdrawn, the entire apparatus 810, including the sheath 880 and the positioning assembly 814 can be withdrawn from the patient. The apparatus 810 and methods of using the apparatus 810 are described in detail below.

As shown in FIGS. 4A through 4F, the apparatus 810 can include a handle 823. The handle 823 can include an outer housing 872 and an inner housing 874. The outer housing 872 can move relative to the inner housing 874, for example, when the sheath 880 moves proximally relative to the positioning assembly 814.

The handle 823 can include one or more actuators for controlling the apparatus 810. Each actuator can control one or more functions of the apparatus 810. The one or more actuators can be positioned anywhere along the handle 823. In FIGS. 4A through 4F, the actuators 860, 862, 864, and 848 are positioned along the handle 823 based on the procedural step each actuator controls. The configuration of actuators shown in FIGS. 4A through 4F reduces confusion associated with operating the apparatus 810 by only requiring the user to move his/her hand proximally for each subsequent step of the procedure. Although FIGS. 4A through 4E illustrate four actuators 860, 862, 864, and 848, fewer or additional actuators may be used to perform the same functions.

The apparatus 810 can include the inflation line 48c. The inflation line 48c is in fluid communication with the positioning element 846. The inflation line 48c connects to the syringe 148 or other device for delivering fluid to the positioning element 846.

The apparatus 810 can include a first actuator 860 to control fluid flow through the inflation line 48c. The first actuator 860 moves between an open position and a closed position. As shown in FIG. 4A, when the first actuator 860 is in the open position, the syringe 148 can deliver a fluid through the inflation line 48c to expand the positioning element 846. In FIG. 4B, the first actuator 860 moves to the closed position and restricts fluid flow through the inflation line 48c to maintain the expanded state of the positioning element 846. After the positioning element 846 expands, the apparatus 810 moves proximally so the positioning element 846 is adjacent to the arteriotomy.

Figure 4C:
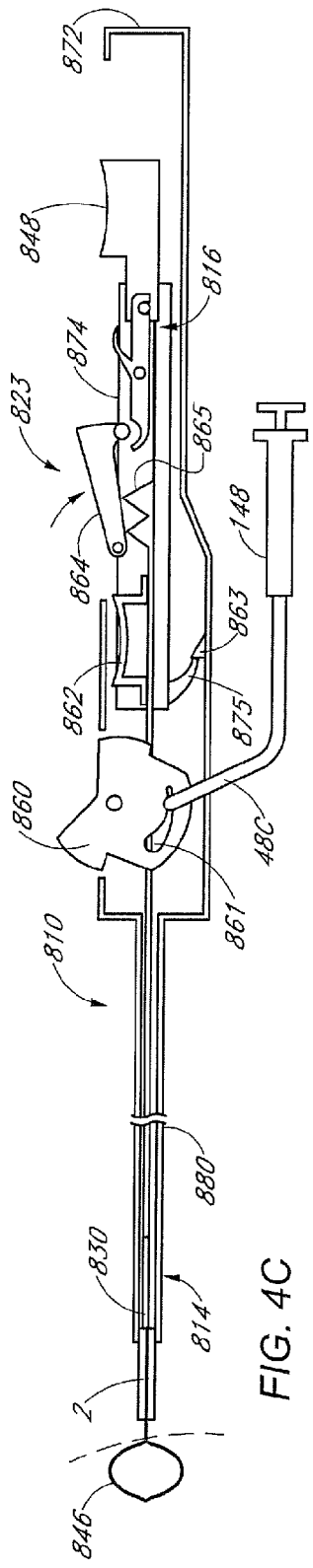

The apparatus 810 can include a second actuator 862 to control movement of the sheath 880 relative to the positioning assembly 814. The second actuator 862 moves between a first position and a second position. In the first position (FIGS. 4A and 4B), the sheath 880 cannot move relative to the positioning assembly 814, thus preventing inadvertent exposure of the sealant 2. Moving the second actuator 862 from the first position to the second position, as shown in FIG. 4C, permits the sheath 880 to move relative to the positioning assembly 814. Retracting the sheath 880 exposes the sealant 2 to the arteriotomy site, while the positioning assembly 814 remains stationary. Retracting the sheath 880 can also cause a portion of the outer housing 872 to at least partially cover the second actuator 862.

The apparatus 810 can include a locking mechanism to prevent the inner housing 874 from moving relative to the outer housing 872. As the sheath 880 retracts, the outer housing 872 moves between a first position and a second position. When the outer housing 872 is in the first position (FIGS. 4A and 4B), the inner housing 874 can move relative to the outer housing 872. When the outer housing 872 is in the second position (FIG. 4C), the inner housing 874 is unable to move proximally relative to the outer housing 872.

As shown by FIGS. 4C and 4D, the apparatus 810 can include a third actuator 864. The third actuator 864 moves between a first position and a second position. Moving the third actuator 864 from the first position to the second position advances the support member 830 to tamp the sealant 2. Tamping the sealant 2 can prevent substantial movement of the sealant 2 and facilitate hemostasis.

Moving the third actuator 864 from the first position to the second position can release a retraction lock 816. The retraction lock 816 prevents the positioning assembly 814 from inadvertently retracting prior to tamping the sealant 2. Releasing the retraction lock 816 permits at least a portion of the positioning assembly 814 to move proximally relative to the support member 830.

The apparatus can include a fourth actuator 848 capable of moving between a first position and a second position. Unlocking the retracting lock 816 permits movement of the fourth actuator 848. Moving the fourth actuator 848 from the first position to the second position retracts at least a portion the positioning assembly 814 relative to the support member 830.

In FIG. 4E, the first actuator 860 moves to the open position to permit fluid flow through the inflation line 48c. When the first actuator 860 is in the open position, the syringe 148 can deflate the positioning element 846. In FIG. 4F, the positioning member 814 is retracted through the sealant 2, so the entire apparatus 810 can be removed from the patient.

As described above, the apparatus 810 can include an actuation mechanism to control fluid flow to the positioning element 846. The actuation mechanism can include any of the features described below in connection with FIGS. 5A-7B, alone or in combination with each other.

FIGS. 5A and 5B depict the first actuator 860*a* moving between the opening position and the closed position. FIGS. 5A-1 and 5B-1 illustrate a cross-sectional view of the inflation line 48*a*. The outer housing 872*a* of the handle includes an opening through which a portion of the first actuator 860*a* extends. In FIGS. 5A and 5B, the first actuator 860*a* is a valve, but the first actuator 860*a* and the valve can also be separate components. The valve can include a pinch mechanism to restrict fluid flow through the inflation line 48*a*.

The first actuator 860*a* can move between the open position (FIG. 5A) and the closed position (FIG. 5B). In the open position, fluid can flow through inflation line 48*a*. In the closed configuration, fluid cannot flow through the inflation line 48*a*. Although FIGS. 5A and 5B depict the first actuator 860*a* as a rocker, the first actuator 860*a* can take on other shapes.

Figure 6A:
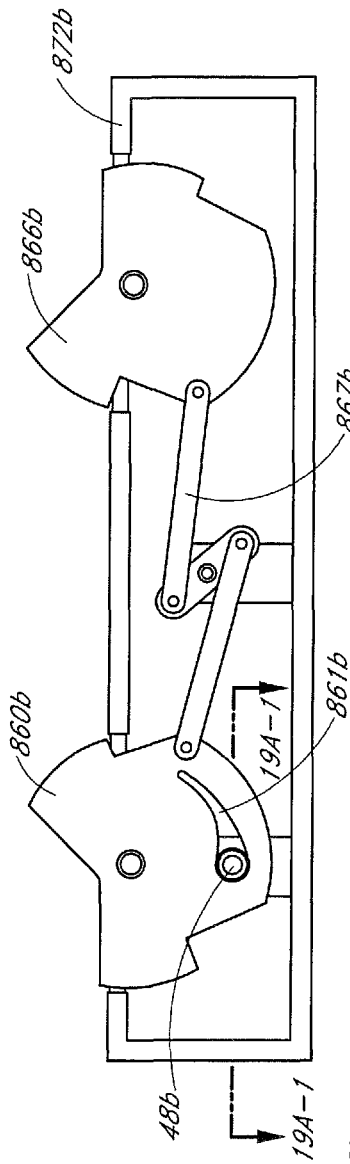
Figures 1, 6A:
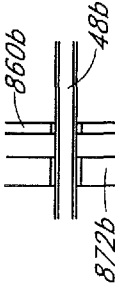
Figure 6B:
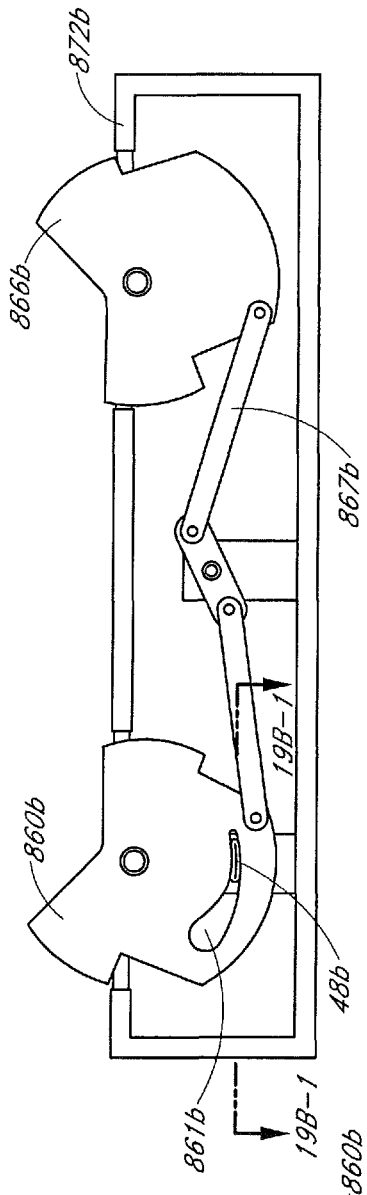
Figures 1, 6B:
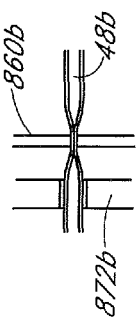

FIGS. 6A and 6B depict an apparatus having the first actuator 860*b* and a deflation actuator 866*b*. FIGS. 6A-1 and 6B-1 illustrate cross-sectional views of the inflation line 48*b*. A linkage portion 867*b* connects the first actuator 860*b* to the deflation actuator 866*b*. Although the linkage portion 867*b* shown in FIGS. 6A and 6B includes multiple link members, the linkage portion 867*b* may only include one link member (see FIGS. 6E-6F). The outer housing 872*b* includes two openings through which a portion of the first actuator 860*b* and the deflation actuator 866*b* extend.

Similar to FIGS. 5A and 5B, the first actuator 860*b* can move from a first position to a second position to restrict fluid flow through the inflation line 48*b*. Moving the first actuator 860*b* from the first position to the second position causes the deflation actuator 866*b* to move from a first position to a second position. Moving the deflation actuator 866*b* from the second position to the first position causes the first actuator 860*b* to move from the second position to the open position to permit fluid flow through the inflation line 48*b*.

Similar to FIGS. 6A and 6B, FIGS. 6C and 6D, can include a first actuator 860*c* and a deflation actuator 866*c* connected by linkage portion 867*c*. The linkage portion 867*c* can include one or more link members. Unlike FIGS. 6A and 6B, the first actuator 860*c* and the deflation actuator 866*c* are different from the valve 884*c*. For example, the valve 884*c* can be positioned distal to the first actuator 860*c* and the deflation actuator 866*c*.

The first actuator 860*c* can move from a first position to a second position to close the valve 884*c* and restrict fluid flow through the inflation line. Moving the first actuator 860*c* from the first position to the second position causes the deflation actuator 866*c* to move from a first position to a second position. Moving the deflation actuator from the second position to the first position causes the first actuator 860*c* to move from the second position to the first position and open the valve 884*c*.

Similar to FIGS. 6A-D, FIGS. 6E and 6F can include a first actuator 860*d* and a deflation actuator 866*d* connected by linkage portion 867*d*. Unlike FIGS. 6A and 6B, the linkage portion 867*d* only includes one link member. In addition, similar to FIGS. 6C and 6D, the first actuator 860*d* and the deflation actuator 866*d* are different from the valve 884*d*. For example, the valve 884*d* can be positioned distal to the first actuator 860*d* and the deflation actuator 866*d*.

The first actuator 860*d* can move from a first position to a second position to close the valve 884*d* and restrict fluid flow through the inflation line. Moving the first actuator 860*d* from the first position to the second position causes the deflation actuator 866*d* to move from a first position to a second position. Moving the deflation actuator from the second position to the first position causes the first actuator 860*d* to move from the second position to the first position and open the valve 884*d*.

The apparatus having the first actuator and the deflation actuator may be useful to minimize confusion associated with operating the apparatus. For example, if the apparatus includes additional actuators to control steps performed between inflating and deflating the positioning element, the additional actuators can be positioned along the handle between the first actuator and the deflation actuator. The actuators can be positioned based on the procedural step each actuator controls, such that the user can move his/her hand proximally for each subsequent step of the procedure.

The deflation actuator may be positioned proximally of the additional actuators because deflating the positioning element is the final step before withdrawing the apparatus.

As described above, the first actuator and the valve can be separate components. As shown in FIGS. 7A-B, the first actuator 960 moves between a first position and a second position to control the position of the valve 961. Moving the first actuator 960 from the first position (FIG. 7A) to the second position (FIG. 7B) moves the valve 961 from an open position to a closed position. In the closed position, the valve 961 restricts fluid flow through the inflation line 948. FIGS. 7A-1 and 7A-2 illustrate cross sectional views of the inflation line 948 moving from an open configuration to a closed configuration. Moving the first actuator 960 from the second position to the first position moves the valve 961 from the closed position to the open position, thus permitting fluid to flow through the inflation line 948.

The first actuator 960 can be a lever. A pin connects the first actuator 960 to the valve 961. The valve 961 can be a sliding valve having a pinch mechanism to restrict fluid flow through the inflation line 948. Moving the first actuator 960 between the first position and the second position slides the valve 961 linearly between the open position and the closed position. Although FIGS. 7A-B depict the first actuator 960 as a lever, the apparatus can include any other mechanism capable of moving the valve 961, such as a rack and pinion arrangement, a cam mechanism, or any other actuator.

Figure 8A:
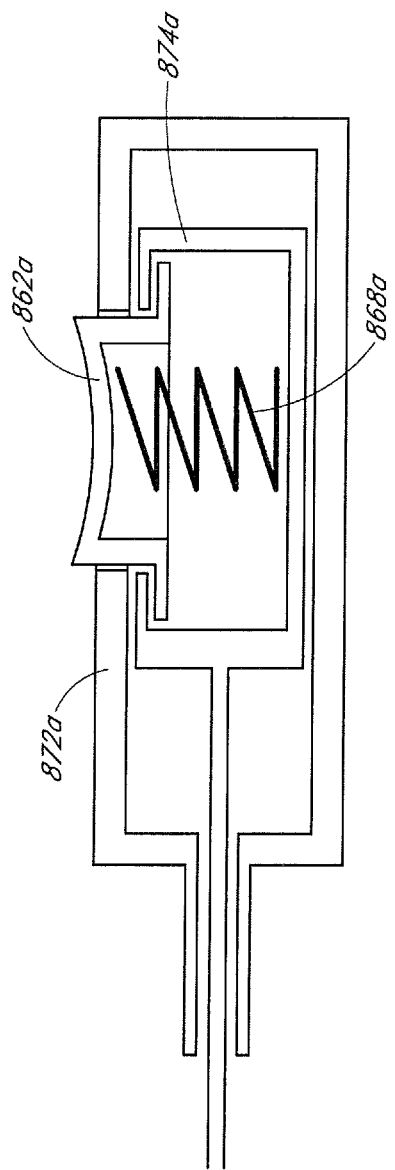
FIGS. 8A-8B illustrate a mechanism for controlling movement of an outer housing relative to an inner housing.
Figure 8B:
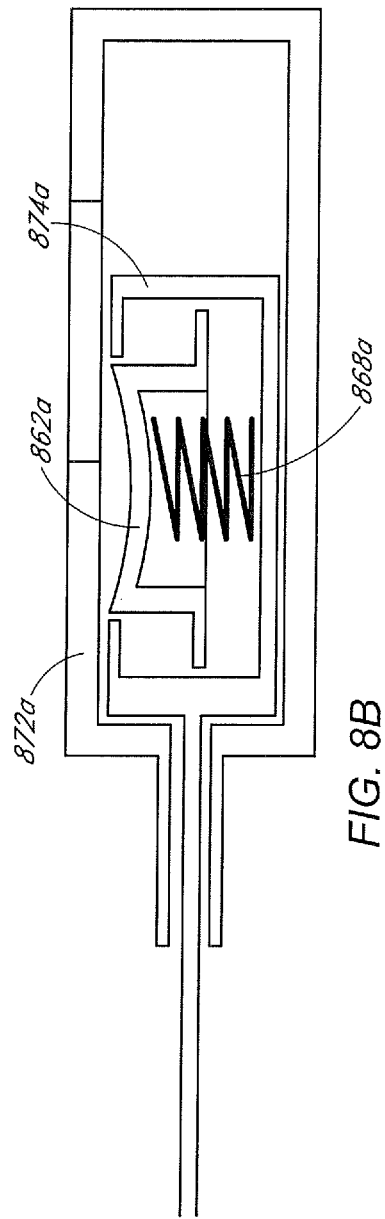

The apparatus 810 can include the second actuator 862 to control movement of the sheath 880 relative to the positioning assembly 814. The outer housing 872 can include an opening through which at least a portion of the second actuator 862 extends. As shown in FIGS. 8A and 8B, the second actuator 862 can be a spring-actuated button.

The second actuator 862a moves between a first position (FIG. 8A) and a second position (FIG. 8B). When the second actuator 862a is in the first position, the second actuator 862a prevents proximal movement of the sheath relative to the positioning assembly. When the second actuator 862a is in the second position, the sheath can move proximally relative to the positioning assembly. As the sheath moves proximally, the outer housing 872a prevents the second actuator 862a from moving to the first position. Although the second actuator 862a illustrated in FIGS. 8A and 8B includes a spring mechanism 868a, any other locking mechanism described herein can be used to control movement of the sheath relative to the positioning assembly.

As shown in FIGS. 9A and 9B, the second actuator 862b can include a detent 869b. When the second actuator 862b is in the first position (FIG. 9A), the sheath cannot move relative to the positioning assembly. When the second actuator 862b is in the second position (FIG. 9B), the detent 869b locks the second actuator 862b in a depressed position, thus permitting the sheath to move proximally relative to the positioning assembly. As the sheath moves proximally, the outer housing 872b moves over the second actuator 862b and keeps the second actuator 862b depressed.

The apparatus 810 can also include a mechanism to restrict the distance the sheath 880 can move relative to the positioning assembly 814. For example, as shown in FIGS. 8B and 8B, the sheath can only move until the distal end of the inner housing 874 abuts the distal end of the outer housing 872 or a different feature in the handle 823.

As described earlier, the handle 823 can include a locking mechanism to lock the inner housing 874 relative to the outer housing 872. As shown in FIGS. 4A-4F, the locking mechanism can include one or more protrusions 863 positioned along an inner wall of the outer housing 872 and one or more resilient members 875 positioned on the inner housing 874. As the sheath 880 moves proximally, the one or more resilient members 875 flex inwardly and move past the one or more protrusions 863. After the one or more resilient member 875 move past the one or more protrusions 863, the inner housing 874 is unable to move proximally relative to the outer housing 872.

Figure 10A:
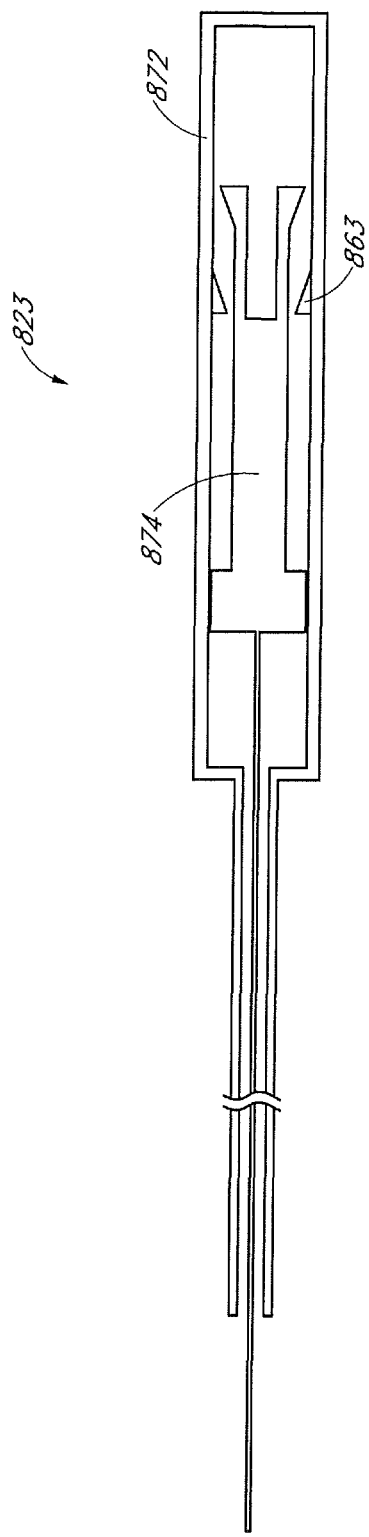
FIGS. 10A-10B illustrate yet another mechanism for controlling movement of an outer housing relative to an inner housing.
Figure 10B:
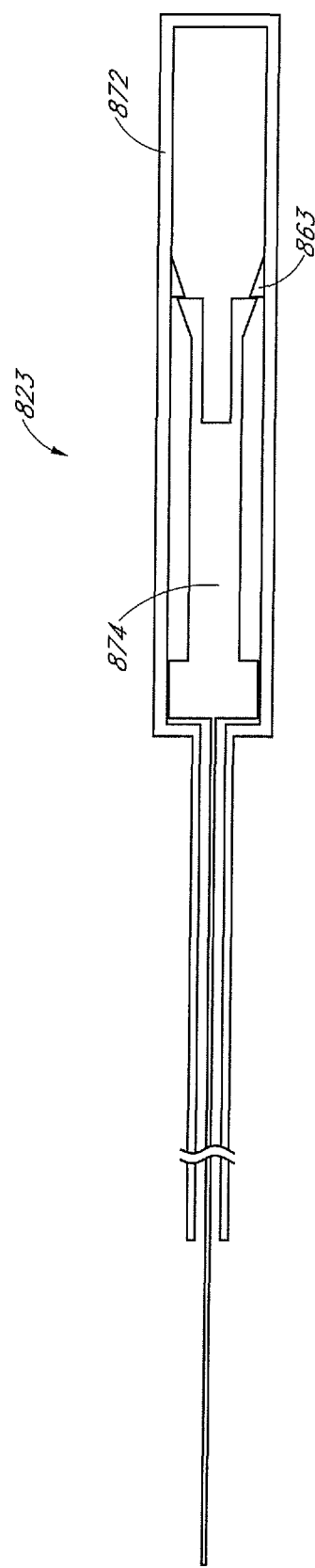

In FIGS. 10A and 10B, the locking mechanism includes at least two protrusions 863 along the inner wall of the outer housing 872 and at least two resilient members 875 positioned at a proximal end of the inner housing 874. The resilient members 875 are capable of flexing inward to move distally past the one or more protrusions 863. As the sheath 880 is withdrawn, the resilient members 875 flex inward and move past the protrusions 863. After the resilient members 875 move past the protrusions, the inner housing 874 cannot move proximally relative to the outer housing 872.

Alternatively, the locking mechanism can include one or more protrusions 863 positioned on the inner housing 874 and one or more resilient members positioned along the inner wall of the outer housing 872. Other locking mechanisms described herein can also be used to lock the inner housing 874 relative to the outer housing 872.

The apparatus 810 can include a mechanism to release the positioning assembly 814 from the inner housing 874. Releasing the positioning assembly 814 permits the positioning assembly 814 to move proximally while maintaining the position of the support member 830. Alternatively, the apparatus 810 can include a mechanism to release the inner housing from the outer housing.

Figure 11A:
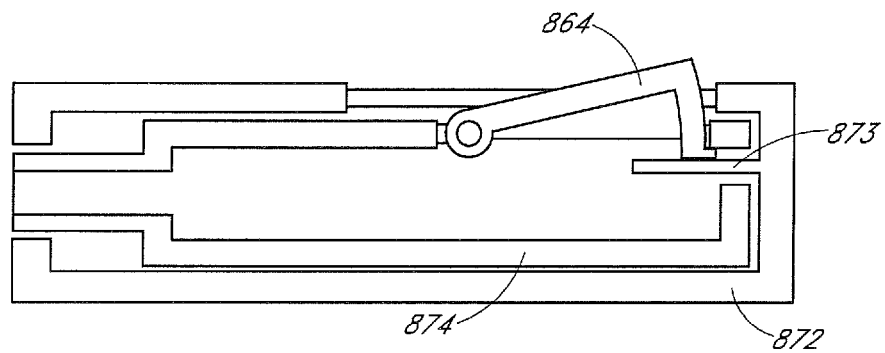
FIGS. 11A-11C illustrate a locking mechanism to prevent actuation of a support member.
Figure 11B:
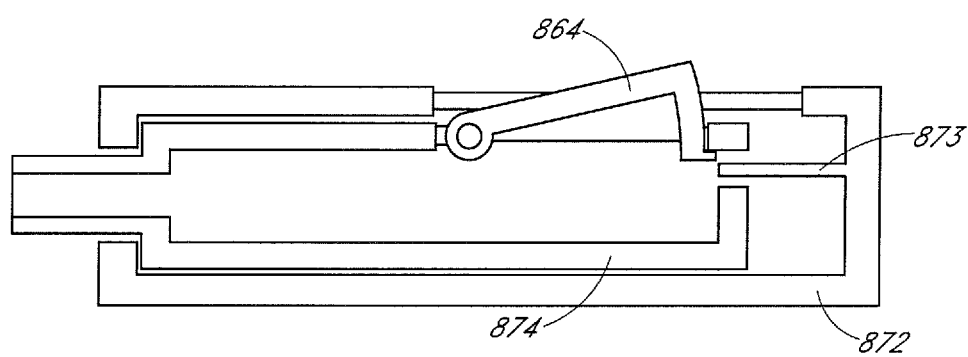
Figure 11C:
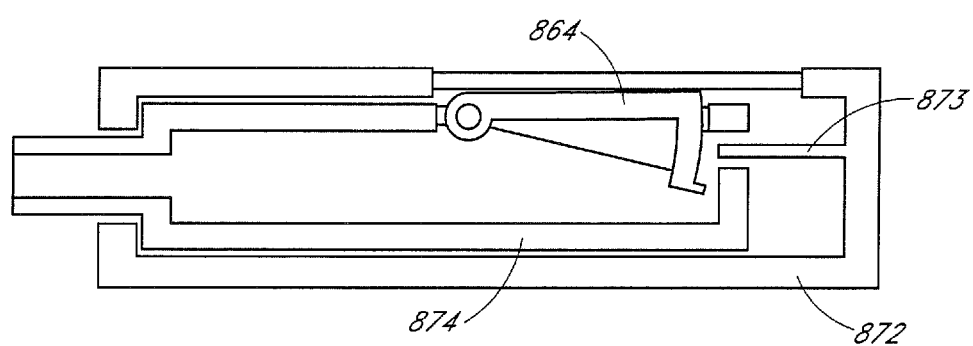

FIGS. 11A through 11C illustrate a mechanism to prevent the support member 830 from advancing prior to retracting the outer sheath 880. As shown in FIG. 11A, locking mechanism can be a tab 873 that prevents movement of the third actuator 864. However, after the sheath 880 moves proximally (FIG. 11B), the tab 873 moves proximally to enable movement of the third actuator 864 from a first position (FIG. 11B) to a second position (FIG. 11C). Other locking mechanisms described herein can also be used to prevent the support member 830 from advancing.

Figure 12A:
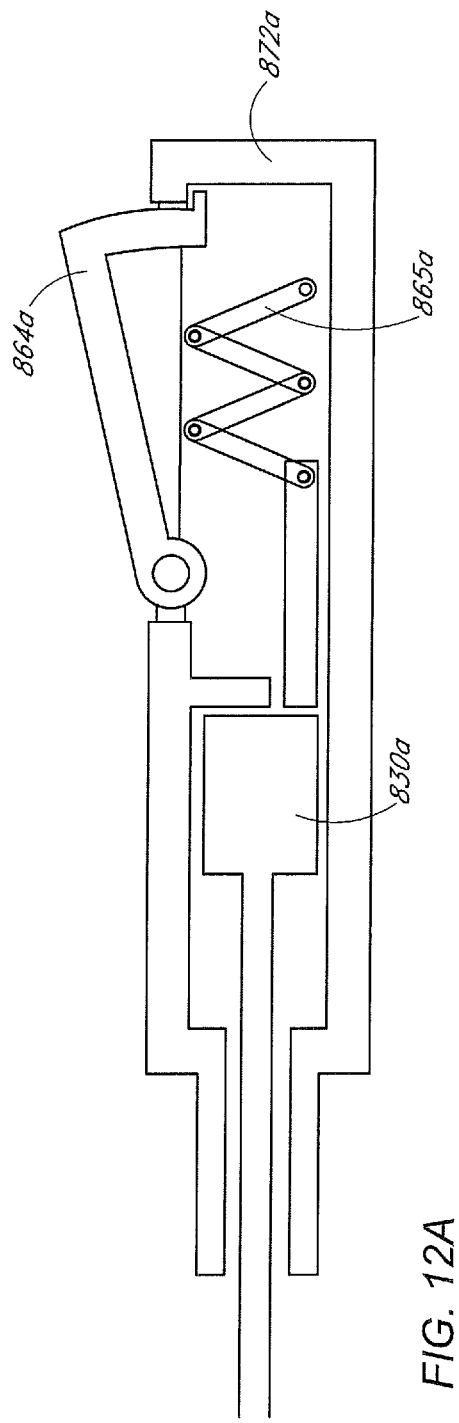
FIGS. 12A-12B illustrate a mechanism for advancing a support member.
Figure 12B:
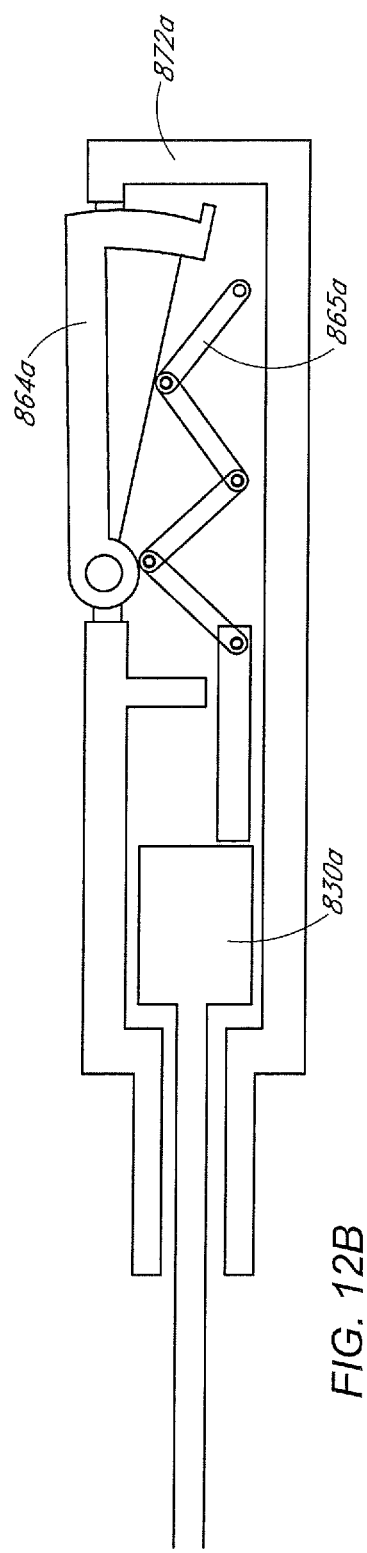

FIGS. 12A and 12B illustrate one mechanism for advancing the support member 830. Moving the third actuator 864 from the first position to the second position causes a linkage element 865 to extend and advance the support member 830. The support member 830 can extend until a portion of the support member 830 abuts a feature of the handle, such as the distal end of the inner housing 874 or the outer housing 872. The distance the support member 830 can advance may also be limited by the distance the linkage element 865 can extend.

Figure 13A:
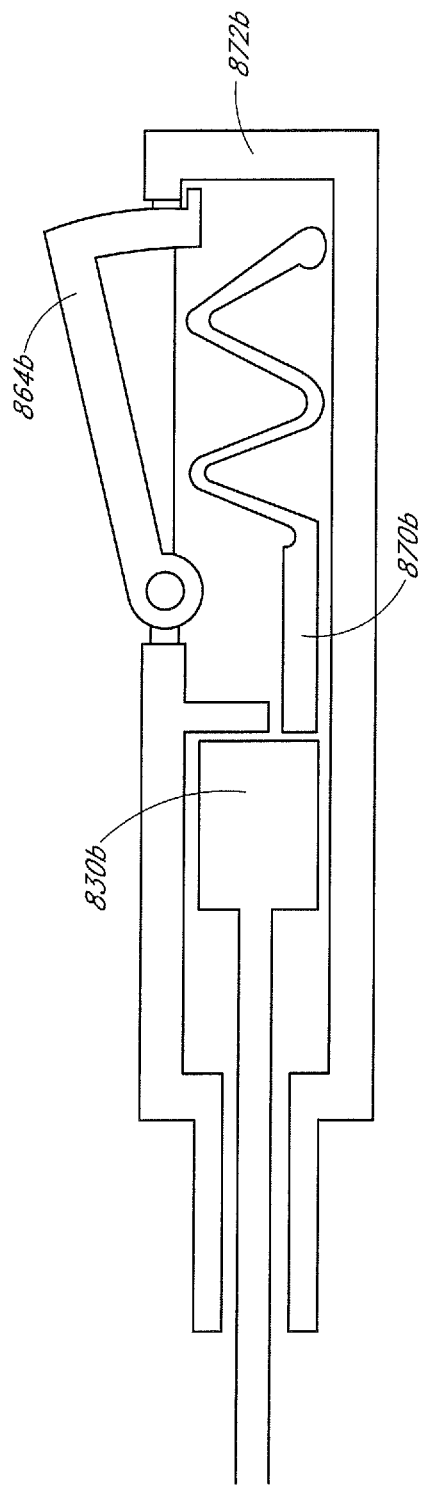
FIGS. 13A-13B illustrate another mechanism for advancing a support member.
Figure 13B:
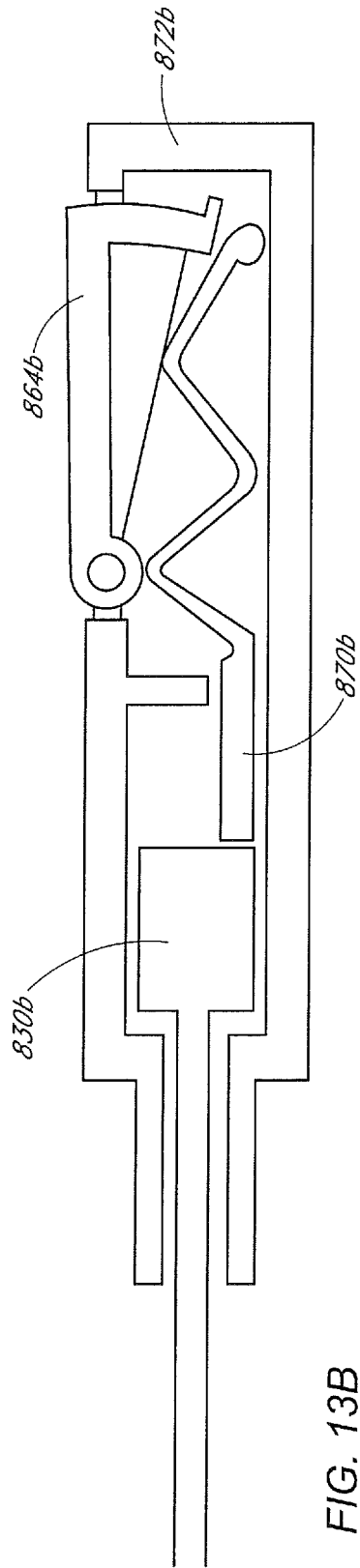
Figure 14A:
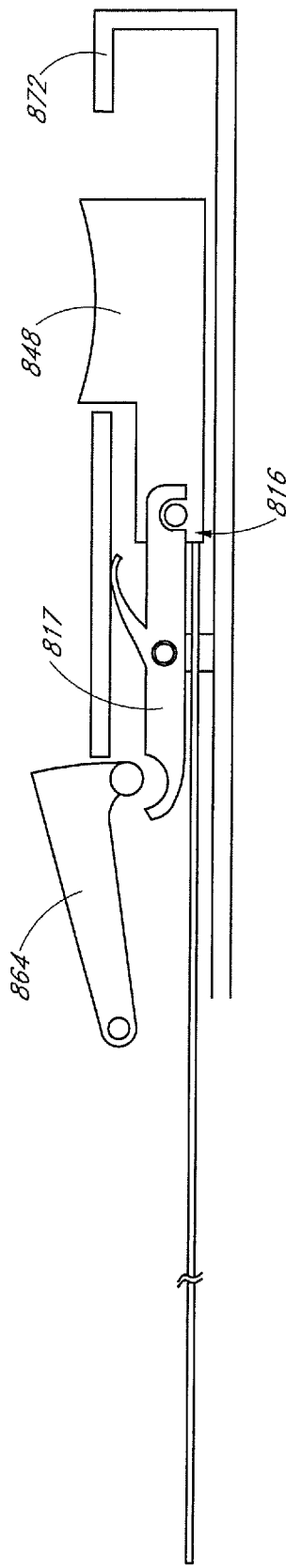
FIGS. 14A-14B illustrate a retraction lock to restrict movement of a positioning assembly.
Figure 14B:
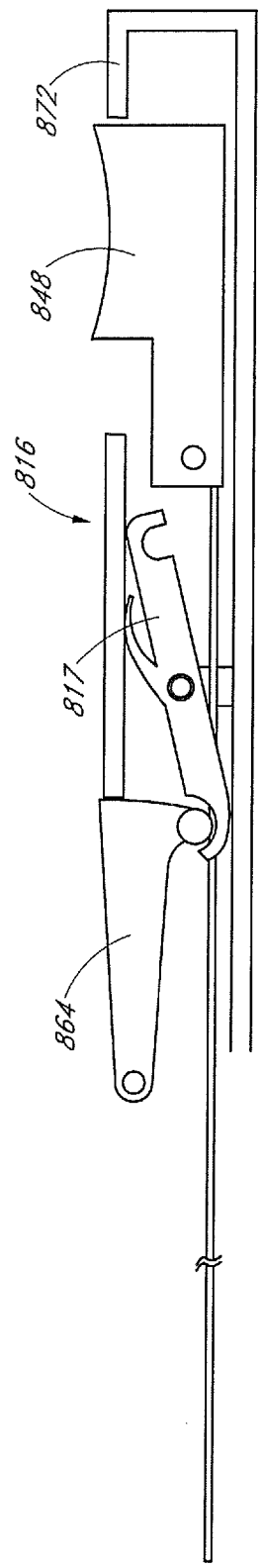

FIGS. 13A and 13B illustrate the apparatus 810 having a spring member 870. Moving the third actuator 864 from the first position to the second position causes the spring member 870 to expand and advance the support member 830 distally. The support member 830 can extend until a portion of the support member 830 abuts a feature of the handle, such as the distal end of the inner housing 874 or the outer housing 872. The distance the support member 830 can advance may also be limited by the distance the spring member 870 can expand. Other mechanisms can be used to advance the support member 830, such as the rack and pinion arrangement described in connection with apparatus 710 or any other actuator.

As described earlier, the apparatus 810 can include a retraction lock 816 to lock the position of the positioning assembly 814 relative to the inner housing 874. Moving the third actuator 864 from the first position to the second position can release the retraction lock 816 by moving a lever 817 from a first position to a second position. When the lever 817 is in the second position, the positioning assembly 814 can move relative to the outer housing 872. Retracting the fourth actuator 848 of the positioning assembly 814 causes the positioning assembly 814 to retract past the sealant 2. The support member 830 can retain the position of the sealant 2 while the positioning assembly 814 retracts. After the positioning element 814 retracts, the entire apparatus 810 can be removed from the patient. Other locking mechanisms described herein can also be used to lock the position of the positioning assembly 814 relative to the inner housing 874.

Figure 15D:
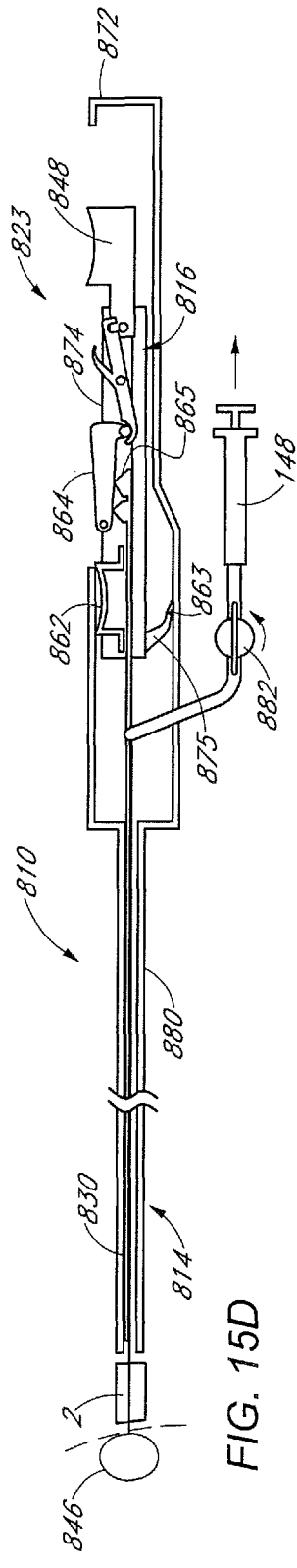
Figure 15E:
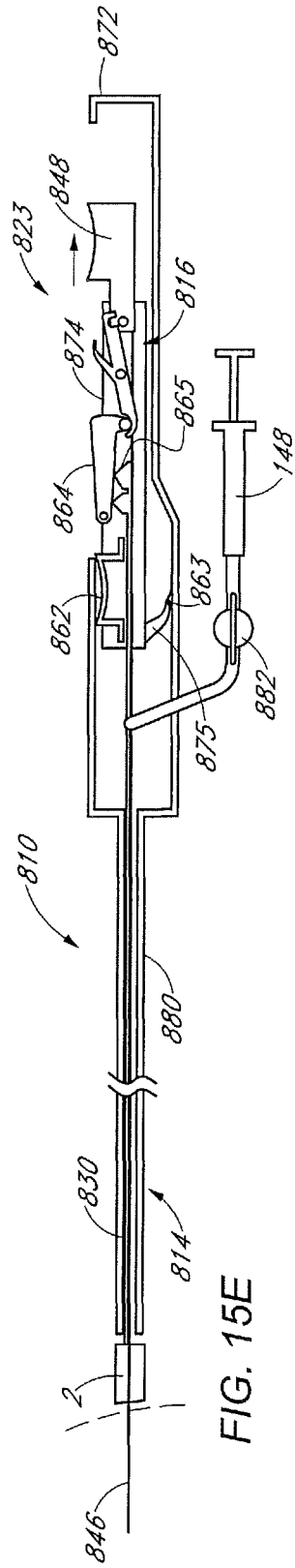
Figure 15F:
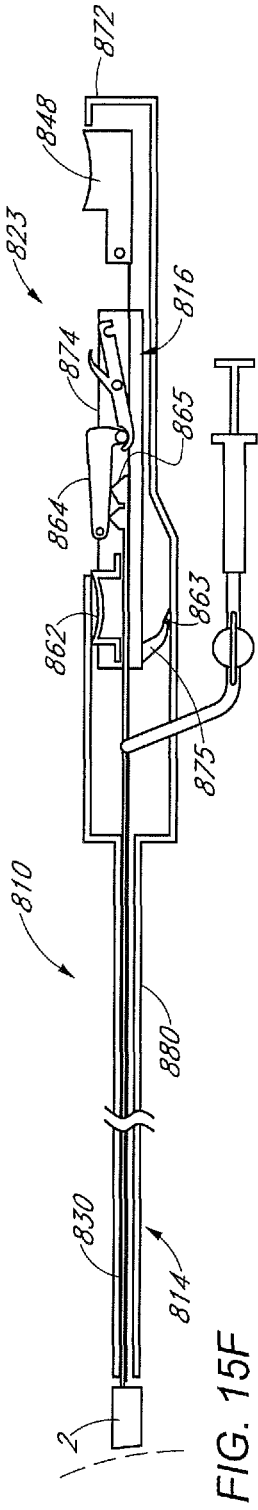

FIGS. 15A-15F schematically illustrate a method of delivering a sealant similar to the method shown in FIGS. 4A-4F. However, as described earlier, the handle 823 does not have to include four actuators 860, 862, 864, and 848. For example, as shown in FIGS. 15A-15F, the handle does not include the first actuator 860. Instead, the inflation line 48c includes a valve 882. The valve 882 moves between a first position and a second position. When the valve 882 is in the first position, as shown in FIG. 15A, fluid can flow from the syringe to the positioning member 846. When the valve 882 moves from the first position to the second position, as shown in FIG. 15B, fluid can no longer flow from the syringe to the positioning member 846.

Figure 16B:
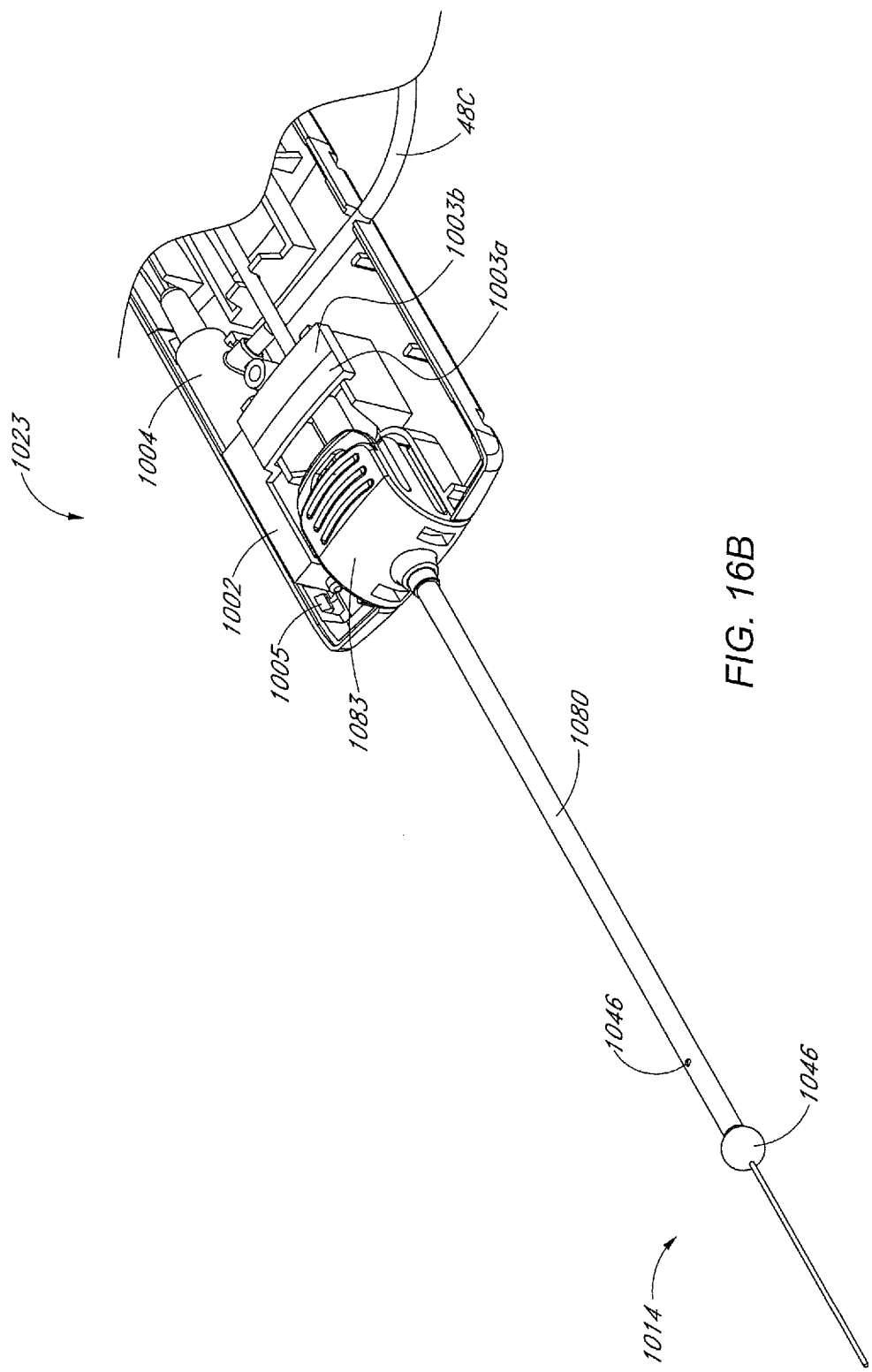

FIGS. 16A-B illustrate an apparatus 1010 for delivering a sealant to an arteriotomy site. The apparatus 1010 can include any of the features of the sealant delivering apparatuses discussed herein. For example, the apparatus 1010 can include a positioning assembly 1014 having a handle 1023 and a positioning element 1046. At least a part of the positioning assembly 1014 can extend through a sheath 1080. An inflation line 48c can extend from the positioning element 1046 to a syringe 148 or any other mechanism for inflating and deflating the positioning element 1046. The inflation line 48c can include a first actuator 1082 for controlling fluid flow to the positioning element 1046. The handle 1023 can include a second actuator 1062 to permit the sheath 1080 to retract relative to the positioning element 1014, a third actuator 1064 to advance a support member (not shown), and/or a fourth actuator 1048 for retracting at least a portion of the positioning assembly 1014 relative to the sheath 1080.

The sheath 1080 can include a mechanism to indicate when a distal portion of the sheath enters a vessel. For example, the sheath 1080 can include one or more inlet openings 1089 at a distal portion of the sheath 1080. As the sheath 1080 enters the vessel, blood can flow into the openings 1080 and out of an outlet opening outside of the user.

As shown in FIG. 16A, the sheath 1080 can also include a hub 1083 for engaging the handle 1023. For example, the hub 1083 can include one or more openings for engaging one or flanges of the handle, or vice versa. Depressing the sheath hub 1083 can release the sheath 1080 from the positioning assembly 1014. The sheath hub can also include a catch to engage the sealant sleeve (not shown). As the positioning assembly 1014 enters the sheath 1080, the sheath catch can engage the sealant sleeve to transfer the sealant from the sealant sleeve to the sheath 1080.

The apparatus 1010 can also include an inflation indicator 1002. The inflation indicator 1002 indicates when the positioning element 1046 is inflated to a pre-determined pressure and signals a user to seal the inflation line 48c. As shown in FIG. 16B, the inflation line connects to a plunger system 1004. As the positioning element 1046 inflates, the shaft member 1005 moves from a first position to a second position. As the shaft member 1005 move to the second position, the indicator 1002 moves from a first position to a second position. When the indicator 1002 is in the second position, the positioning element 1046 is fully inflated. As the positioning element 1046 deflates, the shaft member 1005 moves from the second position to the first position and the indicator 1002 moves from the second position to the first position. When the indicator 1002 is in the first position, the positioning element 1046 is not fully inflated.

The indicator 1002 can include a first indicator 1003a and a second indicator 1003b. When the positioning element 1046 is not fully inflated, the first indicator 1003a can be seen through the opening 1006 of the handle 1023. When the positioning element 1046 is fully inflated, the second indicator 1003b can be seen through the opening 1006 of the handle 1023.

Any of the sealant delivering apparatuses discussed herein can be a component of a system including, but not limited to, a guidewire or a dilator. The guidewire can include any of the features described in connection with guidewire 799 described above. The dilator can also include one or more of the features described in connection with the dilator 790 described above and/or dilator 1190 (FIGS. 17A-17D) or dilator 1290 (FIGS. 18A-18C) described below.

As described shown in FIGS. 17A-18C, the dilator can contain a fluid lumen that allows blood to flow from an inlet opening near the distal tip of the dilator to an outlet opening near the proximal end of the dilator. Blood flow exits the proximal port when the tip of the sheath enters the vessel. The sheath can then further advanced to ensure that the distal tip of the sheath is in the vessel lumen.

Figure 17A:
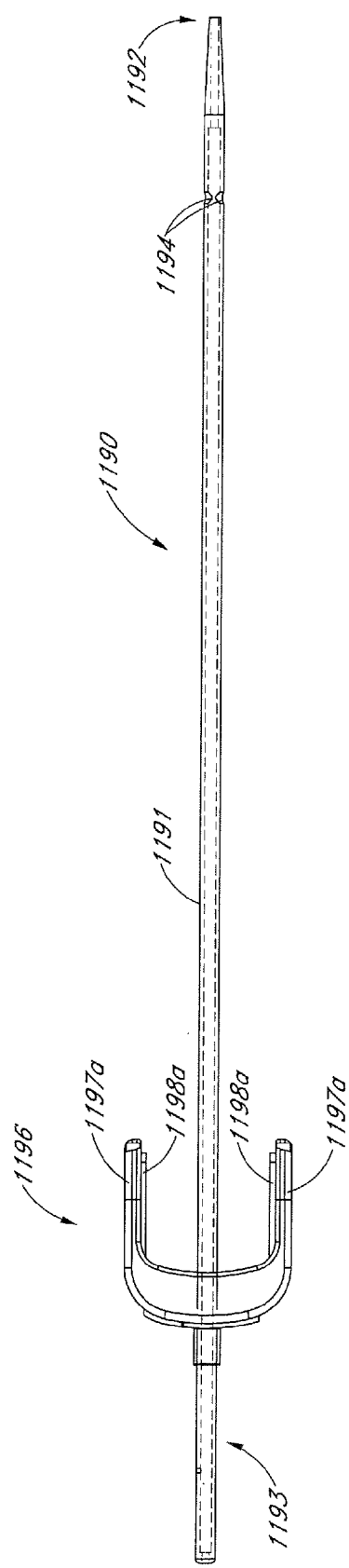

As shown in FIGS. 17A-17D, the dilator 1190 includes an elongate structure 1191 having a lumen extending therethrough. The dilator 1190 can also include a proximal portion 1193 having a dilator hub 1196 for engaging the sheath and/or a distal portion 1192 having a tapered end. As shown in FIG. 17A, the dilator hub 1196 can be U-shaped. The U-shaped dilator hub 1196 defines an opening for receiving a proximal end of the sheath. The dilator hub 1196 can also include hub members 1197a, 1197b configured to engage an outer surface of the sheath. The dilator hub 1196 can also include one or more flanges to engage a corresponding feature of the sheath. For example, as shown in FIG. 17A, the hub members 1197a, 1197b can include flanges 1198a, 1198b to and/or the hub 1196 can include flanges 1199a, 1199b near a top surface of the dilator hub.

The dilator 1190 can also include a bleed back feature to help determine when the distal portion 1192 of the dilator 1190 enters a vessel. For example, the dilator 1190 can include one or more inlet openings 1194 at a distal portion 1192 of the dilator 1190. As shown in FIG. 17A, the dilator 1190 can include two inlet openings 1194. The inlet openings 1194 can be positioned proximal to the tapered portion of the elongate structure 1191 and/or along the same plane transverse to the longitudinal axis of the dilator 1190. The dilator 1190 can also include one or more outlet openings 1195 positioned proximal to the dilator hub 1196. As shown in FIG. 17A, the dilator 1190 can include one outlet opening 1195. The outlet opening 1195 can be positioned along the same plane as one of the inlet openings 1194. The dilator hub can include a direction feature 1197 for indicating the direction the blood flow will exit. As shown in FIG. 17C, the direction feature 1197 can be an arrow along a top surface of the dilator hub 1196.

The lumen extending through the elongate structure 1191 can have a varying diameter. For example, the lumen can have a first diameter 1189 at the distal portion 1192 and proximal portion 1193 of the elongate structure 1192 and a second diameter 1188 between the distal portion 1192 and proximal portion 1193. The first diameter 1189 can be less than the second diameter 1188. The first diameter 1189 can include a diameter that is larger than the outer diameter of the guide wire and smaller than the second diameter 1188. In some embodiments, the first diameter 1189 at least about half of the second diameter 1188 and/or less than or equal to about three-fourths of the second diameter 1188. In some embodiments, the first diameter 1189 is about two-thirds the second diameter 1188.

The lumen diameter can vary while the outer diameter of the elongate structure 1191 remains the same. For example, the proximal portion 1193 can have an outer diameter that is the same as a portion between the proximal portion 1193 and the distal portion 1192. The varying diameter permits the proximal portion 1193 and the distal portion 1192 of the dilator 1190 to form a seal around the guide wire. As such, blood only flows through the inlet openings 1194 to the outlet opening 1195.

Figure 18A:
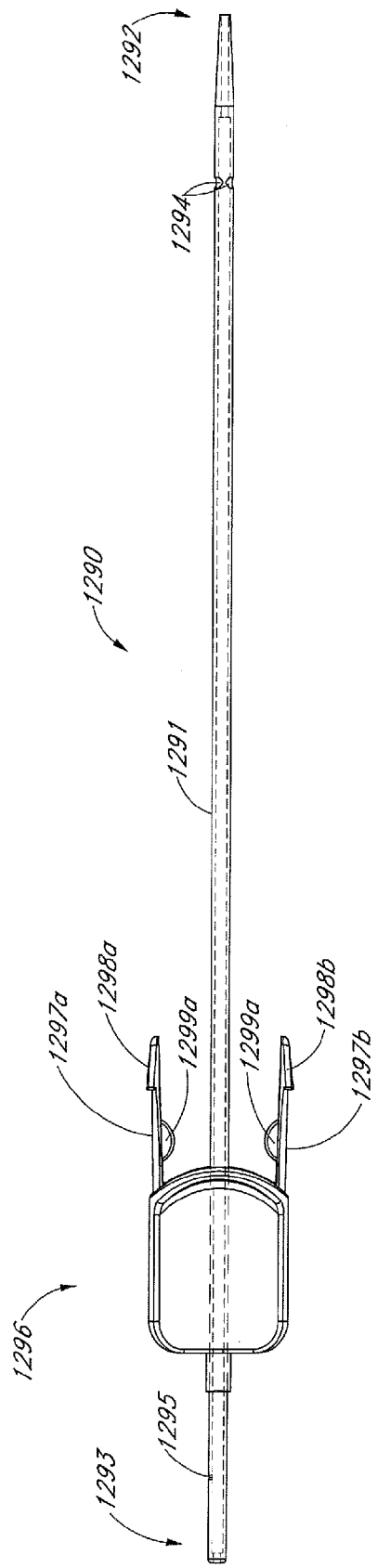

FIGS. 18A-C illustrate a dilator 1290 includes an elongate structure 1291 having a lumen extending therethrough. The dilator 1290 can also include a proximal portion 1293 having a dilator hub 1296 for engaging the sheath and/or a distal portion 1292 having a tapered end. As shown in FIG. 18A, the dilator hub 1296 can include hub members 1297*a*, 1297*b* configured to engage the sheath. For example, the sheath can include corresponding features for receiving the hub members 1297*a*, 1297*b*. The hub members 1297*a*, 1297*b* can also include one or more flanges to engage a corresponding feature of the sheath. For example, as shown in FIG. 18A, the hub members 1297*a*, 1297*b*, can include outward facing flanges 1298*a*, 1298*b* and/or inward facing flanges 1299*a*, 1299*b*. The flanges can be positioned near (e.g., flange 1299*a*, 1299*b*) and/or at a distal portion (e.g., flange 1298*a*, 1298*b*) of the hub members 1297*a*, 1297*b*.

The dilator 1290 can also include a bleed back feature to help determine when the distal portion 1292 of the dilator 1290 enters a vessel. For example, the dilator 1290 can include one or more inlet openings 1294 at a distal portion 1292 of the dilator 1290. As shown in FIG. 18A, the dilator 1290 can include two inlet openings 1294. The inlet openings 1294 can be positioned proximal to the tapered portion of the elongate structure 1291 and/or along the same plane transverse to the longitudinal axis of the dilator 1290. The dilator 1290 can also include one or more outlet openings 1295. As shown in FIG. 18A, the dilator 1290 can include one outlet opening 1295. In some embodiments, the outlet opening 1295 can be positioned along the same plane as one of the inlet openings 1294. In other embodiments, the outlet opening 1295 can be positioned along a different plane from any of the inlet openings 1294. For example, the outlet opening 1295 can positioned along a plane that is perpendicular to the plane passing through the inlet openings 1294.

The lumen extending through the elongate structure 1291 can have a varying diameter. For example, the lumen can have a first diameter 1289 at the distal portion 1292 and proximal portion 1293 of the elongate structure 1292 and a second diameter 1288 between the distal portion 1292 and proximal portion 1293. The first diameter 1289 can be less than the second diameter 1288. The first diameter 1289 can include a diameter that is larger than the outer diameter of the guide wire and smaller than the second diameter 1288. In some embodiments, the first diameter 1289 at least about half of the second diameter 1288 and/or less than or equal to about three-fourths of the second diameter 1288. In some embodiments, the first diameter 1289 is about two-thirds the second diameter 1288.

The lumen diameter can vary while the outer diameter of the elongate structure 1291 remains the same. For example, the proximal portion 1293 can have an outer diameter that is the same as a portion between the proximal portion 1293 and the distal portion 1292. The varying diameter permits the proximal portion 1293 and the distal portion 1292 of the dilator 1290 to form a seal around the guide wire. As such, blood only flows through the inlet openings 1294 to the outlet opening 1295.

In any of the above mentioned dilators, the diameter of any of the outlet opening can be smaller than a diameter of any of the inlet openings. For example, the diameter of any of the outlet opening can be less than or equal to half of the diameter of any of the inlet openings.

Figure 19A:
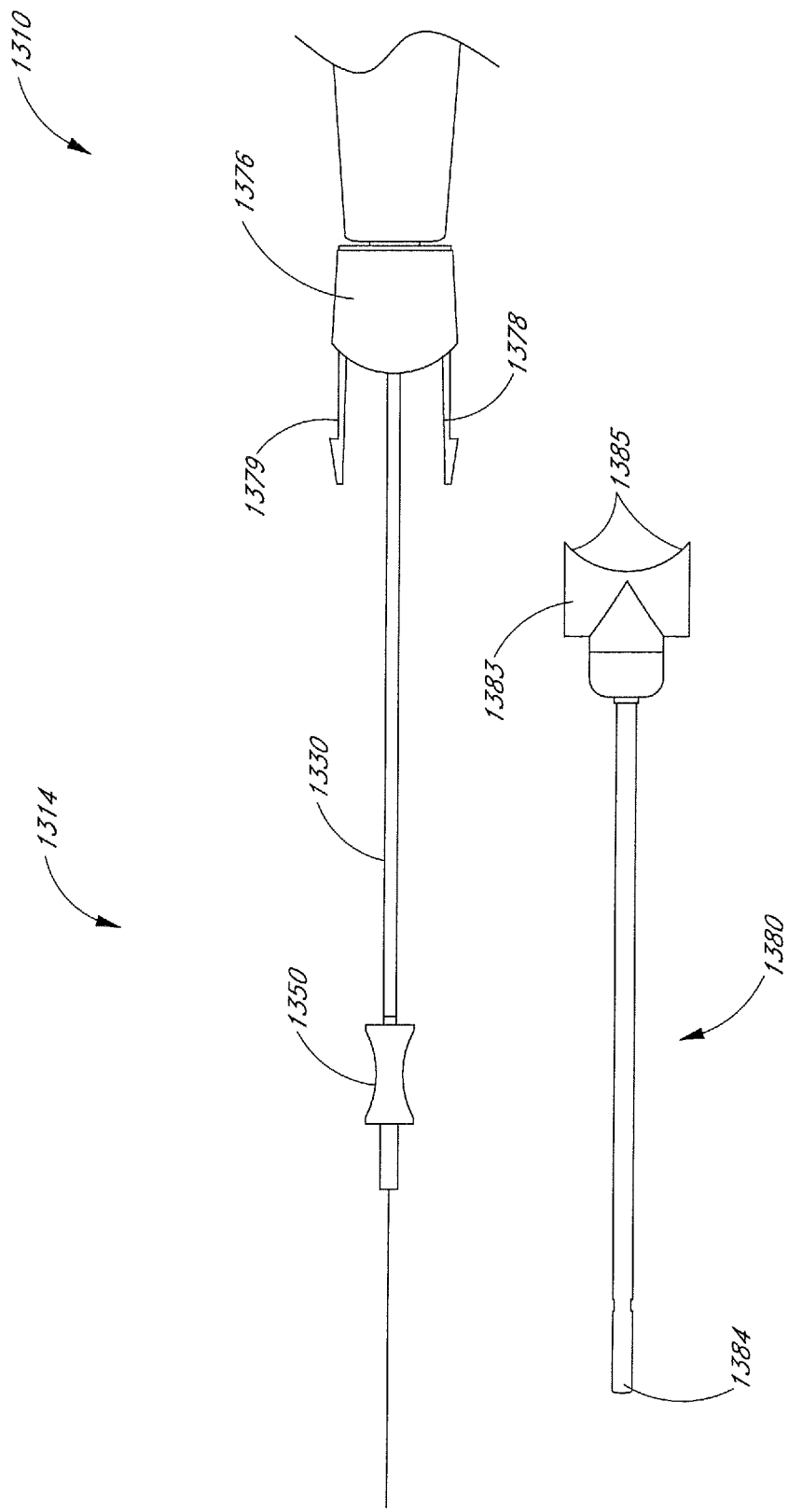

FIGS. 19A-19E illustrate how any of the above mentioned positioning assemblies can engage a sheath. FIG. 19A illustrates an apparatus 1310 before the apparatus 1310 is delivered through the sheath 1380. The apparatus 1310 can include any of the features of the sealant delivering apparatuses described above. The positioning assembly 1314 can engage the sheath 1380, such that movement of the handle 1323 can also move the sheath 1380. For example, the handle 1323 can include a shroud portion 1376 configured to engage a hub 1383 of the sheath 1380. As shown in FIG. 19A, the shroud 1376 can include two tines 1378, and each tine 1378 can include a barb 1379 positioned at a distal portion of the tine 1378. The hub 1383 can include openings 1385 to receive the tines 1378. Other fastening mechanisms without tines can also be used to couple the apparatus 1310 with the sheath 1380, such as a snap fit, interference fit, or screw mechanism.

Figure 19D:
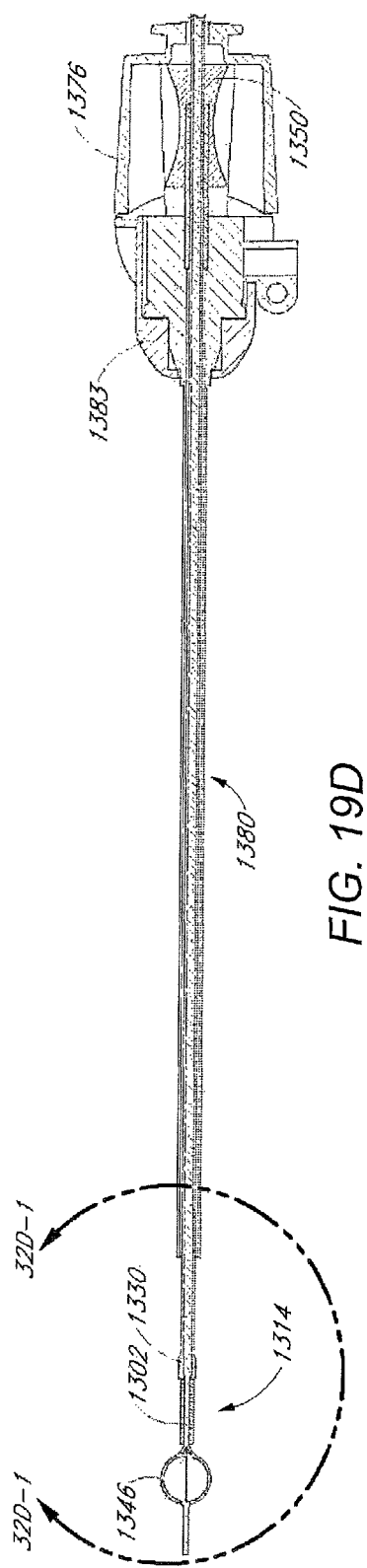
Figures 1, 19D:
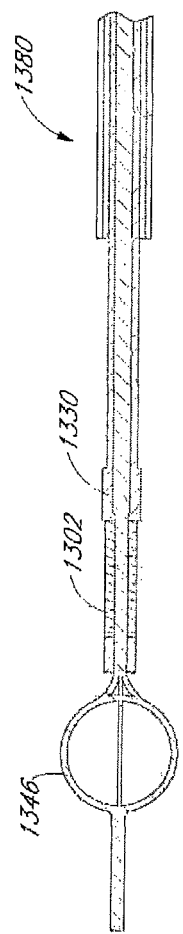

As described above, the sealant 1302 is initially positioned at a distal portion of the positioning assembly 1314 (FIG. 19A). Before the positioning assembly 1314 enters the sheath 1380, a sealant sleeve 1350 covers the sealant 1302 to prevent exposure of the sealant 1302 to the environment. The sealant sleeve 1350 can include any of the features of the sealant sleeve 450 described above. As the positioning assembly 1314 enters the sheath 1380, the sealant 1302 is transferred from the sealant sleeve 1350 to the sheath 1380 (FIG. 19B). The sheath hub 1383 and/or shroud 1376 retains the sealant sleeve 1350. The sheath hub 1383 and/or shroud 1375 retain the sealant sleeve 1350 even as the sheath 1380 is retracted (FIG. 19C) or the sealant 1302 is tamped using the support member 1330 (FIG. 19D).

Figure 20:
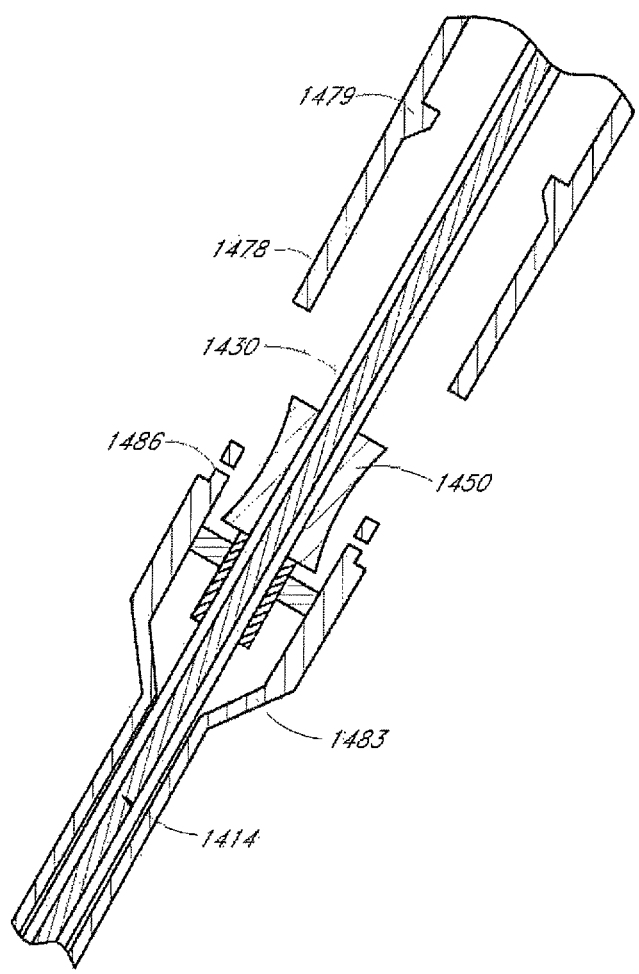
FIG. 20 illustrates another mechanism for engaging a positioning assembly and a sheath.

In some embodiments, as shown in FIG. 20, the tines engage an exterior portion of the sheath hub 1483. For example, the hub 1483 can include grooves 1486 configured to engage the barbs 1478. The sheath hub 1483 can also include an inner diameter that is smaller than an outer diameter of the sealant sleeve 1450 to facilitate the sealant transfer from the sealant sleeve 1450 to the sheath 1480.

Figure 21A:
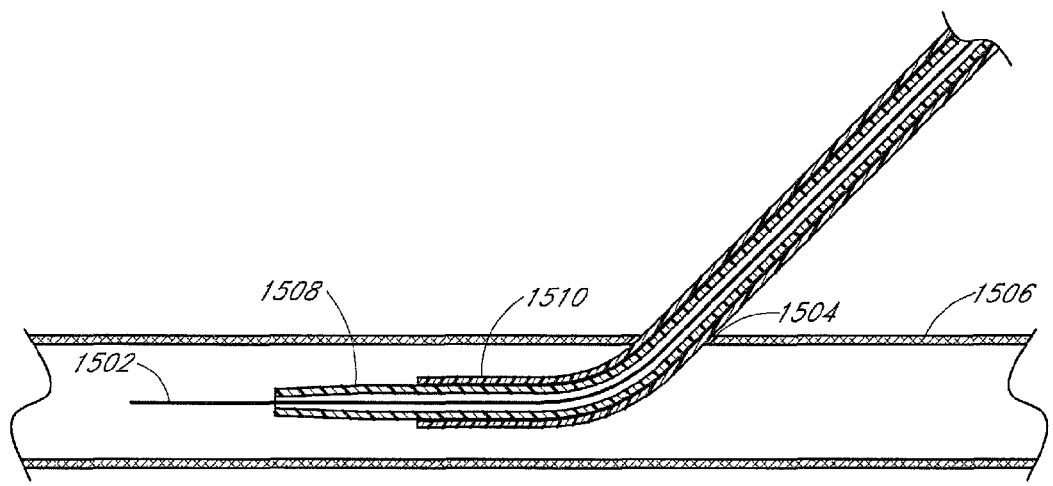
FIGS. 21A-21I illustrate a method for delivering a sealant to an arteriotomy site.

FIGS. 21A-21I describe a method of using the system including any of the sealant delivering apparatuses and dilators described herein. The method can include one or more of the steps described below. A procedural sheath (not shown) can be inserted through a puncture 1504 in a vessel wall 1506 to gain access to a vessel lumen. After the guidewire 1502 extends through the procedural sheath and into the vessel, the procedural sheath can be removed from the tissue tract, leaving the guidewire 1502 in place with the distal tip of the guidewire 1502 positioned within the vessel lumen. The dilator 1508 can then be advanced through the closure system sheath 1510, and the dilator-sheath assembly can be advanced over the guidewire 1502 (FIG. 21A). Any of the mechanisms described herein can be used to determine when the dilator-sheath assembly enters the vessel lumen (e.g., a bleed back port on the dilator and/or sheath).

Figure 21B:
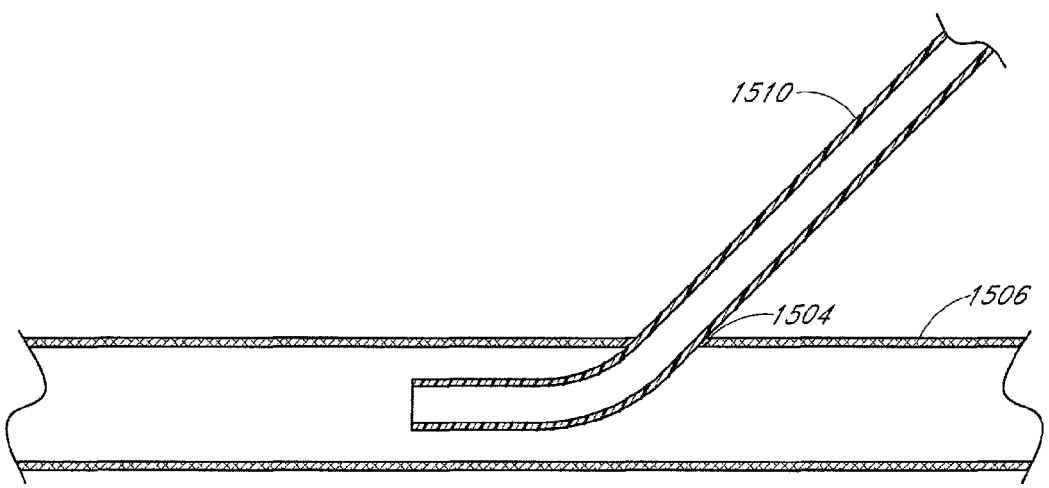
Figure 21C:
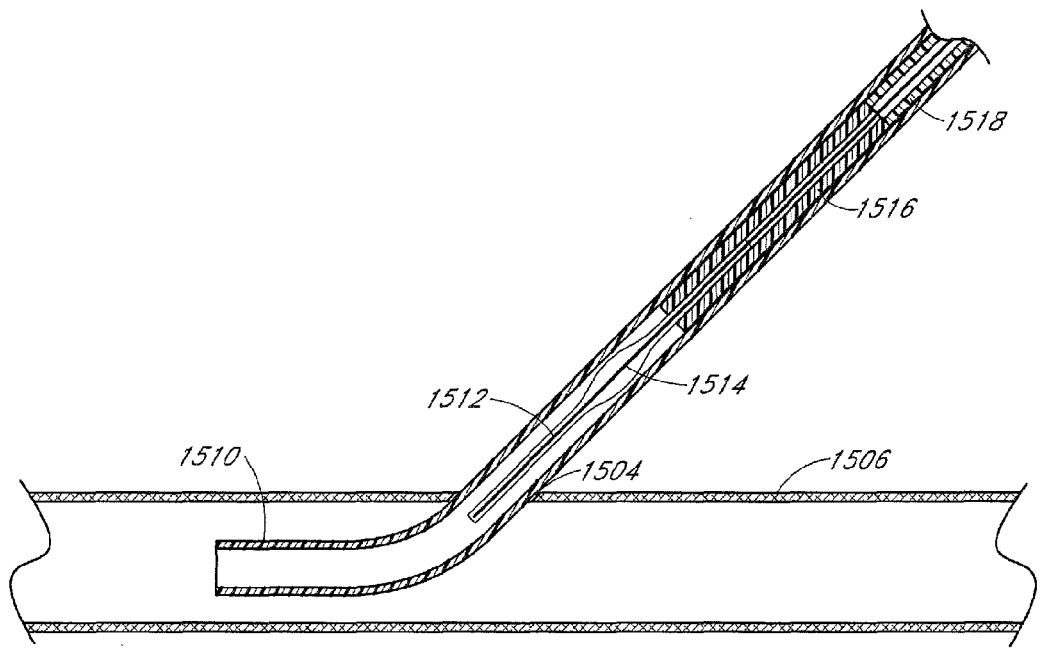
Figure 21D:
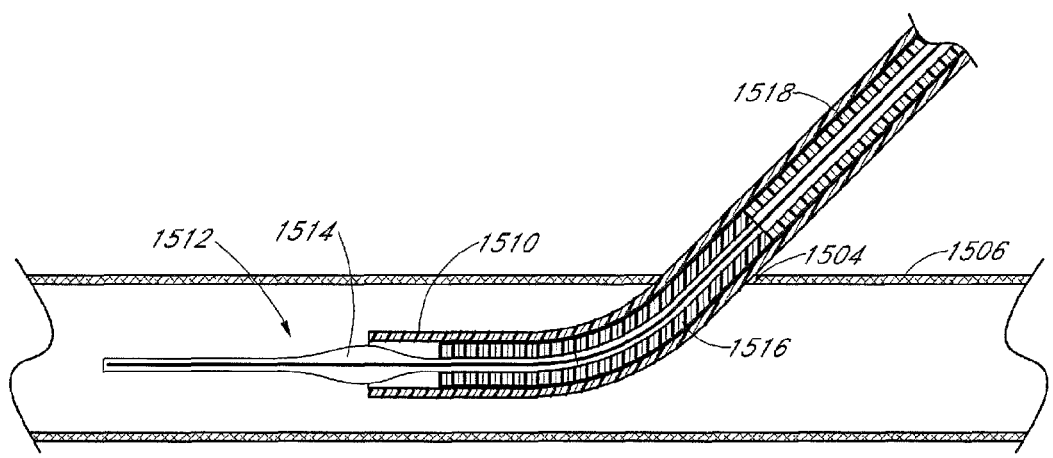
Figure 21E:
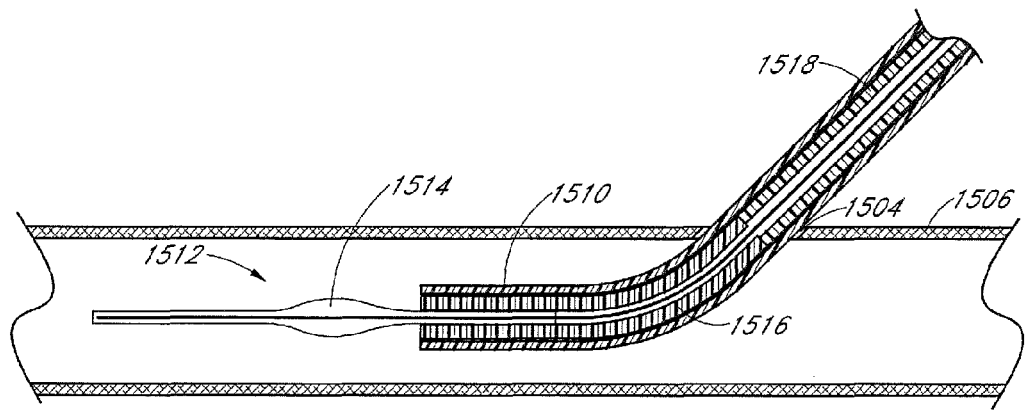
Figure 21F:
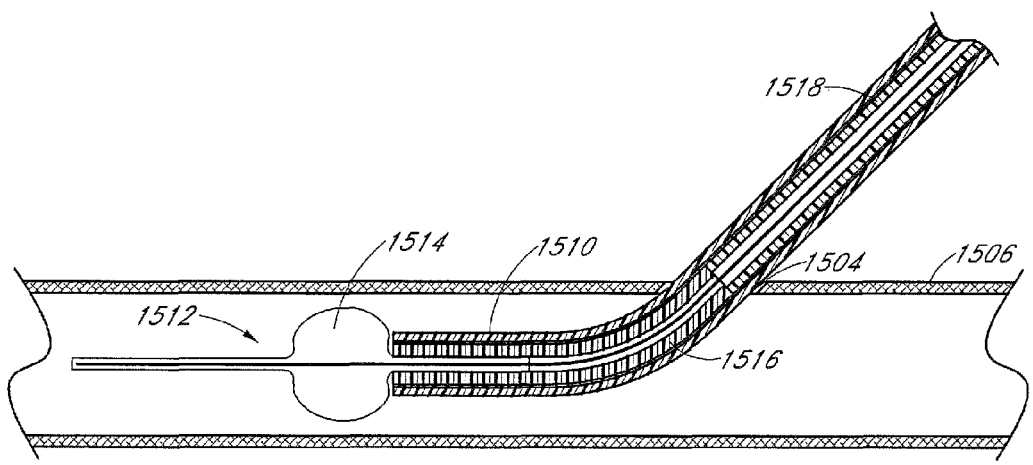

After a distal end of the sheath 1510 extends into the vessel lumen, the dilator 1508 and guidewire 1502 can be proximally retracted and removed leaving the distal end of the sheath 1510 inside the vessel lumen (FIG. 21B). A positioning assembly 1512 can then be introduced into the proximal end of the sheath 1510 and advanced distally through the sheath 1510 (FIGS. 21C-E). As described herein, the positioning assembly 1512 can include a sealant 1516 positioned at a distal portion of the positioning assembly 1512 prior to entering the sheath 1510. After a positioning element 1514 extends out from the distal end of the sheath 1510 and into the vessel lumen, the positioning element 1514 can be expanded within the vessel lumen (FIG. 21F).

Figure 21G:
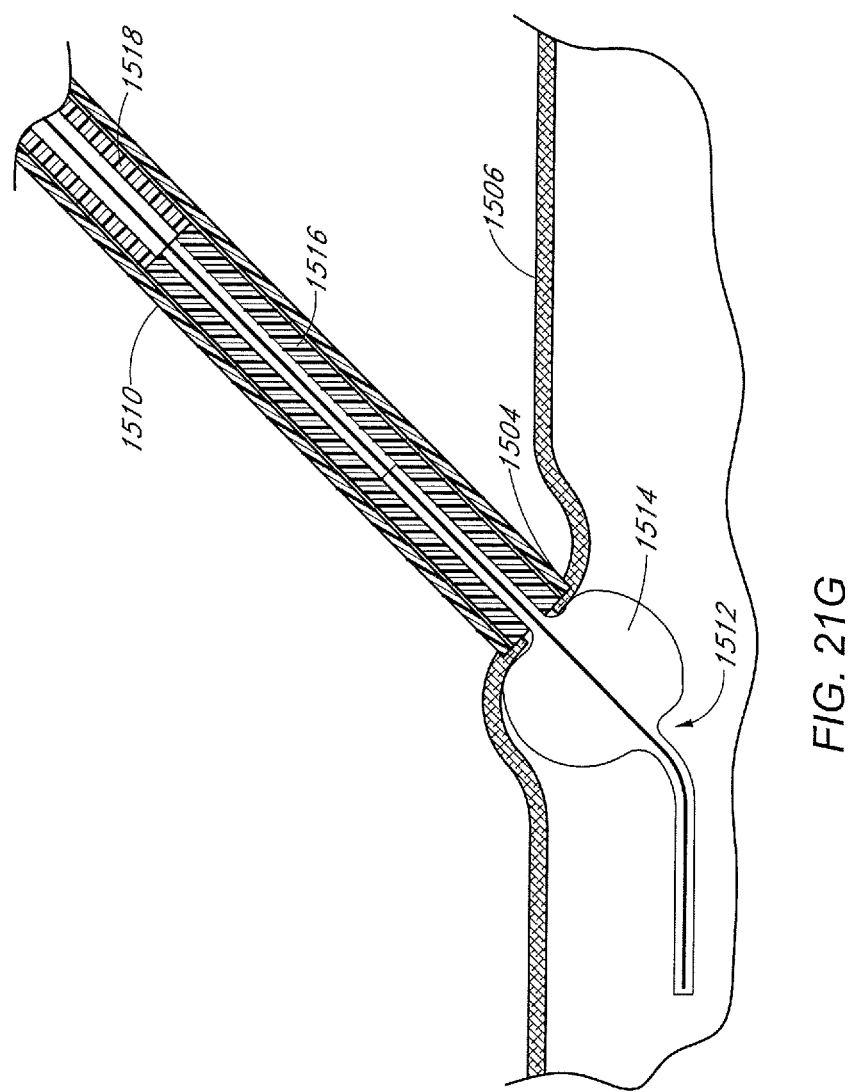
Figure 21H:
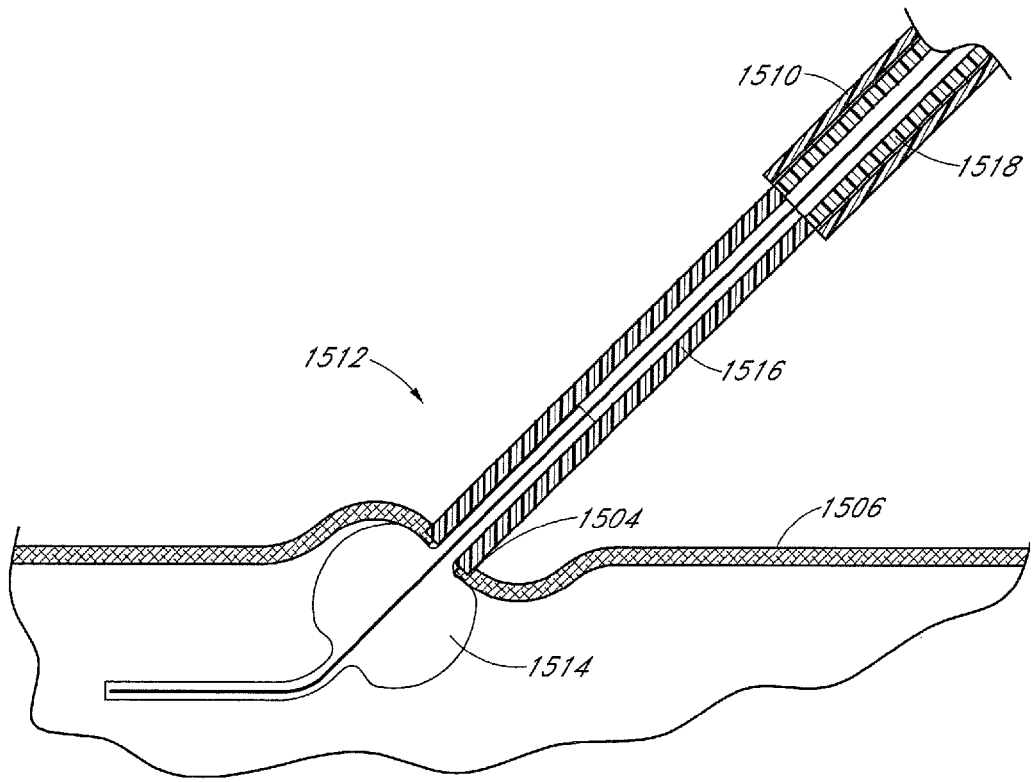
Figure 21I:
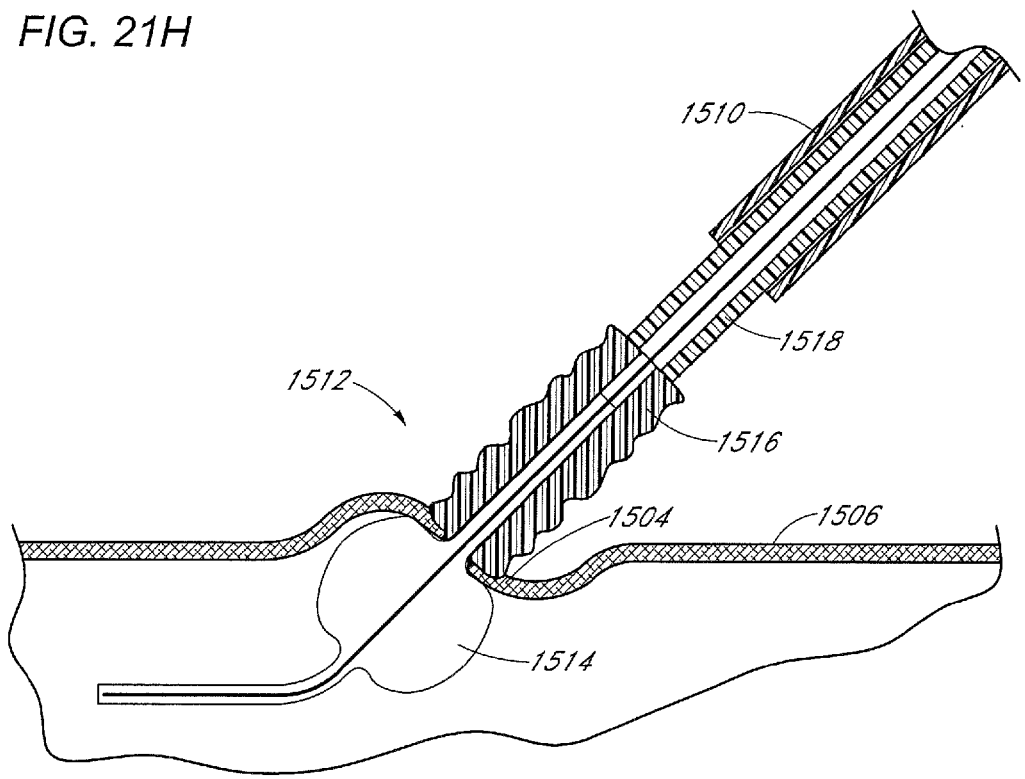

The positioning assembly 1512 can then be withdrawn to seat the positioning element 1514 against the vessel puncture 1504, and the sealant 1516 and sheath 1510 outside the vessel wall 1506 (FIG. 21G). The sheath 1510 can then be partially retracted to expose the sealant 1516 (FIG. 21H). The support member 1518 can then be advanced to tamp the sealant 1516 against the vessel wall 1506 (FIG. 21I). The positioning element 1514 may thereafter be reduced in cross-section (e.g. deflated) and proximally retracted through the sealant 1516. The support member 1518 may be left in position against the sealant during proximal retraction of the positioning element 1514, to maintain the location of the sealant. After removal of the positioning element 1514, the support member 1518 and sheath 1510 if still present within the tissue tract may be removed from the patient, leaving the sealant 1516 positioned adjacent the vessel wall 1506.

In one implementation of the invention, the positioning element 1514 is an inflatable balloon carried on a distal region of an elongate balloon catheter shaft. The balloon catheter shaft comprises an elongate tubular body having a central lumen extending therethrough to place the inflatable balloon in fluid communication with a source of inflation media, which may be coupled to the proximal end of the shaft. A central core wire extends through at least a portion of the central lumen, and through the balloon, to support the distal end of the balloon. The core wire may extend distally beyond the balloon for a length of at least about 2 mm to 10 cm, and preferably at least about 3 cm to 5 cm to provide a flexible advance segment.

The inside diameter of the central lumen is greater than the outside diameter of the core wire, to provide an inflation lumen and enable inflation of the balloon.

The sealant 1516 is preferably provided with a central lumen such that it can be pre-mounted on a distal end of the balloon catheter shaft, proximally of the inflatable balloon. The sealant 1516 may be formed as a cylindrical plug, having a central lumen extending therethrough. Alternatively, the sealant 1516 may be provided in a form of a sheet or membrane, which can be wrapped in one, two, three, four, or more layers around the catheter shaft.

Referring, for example, to FIGS. 21F and 21G, the sealant is prepositioned on the distal catheter shaft and spaced a short distance from the proximal surface of the inflated balloon. That space may be dimensioned to cooperate with the anticipated wall thickness of the vessel, such as is illustrated in FIG. 21G, so that the inflated balloon can be positioned against the interior wall of the vessel and the sealant will be positioned directly outside of the puncture adjacent the outside wall of the vessel. The space measured in an axial direction between the distal end of the sealant and the proximal surface of the balloon will typically be no greater than about 4 mm, and, in some embodiments, no greater than about 3 mm or 2 mm.

Using this construction, the sealant may be prepositioned on the balloon catheter shaft at the point of manufacture, or, in any event, at the clinical site prior to introduction of the balloon catheter into the patient. The balloon catheter and the sealant are thereafter guided as a single unit by the sheath 1510, from outside of the patient, into the proximal end of the sheath 1510, and guided by the sheath 1510 to the vessel wall. The balloon may thereafter be inflated within the vessel, and the system may be proximally withdrawn as a unit without any internal relative motion between the balloon catheter and the sealant from the distal position illustrated in FIG. 21F to the proximal, seated position in FIG. 21G. Thereafter, proximal retraction of the outer sleeve exposes the sealant.

EXAMPLES

Example 1

Chitosan salt (chloride salt, Protasan UP CL 214 from FMC BioPolymer, Molecular Weight 150-400 kDa, degree of deacetylation>90%) was mixed with PEG-ester (4-arm-10K-CM-HBA-NHS, MW 10 kDa) and PEG-amine (8-arm-20K-PEG-$NH_3^+Cl^-$, MW 20 kDa) precursors in the appropriate buffers (phosphate and borate buffers, respectively) and allowed to react to form hydrogels, which were subsequently frozen at about −37° C. and then allowed to gradually freeze dry over a period of about 20 hours. The freeze dried hydrogels were then conditioned through various humidity and temperature steps to yield freeze dried hydrogels with structural integrity able to be sliced into rectangular shapes (about 6 mm by about 15 mm). Table 1 below summarizes the thickness and blood swelling data of hydrogels synthesized by blending chitosan with PEG-ester and PEG-amine precursors in the appropriate buffers (Samples 1 to 10), before sterilization, compared to a control sample (PEG only hydrogel) that does not contain chitosan and is also tested before sterilization (Samples 11 and 12). The mole equivalent ratio of PEG-ester to PEG-amine has been varied in this example, and was tested at a range of about 1 to about 1.5. Chitosan has been varied between 0 to about 6.9% by weight in this example. The blood swelling tests were performed by dipping the freeze dried hydrogels (pre-sterilization) in bovine blood at about 37° C. for about 45 seconds and measuring the percentage of swelling by measuring the difference in weight before and after dipping in the blood.

TABLE 1

| Sample No. | PEG-Amine (g) | PEG-Ester (g) | Chitosan Chloride (g) | Final Thickness (mm) | % Swell in bovine blood[1] |
|---|---|---|---|---|---|
| 1 | 0.817 | 0.803 | 0.120 | 1.66 | 3025, 3114 |
| 2 | 0.817 | 0.803 | 0.120 | 1.83 | 2933, 2613 |
| 3 | 0.860 | 0.845 | 0.085 | 2.10 | 4532, 4552 |
| 4 | 0.860 | 0.845 | 0.085 | 2.12 | 4536, 3914 |
| 5 | 0.648 | 0.972 | 0.120 | 1.51 | 3062, 2660 |
| 6 | 0.648 | 0.972 | 0.120 | 1.64 | 2648, 2813 |
| 7 | 0.682 | 1.023 | 0.085 | 2.05 | 4103, 3756 |
| 8 | 0.682 | 1.023 | 0.085 | 2.13 | 3850, 4026 |
| 9 | 0.767 | 0.938 | 0.085 | 1.89 | 3347, 3280 |
| 10 | 0.767 | 0.938 | 0.085 | 1.71 | 3051, 2960 |

TABLE 1-continued

| Sample No. | PEG-Amine (g) | PEG-Ester (g) | Chitosan Chloride (g) | Final Thickness (mm) | % Swell in bovine blood[1] |
|---|---|---|---|---|---|
| 11 | 0.903 | 0.887 | 0 | 1.10 | 2566, 2436 |
| 12 | 0.903 | 0.887 | 0 | 1.17 | 2922, 2681 |

[1]Pre-sterile rectangular (6 mm by 15 mm) freeze dried hydrogels were tested with two samples per formulation tested for % of swelling in bovine blood.

The results of the Bovine Blood Swell are indicated in Table 1 above. Samples 11 and 12, which were made from PEG precursors only (no chitosan incorporated), demonstrate a substantial ability to swell upon contact with blood. It is believed that this swelling ability of PEG only hydrogels is due to the porosity characteristics (size and number of pores) that partially cross-linked PEG hydrogels can create upon freeze drying. The data in Table 1 demonstrates that pre-sterilization, freeze dried PEG/Chitosan copolymer sealants (Samples 1 to 10) made by covalently bonding chitosan with the PEG precursors can exhibit a swelling ability that is comparable to the swelling ability of the PEG-only hydrogels, independent of the amount of chitosan incorporated (for the ratios tested), or can even exceed the swelling ability of PEG-only hydrogels.

Example 2

Chitosan salt (sodium salt from Xianju Tengwang) was mixed with PEG-ester (4-arm-10K-CM-HBA-NHS) and PEG-amine (8-arm-20K-PEG-NH3+Cl—) precursors in the appropriate buffers (phosphate and borate buffers, respectively) and reacted until a gel is formed. The resultant hydrogel was frozen at about −37° C. and then allowed to gradually freeze dry over a period of about 20 hrs. The freeze dried hydrogels were subsequently conditioned through various humidity and temperature steps to yield freeze dried hydrogels with structural integrity allowing them to be manipulated (e.g., sliced, rolled and loaded on the distal end of a delivery catheter (e.g., MYNXGRIP® catheter). Table 2 below summarizes the amounts used and the thickness and swelling data of the final hydrogels synthesized by blending chitosan with PEG-ester and PEG-amine precursors in the appropriate buffers. The table below shows that freeze dried hydrogels synthesized by covalently bonding chitosan with the PEG precursors can substantially swell upon contact with bovine blood and that the percent swell is comparable to the control samples.

TABLE 2

| Sample No. | Chitosan (soluble) | Thickness (mm) | % Swell[2] |
|---|---|---|---|
| 1 | Control[1] | 1.68 | 3001, 3139 |
| 2 | Control[1] | 1.58 | 3336, 3230 |
| 3 | Same as control add 0.5% wt chitosan | 2.36 | 3339, 3758 |
| 4 | Same as control add 0.5% wt chitosan | 2.43 | 3670, 3257 |
| 5 | Same as control add 1% wt chitosan | 2.98 | 1277, 1055 |

[1]Control contains 0.903 g PEG-amine (8-arm-20K—PEG—NH3+Cl-) and 0.887 g PEG-ester (4-arm-10K—CM—HBA—NHS).
[2]Two samples from each hydrogel cake were tested for % of swelling in bovine blood.

Example 3

Chitosan salt (chloride salt, Protasan UP CL 213 from FMC BioPolymer, Molecular Weight 150-400 kDa, degree of deacetylation 75-90%) was mixed with PEG-ester (4-arm-10K-CM-HBA-NHS, MW 10 kDa) and PEG-amine (8-arm-20K-PEG-NH$_3^+$Cl$^-$, MW 20 kDa) precursors, at the amounts shown in Table 3 below, in the appropriate buffers (phosphate and borate buffers, respectively) and allowed to react to form hydrogels, which were subsequently frozen at about −37° C. and then allowed to gradually freeze dry over a period of about 20 hours. The mole equivalent ratio of PEG-ester to PEG-amine is about 1 in this example. The chitosan was varied between 0 to about 5.5% by weight in this example. The freeze dried hydrogels were then conditioned through various humidity and temperature steps to yield freeze dried hydrogels with structural integrity such that it is able to be sliced (about 6 mm by about 15 mm rectangles) and rolled into a cylindrical shape. Un-reacted PEG-ester and PEG-amine components (which are the same PEG components used for the freeze-dried portion of the Hydrogel sealant with no chitosan) were mixed together (at a mole equivalent ratio of 1 to 1) by melting and applied to the distal end of the freeze-dried sealant. The rolled freeze dried hydrogels with the un-reacted PEG components on the distal end were then loaded onto the distal end of a delivery catheter (i.e., a 6 French extravascular delivery catheter, MYNXGRIP® Catheter).

The delivery catheters were then subject to sterilization by e-beam. After sterilization, the hydrogels were discharged from the catheter device by using a simulated technique as in an actual use of the extravascular delivery system to assess their blood swelling performance in bovine blood. The samples that were tested were chitosan with PEG-ester and PEG-amine precursors (Formulations 3-2 to 3-6) compared to a control sample (PEG only hydrogel) that did not contain chitosan (Formulation 3-1). The blood swelling test was performed by immersing the freeze dried hydrogels (post-sterile) in bovine blood at about 37° C. for about 45 seconds and measuring the percentage of swelling by measuring the difference in weight before and after dipping in the blood (e.g., % Swell=(((Swelled weight of hydrogel−Excess Fluid Weight)−Initial Hydrogel Weight)/Initial Hydrogel Weight)×100%; where the excess fluid weight is considered as the blood that is not incorporated within the hydrogel structure). The results of the blood swelling test are reproduced below in Table 3.

TABLE 3

| Formulation No. | PEG-Amine (g) | PEG-Ester (g) | Chitosan (g) | Thickness (mm) | % Swell in bovine blood (Avg + St. Dev.)[1] |
|---|---|---|---|---|---|
| 3-1 | 0.865 | 0.925 | 0 | 1.10 | 1549 ± 239 |
| 3-2 | 0.858 | 0.907 | 0.025 | 2.10 | NT[2] |
| 3-3 | 0.850 | 0.890 | 0.050 | 1.60 | 939 ± 191 |
| 3-4 | 0.844 | 0.886 | 0.060 | 1.40 | 1358 ± 196 |
| 3-5 | 0.834 | 0.876 | 0.080 | 1.50 | 1389 ± 249 |
| 3-6 | 0.824 | 0.866 | 0.100 | 1.75 | 748 ± 169 |

[1]Post-sterile freeze dried hydrogels after loaded onto a 6Fr extravascular delivery system; 10 samples per formulation were tested for % of swelling in bovine blood.
[2]NT: Not tested. Formulation 3-2 was not tested for blood swelling because it could not be loaded onto the MYNXGRIP ® catheter system because of its thickness.

Formulation 3-1 (Control) from Table 3 above demonstrated a substantial ability to swell upon contact with blood. The data for Formulations 3-3 through 3-5 demonstrated that post-sterile freeze dried PEG/Chitosan copolymer sealants that were loaded onto a 6 Fr extravascular delivery catheter and then discharged can exhibit a swelling ability that is comparable to the swelling ability of the PEG-only hydrogels. Although the swelling ability of Formulation No. 3-6 was lower as compared to the control sample, this value (about 750% swelling in blood) is also considered to have comparable swelling as to the control (Formulation No. 3-1).

Example 4

Freeze dried PEG/Chitosan hydrogels were made as in Example 3 except that the mole equivalent ratio of PEG-ester to PEG-amine was 1.1. The hydrogels were rolled and loaded on the distal end of a delivery catheter as before (e.g., 6 Fr extravascular delivery catheter, MYNXGRIP® Catheter) and all catheters were sterilized by e-beam. The chitosan was varied between 0 to about 5.5% by weight. The blood swelling tests were performed as in Example 3. Formulation 4-1 was made from PEG precursors only (no chitosan incorporated), which is the control sample, and Formulations 4-2 to 4-6 were made with varying amounts of PEG/Chitosan, as shown in Table 4 below. The results of the blood swelling test are reproduced below in Table 4.

TABLE 4

| Sample No. | PEG-Amine (g) | PEG-Ester (g) | Chitosan (g) | Thickness (mm) | % Swell in bovine blood (Avg + Dev.)[1] |
|---|---|---|---|---|---|
| 4-1 | 0.865 | 0.925 | 0 | 1.10 | 1549 ± 239 |
| 4-2 | 0.827 | 0.938 | 0.025 | 2.10 | NT[2] |
| 4-3 | 0.815 | 0.925 | 0.050 | 1.65 | 643 ± 107 |
| 4-4 | 0.810 | 0.920 | 0.060 | 1.90 | NT[2] |
| 4-5 | 0.801 | 0.909 | 0.080 | 1.40 | 912 ± 207 |
| 4-6 | 0.792 | 0.898 | 0.100 | 1.60 | 973 ± 255 |

[1]Post-sterile freeze dried hydrogels after loaded onto a 6Fr extravascular delivery system; 10 samples per formulation were tested for % of swelling in bovine blood.
[2]NT: Not tested. Formulations 4-2 and 4-4 were not tested for blood swelling because it could not be loaded on the MYNXGRIP® catheter system because of its thickness.

Formulation 4-1 (Control) demonstrated a substantial ability to swell upon contact with blood when loaded onto the 6 Fr extravascular delivery catheter and after sterilization. In evaluating Formulations 4-3, 4-5 and 4-6, these samples demonstrated that post-sterilization, freeze dried PEG/Chitosan copolymer sealants that have been loaded onto 6 Fr extravascular delivery catheters can exhibit a swelling ability that is considered to be comparable to that of the PEG-only hydrogels.

Example 5

The blood clotting ability of PEG/Chitosan copolymer hydrogels (Formulations 3-2 to 3-6 from Example 3) was compared with the blood clotting ability of PEG-only hydrogels (control, Formulation 3-1 from Example 3) before sterilization. The samples were prepared in advance of performing the blood clotting test by cutting the freeze-dried hydrogels into disks with a diameter of about 8 mm. In performing the blood clotting test, the lyophilized disk samples were treated with bovine whole blood (anticoagulated with Acid Citrate Dextrose—ACD) and $CaCl_2$ and put in the oven at about 37° C. for about 10 minutes as part of the incubation period. After the incubation period, red blood cells that were not trapped in the clot were hemolyzed in DI water and the UV absorbance of the resulting hemoglobin solution was measured at a wavelength of about 540 nm. The higher absorbance value of the hemoglobin solution indicates a slower clotting rate, while a lower absorbance value indicates a faster clotting rate. Table 5 below summarizes the results of the blood clotting test of hydrogels made with PEG-only (Formulation 3-1, Control) compared to the hydrogels made with PEG/Chitosan copolymers (Formulation numbers 3-2 through 3-6).

TABLE 5

| Formulation No. | PEG-Amine (g) | PEG-Ester (g) | Chitosan (g) | Thickness (mm) | UV absorbance at 540 nm (Avg + St. Dev.)[1] |
|---|---|---|---|---|---|
| 3-1 | 0.865 | 0.925 | 0 | 1.10 | 0.170 ± 0.040 |
| 3-2 | 0.858 | 0.907 | 0.025 | 2.10 | 0.036 ± 0.020 |
| 3-3 | 0.850 | 0.890 | 0.050 | 1.60 | 0.033 ± 0.017 |
| 3-4 | 0.844 | 0.886 | 0.060 | 1.40 | 0.055 ± 0.031 |
| 3-5 | 0.834 | 0.876 | 0.080 | 1.50 | 0.045 ± 0.034 |
| 3-6 | 0.824 | 0.866 | 0.100 | 1.75 | 0.006 ± 0.006 |

[1]Three samples from each hydrogel formulation were tested.

From the results, it can be seen that Formulations 3-2 to 3-6, which comprise the PEG/Chitosan copolymers, result in faster clotting rates compared to hydrogels that comprise only PEG, as exhibited by the lower UV absorbance rates of the PEG/Chitosan samples. All of the PEG/Chitosan copolymers tested indicate a substantial improvement in the blood clotting ability compared to the PEG-only Control sample, independent of the amount of Chitosan incorporated.

Example 6

Similar to Example 5, the blood clotting ability of pre-sterile PEG/Chitosan copolymer hydrogels (Formulations 4-2 to 4-6 from Example 4, prior to sterilization) was compared to a pre-sterile PEG-only hydrogel (control, Formulation 4-1 from Example 4, prior to sterilization) using the blood clotting test explained above in Example 5. The test parameters of the blood clotting test were kept the same as in Example 5. Table 6 below summarizes results of the blot clotting test of hydrogels manufactured with PEG-only (Formulation 4-1, Control) compared to hydrogels manufactured with PEG/Chitosan copolymers (Formulation numbers 4-2 through 4-6).

TABLE 6

| Formulation No. | PEG-Amine (g) | PEG-Ester (g) | Chitosan (g) | Thickness (nm) | UV absorbance at 540 nm (Avg + St. Dev.)[1] |
|---|---|---|---|---|---|
| 4-1 | 0.865 | 0.925 | 0 | 1.10 | 0.201 ± 0.045 |
| 4-2 | 0.827 | 0.938 | 0.025 | 2.10 | 0.003 ± 0.005 |
| 4-3 | 0.815 | 0.925 | 0.050 | 1.65 | 0.033 ± 0.010 |
| 4-4 | 0.810 | 0.920 | 0.060 | 1.90 | 0.008 ± 0.006 |
| 4-5 | 0.801 | 0.909 | 0.080 | 1.40 | 0.083 ± 0.045 |
| 4-6 | 0.792 | 0.898 | 0.100 | 1.60 | 0.034 ± 0.027 |

[1]Three samples from each hydrogel formulation were tested.

Table 6 shows that the hydrogels that comprise PEG/Chitosan copolymers (Formulations 4-2 to 4-6) result in faster clotting rates due to the lower UV absorbance values as compared to the hydrogels that comprise PEG only (Formulation 4-1, Control). All of the PEG/Chitosan copolymers tested indicate a substantial improvement in the blood clotting ability when compared to PEG-only, independent of the amount of Chitosan incorporated.

Example 7

Similar to Example 5, the blood clotting ability of PEG only hydrogels (no chitosan incorporated) of various thicknesses was tested in order to evaluate the effect of thickness on the blood clotting ability of the hydrogel disks (diameter of about 8 mm) before sterilization. The test parameters of the blood clotting test were kept the same as in Example 5. Table 7 below summarizes results of the blot clotting test of hydrogels manufactured with PEG-only (Controls) of various thicknesses as shown below in the table.

TABLE 7

| Formulation No. | PEG-Amine (g) | PEG-Ester (g) | Chitosan (g) | Thickness (nm) | UV absorbance at 540 nm (Avg + St. Dev.)[1] |
|---|---|---|---|---|---|
| 7-1 | 0.788 | 0.814 | 0 | 0.80 | 0.226 ± 0.040 |
| 7-2 | 0.788 | 0.814 | 0 | 0.99 | 0.227 ± 0.084 |
| 7-3 | 0.881 | 0.909 | 0 | 1.00 | 0.225 ± 0.008 |
| 7-4 | 0.881 | 0.909 | 0 | 1.22 | 0.113 ± 0.023 |
| 7-5 | 0.873 | 0.917 | 0 | 1.47 | 0.156 ± 0.025 |

[1]Three samples from each hydrogel formulation were tested.

Table 7 indicates that as expected the blood clotting ability of PEG-only hydrogels increases with increasing thickness up to a certain point and then the blood clotting ability starts to decrease, unaffected by the thicker sample pieces. However, the effect of thickness on the blood clotting ability of the hydrogel disks (without chitosan) is not as significant as is the incorporation of chitosan into these hydrogel sealants. The blood clotting test data of hydrogels of similar thickness of PEG/Chitosan hydrogels as compared to PEG-only hydrogels (e.g. Formulation 7-5 from Table 7 above compared to Formulations 3-4 and 4-5 from Tables 5 and 6 respectively which are all about 1.4 mm thick) show that the formulations that contain chitosan result in substantially faster clotting rates.

Example 8

Hydrogel prototypes comprising PEG/Chitosan copolymer sealants as made in Example 3, Formulation 3-3, were loaded onto a 6 French delivery system (i.e., the MYNXGRIP® vascular closure device) and tested in an ovine model. The PEG/chitosan sealants were sized small enough to fit, i.e., be loaded, onto the 6 Fr delivery device. Seven femoral access sites were sealed using the PEG/Chitosan copolymer sealants in this study to assess their performance in femoral punctures that range in size from small bore sizes to large bore sizes. Standard catheterization techniques were followed including contemporary anticoagulation. Procedural sheaths utilized were sized to create femoral artery punctures from 7 Fr, 8.5 Fr, 9 Fr, and 10 Fr. The 6 Fr delivery systems loaded with the PEG/chitosan sealants were each deployed into one of the seven punctures. All deployments of the PEG/chitosan sealants (Formulation 3-3) using the 6 Fr delivery systems were clinically successful, e.g., the PEG/chitosan sealed the puncture. These results demonstrate that arterial closure (up to a puncture size from a 10 Fr sheath) can be feasible using a 6 Fr-compatible PEG/Chitosan sealant. The 6 French delivery device was utilized to show that a large bore puncture can be closed with a small bore device, i.e., a device that is sized smaller than the size of the puncture. However, a delivery device sized larger than 6 Fr may also be used and, in particular, a delivery device sized similar to the size of the puncture may of course be used.

It is contemplated that various combinations or subcombinations of the specific features and aspects of the embodiments disclosed above may be made and still fall within one or more of the embodiments herein. Further, the disclosure herein of any particular feature, aspect, method, property, characteristic, quality, attribute, element, or the like in connection with an embodiment can be used in all other embodiments set forth herein. Accordingly, it should be understood that various features and aspects of the disclosed embodiments can be combined with or substituted for one another in order to form varying modes of the disclosed embodiments. Thus, it is intended that the scope of the present embodiments herein disclosed should not be limited by the particular disclosed embodiments described above. Moreover, while the sealant, apparatus and/or method disclosed herein can be susceptible to various modifications, and alternative forms, specific examples thereof have been shown in the drawings and are herein described in detail. It should be understood, however, that the sealant, device and method are not to be limited to the particular forms or methods disclosed, but to the contrary, can cover all modifications, equivalents, and alternatives falling within the spirit and scope of the various embodiments described and the appended claims. Any methods disclosed herein need not be performed in the order recited. The methods disclosed herein include certain actions taken by a practitioner; however, they can also include any third-party instruction of those actions, either expressly or by implication. For example, actions such as "inserting a vascular sealant to seal a vascular puncture" include "instructing the insertion of vascular sealant to seal a vascular puncture."

The ranges disclosed herein also encompass any and all overlap, sub-ranges, and combinations thereof. Language such as "up to," "at least," "greater than," "less than," "between," and the like includes the number recited. Numbers preceded by a term such as "about" or "approximately" include the recited numbers. For example, "about 10 nanometers" includes "10 nanometers."

What is claimed is:

1. A method of sealing a vascular puncture having a size of 6 French or larger using a small bore device, the method comprising:
    providing a sealant comprising a first section including a proximal end, a distal end, and a cross-section sized for delivery into a puncture through tissue, the first section formed from a freeze-dried polyethylene glycol (PEG) and chitosan hydrogel that expands when exposed to physiological fluid within the puncture, and a second section extending from the distal end of the first section, the second section comprising non-crosslinked PEG precursors, at least some of the PEG precursors in an unreactive state;
    introducing the sealant into the puncture through tissue by deployment from a small bore delivery device; and
    exposing the sealant to fluid within the puncture, wherein, upon exposure to the physiological fluid, the PEG and chitosan hydrogel expands and seals the puncture through tissue.

2. The method of claim 1, wherein the first section comprises between about 0.5% and about 8% (by weight) chitosan.

3. The method of claim 1, wherein the second section further includes chitosan.

4. The method of claim 1, wherein the small bore device is sized at 7 French or smaller.

5. The method of claim 4, wherein the small bore device is sized at 6 French.

6. The method of claim 1, wherein the vascular puncture is sized between 7 French and 24 French.

7. The method of claim 6, wherein the vascular puncture is sized between 7 French and 10 French.

8. The method of claim 1, wherein the small bore delivery device has a diameter that is smaller than a diameter of the vascular puncture.

9. The method of claim 1, wherein the first section consists essentially of the freeze-dried hydrogel comprising PEG and chitosan.

10. The method of claim 1, wherein the first section further comprises a pH adjusting agent.

11. The method of claim 1, wherein the second section does not include chitosan.

12. The method of claim 1, wherein the second section consists essentially of the plurality of non-crosslinked PEG precursors.

13. The method of claim 1, further comprising withdrawing the sealant from a vessel and into the puncture through tissue before deployment from the small bore delivery device.

\* \* \* \* \*